(12) United States Patent
Bedouelle et al.

(10) Patent No.: US 8,357,496 B2
(45) Date of Patent: Jan. 22, 2013

(54) METHOD FOR THE DIAGNOSIS OR THE SCREENING OF AN ARBOVIRUS INFECTION, REAGENTS USEFUL IN SAID METHOD AND THEIR APPLICATIONS

(75) Inventors: Hugues Bedouelle, Paris (FR); Elodie Brient-Litzler, Versailles (FR); Philippe Dussart, Matoury Guyane (FR); Philippe Despres, La Garenne-Colombes (FR); Laetitia Bremand, Macouria Guyane (FR)

(73) Assignees: Institut Pasteur, Paris (FR); Centre National de La Recherche Scientifique, Paris (FR)

( * ) Notice: Subject to any disclaimer, the term of this patent is extended or adjusted under 35 U.S.C. 154(b) by 257 days.

(21) Appl. No.: 12/664,778

(22) PCT Filed: Jun. 13, 2008

(86) PCT No.: PCT/IB2008/002614
§ 371 (c)(1),
(2), (4) Date: Apr. 21, 2010

(87) PCT Pub. No.: WO2008/152528
PCT Pub. Date: Dec. 18, 2008

(65) Prior Publication Data
US 2010/0291586 A1 Nov. 18, 2010

(30) Foreign Application Priority Data
Jun. 15, 2007 (EP) .................................... 07290749

(51) Int. Cl.
*G01N 33/53* (2006.01)
*A61K 39/395* (2006.01)
*A61K 39/12* (2006.01)
(52) U.S. Cl. ............... 435/7.1; 424/196.11; 424/197.11; 424/218.1
(58) Field of Classification Search .................... None
See application file for complete search history.

(56) References Cited

FOREIGN PATENT DOCUMENTS
WO WO 2004/016586 A2 * 2/2004
WO WO 2006011060 A2 * 2/2006

OTHER PUBLICATIONS

Yasuhiro Kikuchi, et al., "The nucleotide sequence of the promoter and the amino-terminal region of alkaline phosphatase structural gene (phoA) of *Escherichia coli*", Nucleic Acids Research, vol. 9, No. 21, 1981.
Kerschbaumer, R.J. et al., "pDAP2: A Vector for Construction of Alkaline Phosphatase Fusion-Proteins", Immunotechonoogy, vol. 2, No. 2, pp. 145-150 (1996) XP 004052678.
Ludolfs, D et al., "Reverse ELISA for the Detection of Anti West Nile Virus IgG antibodies in Humans", European Journal of Clinical Microbiology & Infections Diseasses, vol. 26, No. 7, pp. 467-473 (Jun. 7, 2007) XP019494786.
Yang, C. et al., "Detection of IgM antibodies to Coxsackie B Viruses in Viral Myocarditis by Using a Synthetic Peptide of CVB Coat Protein VP3", FASEB Jounal(Federation of American Societies for Experimental Biology), vol. 19, No. 4, pp. a44-a45 (Mar. 6, 2005) XP009093052.
Beasley, D.W.C. et al., "Use of a Recombinant Envelope Protein Subunit Antigen for Specific Serological Diagnosis of West Nile Virus Infection", Journal of Clinical Microbiology, vol. 42, No. 6, pp. 2759-2765 (Jun. 2004) XP002461178.
Monath, T.P. et al., "Immunoglobulin M Antibody Capture Enzyme-Linked Immunosorbent Assay Elisa for Diagnosis of St-Louis Encephalitis", Journal of Clinical Microbiolgy, Vo..20, No. 4, pp. 784-790 (Oct. 1984) XP002461176.
Cuzzubbo, A. J. et al., "Comparison of PanBio Dengue Duo Enzyme-Linked Immunosorbent Assay (ELISA) and MRL Dengue Fever Virus Immunoglobulin M Capture ELISA for Diagnosis of Dengue Virus Infections in Southeast Asia", Clinical and Diagnostic Laborator Immunology, vol. 6, No. 5, pp. 705-712, (Sep. 1999) XP002461177.
Vazquez, S. et al., "Kinetics of Antibodies in Sera, Saliva, and Urine Samples From Adult Patients With Primary or Secondary Dengue 3 Virus Infections", International Journal of Infectious Diseases, vol. 11, No. 3, pp. 256-262 (Apr. 24, 2007) XP022055493.

* cited by examiner

*Primary Examiner* — Stacy B. Chen
(74) *Attorney, Agent, or Firm* — Oblon, Spivak, McClelland, Maier & Neustadt, L.L.P.

(57) ABSTRACT

Method for the diagnosis or the screening of an arbovirus infection and preferably a flaviviridae infection and more preferably a flavivirus infection, reagents useful in said method and their applications. Said method comprises: (i) contacting a sample from the subject or animal with a solid support sensitized with an Ig binding protein which is directed against a specific class of Ig molecules of the subject or animal species under consideration and (ii) incubating the immunocomplex formed in (i) with a detector molecule consisting of a hybrid protein comprising at least an arboviral ED3 domain and an alkaline phosphatase (PhoA), the detection of said immunocomplex being the sign of the presence of an arbovirus in said sample.

14 Claims, 5 Drawing Sheets

Figure 1:
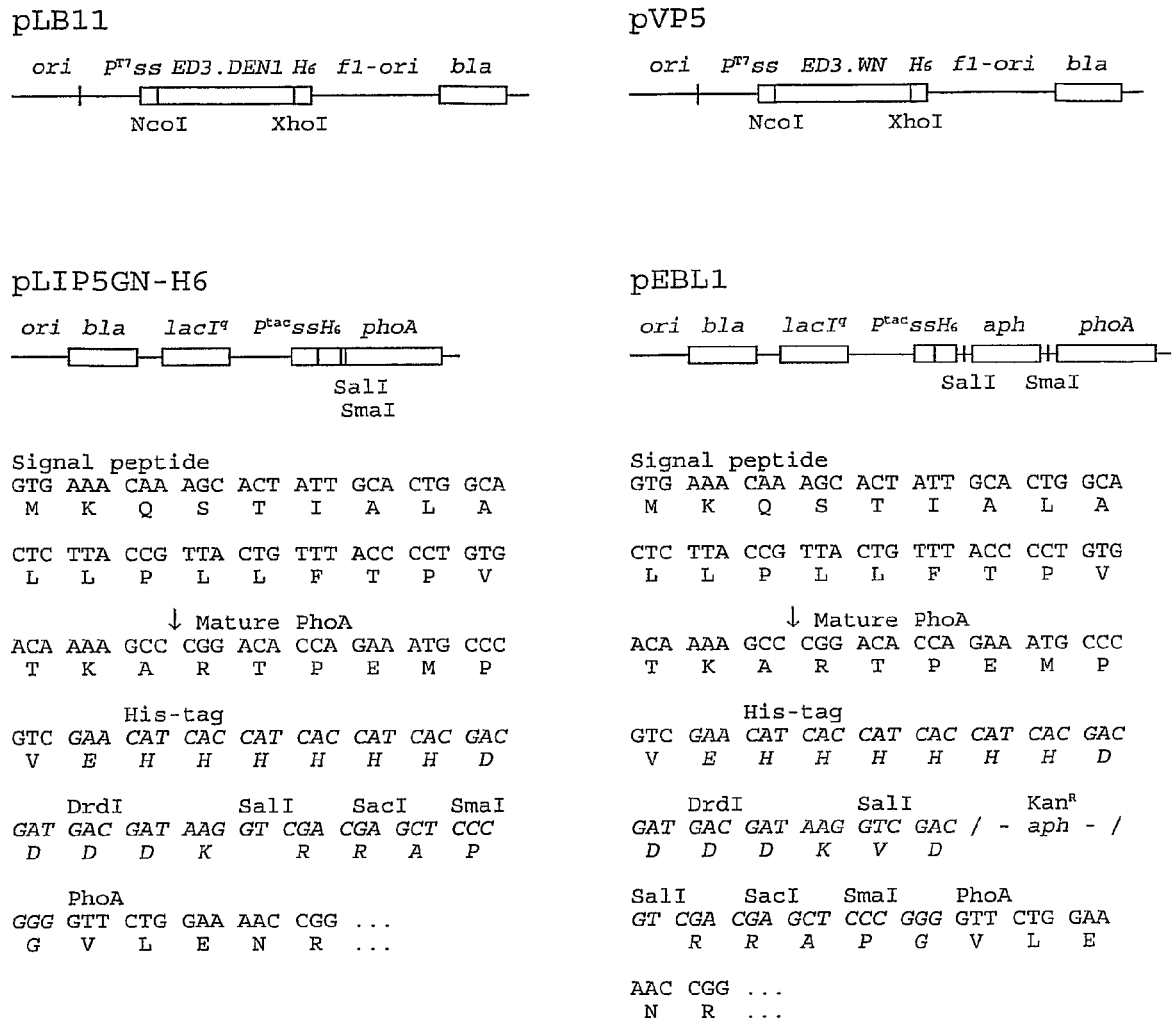

METHOD FOR THE DIAGNOSIS OR THE SCREENING OF AN ARBOVIRUS INFECTION, REAGENTS USEFUL IN SAID METHOD AND THEIR APPLICATIONS

CROSS-REFERENCE TO RELATED APPLICATIONS

The present application is a 35 U.S.C. §371 National Stage patent application of International patent application PCT/IB2008/002614, filed on Jun. 13, 2008, which claims priority to European patent application EP 07290749.6, filed on Jun. 15, 2007.

The present invention relates to a method for the diagnosis or the screening of an arbovirus infection and preferably a flaviviridae infection and more preferably a flavivirus infection, reagents useful in said method and their applications.

Arboviruses (arthropod-borne viruses) are viruses maintained in nature in cycles involving haematophagous arthropod vectors and susceptible vertebrate hosts. All arboviruses comprising an envelope protein are included in the present invention, even though the description is focused mainly on the flavivirus genus.

Many arboviruses and particularly many flaviviruses are responsible for serious human or animal diseases, in particular the yellow fever virus (YFV), dengue virus (DENV), West Nile virus (WNV), etc.

Flaviviral infections are currently detected by several methods, including virus isolation, viral-RNA detection by RT-PCR and immunochemical assays, targeted either at viral proteins or anti-viral immunoglobulin molecules. The kinetics of the appearance and the disappearance for the viral RNAs, viral proteins, virions and different classes of antibodies (IgM, IgA and IgG) are well documented for a number of flaviviruses, during primary or subsequent infections.

The detection of antibodies that are directed against a virus and present in the serum of patients, by an immunosorbent assay constitutes a well established and recommended method for the diagnosis of infections by flaviviruses (Kuno, 2003; WHO, 1997). The purposes of these diagnoses are at least two-fold: case confirmation to differentiate flaviviral diseases from other diseases with similar clinical presentations; and surveillance of the transmission.

The diagnosis of flaviviral infections is complicated by several factors. Most serological tests currently in use to measure antibodies against one flavivirus, cross-react with other members of this family (Kuno, 2003). These cross-reactions may be a problem in areas where several flaviviruses co-circulate. For example, many antibodies that are directed against WNV, cross react with JEV (Japanese Encephalitis Virus), SLEV (St Louis Encephalitis Virus) and even DENV (Granwehr et al., 2004); many antibodies, that are directed against DENV, cross-react with YFV and JEV (Vorndam and Kuno, 1997).

The four serotypes of DENV pose a special problem. The pathogenesis of the severe forms of dengue, the dengue hemorrhagic fever (DHF) and shock syndrome (DSS), remains controversial. Two main theories have been proposed. The commonly accepted hypothesis is the secondary infection or immune enhancement theory (Halstead, 2003; Mongkolsapaya et al., 2003). The other hypothesis emphasizes the involvement of viral factors (McBride and Bielefeldt-Ohmann, 2000). The differentiation between primary and secondary infections is therefore a key issue for understanding the pathogenesis of DHF. The viral mRNA and antigens are present in both primary and subsequent infections (Alcon et al., 2002). Therefore, the detection of DENV antibodies provides the only method for differentiating the different modes of infection.

Current diagnostic assays utilize either ELISA or dipstick formats for the identification of flavivirus infections.

The immunosorbent assays (ISA) for the detection of viral antibodies in the serum of patients belong to two main types: the indirect ISA and the antibody-specific capture ISA.

In an indirect ISA, a solid support is sensitized with the viral antigen (virAg). The immobilized antigen is reacted with the human or animal serum under analysis. Finally, the bound antibodies are revealed with a reporter system, which generally consists of a conjugate between an immunoglobulin binding protein (anti-Ig) and an enzyme (Enz), typically horseradish peroxidase (HRP) or alkaline phosphatase (PhoA). This being an enzyme-linked ISA (ELISA). Other types of probes can be used, e.g. a fluorophore or colloidal gold. The general scheme for an indirect ISA is the following:

$$\text{Support-virAg::Serum::anti-Ig-Reporter} \quad (1)$$

where "-" stands for a covalent bond or immobilization; and "::", for non-covalent interactions. The Ig binding protein may be specific for a particular class of Ig (anti-IgX, where X=M, A or G). In that case, one speaks of an IgX-specific indirect ISA. Several variations of the indirect ISA have been described, in particular the antigen capture ISA, the epitope blocking ISA, and the avidity ISA (Blitvich et al., 2003; Johnson et al., 2000; Matheus et al., 2005).

In the IgM, -A or -G specific capture ISA, a solid support is sensitized with an Ig binding protein (anti-IgX, with X=M, A or G), which is directed against a specific class of Ig molecules of the animal species under consideration and most generally consists of heterologous antibodies. The immobilized Ig binding protein is reacted successively with the serum under analysis, the viral antigen and then a reporter system, which generally consists of a conjugate between an antigen binding molecule (anti-virAg) and an enzyme (Enz). A generic IgX specific capture ISA (XAC-ISA) can be schematized as follows:

$$\text{Support-anti-IgX::Serum::virAg @virAg-Reporter} \quad (2)$$

Depending on the Ig binding protein (anti-IgX), one can speak of IgM, IgG or IgA antibody capture immunosorbent assays (MAC-ELISA, GAC-ELISA or AAC-ELISA).

The immunosorbent assays for IgM antibodies are among the most useful serologic procedures for determining recent infections by flaviviruses, since these IgM molecules appear early in infection, rise rapidly in the course of the disease, and are usually less cross-reactive with other viruses than IgG antibodies (Kuno, 2003). IgM molecules can be detected as soon as the 5th day after infection but their affinity for a monomeric antigen is generally lower than that of other immunoglobulin molecule types.

The MAC-ELISA is preferred over the IgM-specific indirect ELISA because the IgG antibodies from previous infections by related viruses can have a suppressive effect on the sensitivity of the latter assay (Vorndam and Kuno, 1997). It is recommended by WHO for the serological diagnosis of several flaviviral infections and in particular dengue (WHO, 1997).

The MAC-ELISA has the following advantages: If paired serum samples are available, a rising, stable or falling titer in IgM can indicate the time of infection. The ratio of IgM to IgG antibody in parallel MAC- and GAC-ELISA on a single sample can be used to differentiate primary from secondary infections since the IgM/IgG ratio is higher than one in the former case and lower in the latter (Innis et al., 1989). It can detect anti-flaviviral IgM in the cerebrospinal fluid and saliva (Kao et al., 2005; Teles et al., 2005). IgA specific ELISAs have also been developed. The IgA response develops after the IgM response but before the IgG one. The IgA/IgM ratio in parallel MAC- and AAC-ELISAs can indicate whether the infection is recent or dates from a few months, for DENV and WNV (Prince and Lape-Nixon, 2005; Talarmin et al., 1998).

The specificity of the immunosorbent assays comes mainly from the interaction between the serum under analysis and the antigen and thus depends on the nature of the antigen preparation. However, it may also come from the nature of the reporter molecule.

Until recently, the antigens in use for ISA were mainly extracts of suckling mouse brains (SMB) or cell cultures, infected by the virus under consideration. These are being progressively replaced with recombinant prM/gpE virus like particles (VLP), where prM and gpE are the precursor of the membrane protein and envelope glycoprotein of the virus or with a recombinant extracellular domain (sE) of gpE. The non-structural protein NS1 has also been used as an antigen in both IgG-specific indirect ELISA and MAC-ELISA. NS1 can differentiate between primary and secondary infections and correctly identify the serotype of the infecting DENV in the sera of patients with primary infection (Shu et al., 2004; Shu et al., 2003; Shu et al., 2002).

Many MAC-ELISAs use antiviral polyclonal antibodies as detector molecules. These polyclonal antibodies vary in potency from batch-to-batch and can be virus cross-reactive, which limits the specificity of the tests (Martin et al., 2000). Therefore, monoclonal antibodies (mAbs) are more advantageous than polyclonal antibodies (pAbs) and reduce the variations in specificity. Broadly cross-reactive mAbs, such as mAb4G2 and mAb6B6C-1, have been conjugated with enzymes and widely used as detector molecules (Kuno, 2003). Neutralization escape variants at positions S169P and G257R have mapped the epitope of mAb4G2 at the interface between domains 1 and 2 of gpE (Serafin and Aaskov, 2001).

Other types of ISA exist such as sandwich ELISA (R. J. Kerschbaumer et al., 1996) whose format is the following:

Support-anti-GST::GST-(3D6 epitope)::scFv3D6-PhoA, where anti-GST represents antibodies directed against the Glutathione-S-Transferase (GST); GST-(3D6 epitope), a hybrid protein between GST and an epitope of antibody 3D6; and scFv3D6-PhoA, a hybrid protein between a single-chain variable fragment (scFv) of antibody 3D6 and alkaline phosphatase.

Sandwich ELISA assays are used to detect the presence of an antigen in the serum of patients, but not antibodies directed against an infectious agent as in the current invention. Moreover such methods require the isolation and characterization of at least two non-competing antibodies to be used in the assay.

Another type of ISA is a reverse ELISA (D. Ludolfs et al., 2007) whose format is the following:

Support-RF::serum::rED3-HRP where the Rhumatoid Factor (RF) is an autoimmune antibody that recognizes the Fc fragment of the IgG immunoglobulins; and rED3-HRP is a chemical conjugate between Horseradish Peroxydase (HRP) and a recombinant domain 3 (rED3) of the envelope protein E from the West-Nile virus. HRP is a monomeric protein, whereas alkaline phosphatase is dimeric, and the rED3-HRP hybrid protein was obtained by chemical coupling of the two partners, rED3 and HRP.

The authors in this work explicitly mention that their "reverse ELISA" does not detect any specific IgM antibodies (page 472, left column, line 31 and following). They conclude that their reverse ELISA could improve knowledge about the prevalence of West-Nile virus infections in the world. Such a methodology is therefore most suitable for long term epidemiological studies into the prevalence of viral infections.

Another type of ISA is an indirect IgG ELISA (D. W. C. Beasley et al., 2004) whose format is the following:

Support-rED3::serum::anti-IgG-HRP where anti-IgG-HRP is a chemical conjugate between Horseradish Peroxydase and an antibody directed against human IgGs.

The authors mention explicitly that the recombinant domain rED3 is poorly bound by antibodies coated in the wells of microtiter plates (page 2764, lines 34-39), and therefore is not suitable for antibody capture ELISA.

Antigens for Use in Capture ELISA

SMB- or Cell Culture-Derived Viral Antigen

The specificity of the GAC- or MAC-ELISA does not differ significantly when using either SMB- or cell culture-derived viral antigen (Cardosa et al., 1992). MAC-ELISAs that are performed with such preparations of antigen are generally specific of a viral sero-complex but can hardly differentiate the infecting virus within a sero-complex. For example, they can differentiate between infections by DENV and either JEV or WNV (Innis et al., 1989; Martin et al., 2002). However, they have difficulty in differentiating between infections by the four DENV serotypes, even though the signal is the highest for the infecting serotype in most cases (Nawa et al., 2000). They can differentiate between WNV infections and either SLEV or JEV infections, if testing for these flaviviruses of the JEV serocomplex is done simultaneously and with a precise and specific diagnostic algorithm (Martin et al., 2002; 2004). However, such a specific diagnosis is only possible in primary infections because cross-reactivities are more important in patients experiencing secondary and further infections (Kao et al., 2005; Teles et al., 2005).

Recombinant prM/gpE-VLPs and sE as Antigens

The prM/gpE VLPs from several flaviviruses perform as well as or better than SMB-derived antigen in MAC-ELISA, according to a number of criteria measuring sensitivity, specificity, accuracy and other statistical tests (Holmes et al., 2005; Martin et al., 2002; Martin et al., 2000; Muerhoff et al., 2002). For DENV, VLPs can successfully detect the infecting serotype in primary infections (Shu et al., 2002; Shu and Huang, 2004). For SLEV, VLPs do not cross-react with IgM antibodies that are directed against WNV or the Powassan virus, contrary to the SMB-derived antigen (Purdy et al., 2004). For TBEV (Tick-Borne Encephalitis Virus), VLPs do no cross-react with IgM antibodies that are directed against JEV, contrary to the commercial antigen (Yoshii et al., 2003). For WNV however, VLPs do cross-react with a high proportion of sera from patients that are either infected with or vaccinated against other flaviviruses (JEV, SLEV, DENV, YFV) (Hogrefe et al., 2004). The extracellular domain sE of gpE, expressed as a recombinant protein in *drosophila* cells, is used in a chromatographic format of the MAC- and GAC-ELISAs. This immunochromatographic assay, using recombinant sE domains from the four serotypes of DENV, has specificities and sensitivities that are comparable to those of conventional MAC- and GAC-ELISAs, performed with SMB extracts as antigens (Cuzzubbo et al., 2001).

rED3 as an Antigen

Several factors are relevant to the use of the ED3 domain as an antigen in immunoassays: it is highly antigenic and immunogenic; the most strongly neutralizing antibodies are directed against this domain (Crill and Roehrig, 2001; Sanchez et al., 2005); the sequences of the ED3 domains are more distant than those of the other domains of gpE (Gritsun et al., 1995); the antibodies that cross-react with different flaviviruses are directed towards domains ED1 and ED2 of gpE more than towards ED3 (Crill and Chang, 2004; Kanai et al., 2006; Modis et al., 2005; Roehrig, 2003; Sanchez et al., 2005). For DENV, hybrids TrpE-ED3 between the TrpE protein from E. coli and the four serotypes of the ED3 domain have been compared with cell culture-derived viral antigens. The two kinds of antigens are equally sensitive for detecting IgM or IgG antibodies, directed against DENV, in convalescent sera. However, the TrpE-ED3 antigens are more specific than the cell culture-derived antigens for discrimination between DENV infections and YFV or JEV vaccinations (Simmons et al., 1998). For DENV, recombinant isolated ED3 domains (rED3) can successfully detect the infecting serotype in an immunoblot strip assay (Ludolfs et al., 2002). For WNV, rED3 gives a more sensitive and specific response than an SMB-derived antigen in an IgG-specific indirect ELISA, on panels of monkey, human and horse sera. It can clearly discriminate an IgG response against WNV from those against other related flaviviruses (JEV, SLEV, MVEV) (Beasley et al., 2004). For TBEV, rED3 also gives a more sensitive and specific response than an SMB-derived antigen in an IgG-specific indirect ELISA. It can distinguish between tick-borne (TBEV) and mosquito-borne (YFV, DENV) flaviviruses but cannot distinguish between members of the TBEV serocomplex of flaviviruses (Holbrook et al., 2004).

However, isolated ED3 domains have been used only in IgG- or IgM-specific indirect ISA for reasons explained below.

When using capture ELISA method with recombinant antigens, problems of valence and folding may arise and problems of detection may also arise.

Valence and Folding

Indeed, preliminary experiments have suggested that an rED3 domain from WNV is poorly bound by antibodies coated in the wells of microtiter plates or may be captured but not bound by detecting antibodies due to steric hindrance. It was therefore concluded that rED3 may not be immediately suitable for a capture assay format (Beasley et al., 2004). However, other explanations are equally plausible. The flaviviruses display 180 monomers (90 dimers) of gpE at their surface and therefore gpE and its ED3 domain are present in multiple and adjacent copies (Kuhn et al., 2002; Mukhopadhyay et al., 2003). The same molecule of IgG, IgA or IgM can bind simultaneously two to five copies of its epitope and this multivalent mode of binding results in a strong apparent affinity (avidity). The valence of the antigen is also high in prM/gpE VLPs (Ferlenghi et al., 2001); it is two for a recombinant antigen like the soluble gpE (sE), which is a dimer (Kanai et al., 2006; Modis et al., 2003; Modis et al., 2005; Rey et al., 1995), but only one for an isolated ED3 domain. Therefore, the affinity between a monomeric rED3 domain and one binding site of an IgM may be insufficient for a MAC-ELISA. Similar problems may be encountered with IgG- or IgA-capture ELISAs, especially for a primary infection. To overcome this limitation of the monomeric rED3 domains, it may be necessary to engineer their oligomerization.

The ED3 domain contains two cysteine residues. They form a disulfide bond which is necessary for the proper folding and antigenic integrity of the domain (Roehrig et al., 2004). rED3 can be produced in the periplasmic space of Escherichia coli, where the essential disulfide bond can form, in a properly folded state. The production in the periplasmic space has the added advantage that the protein can be extracted from the producing bacteria by a simple osmotic shock, in a concentrated and partially purified form.

Detection

To compare the response of a serum towards several different antigens quantitatively (e. g. towards different viral serotypes) and thus deduce its specificity, the detection system of the assay must be the same for all the tested antigens. This may not be the case when one uses polyclonal antibodies. The use of a monoclonal antibody, directed against a common epitope of different viruses or viral serotypes may lead to the following problems. (i) The binding of the antigen to the human serum may mask the epitope of the tracer monoclonal antibody. (ii) The affinities between the tracer antibody and different antigens may depend on the structural context of the epitope. As a result, the relation between the output signal of the assay and the amount of captured antigen may vary for different antigens.

Therefore there is a need for reagents better adapted to ELISA tests and more preferably to XAC-ELISA tests than the reagents of the prior Art.

Therefore, the present invention relates to a method for the diagnosis or the screening of an arbovirus in a subject or animal host, characterized in that it comprises:

(i) contacting a sample from the subject or animal with a solid support sensitized with an Ig binding protein which is directed against a specific class of Ig molecules of the subject or animal species under consideration and most generally consists of heterologous antibodies (anti-IgX antibodies) and (ii) incubating the immunocomplex formed in (i) with a detector molecule consisting of a hybrid protein comprising at least an arboviral ED3 domain and preferably a flaviviral ED3 domain and an alkaline phosphatase (PhoA), the detection of said immunocomplex being the sign of the presence of an arbovirus in said sample.

According to an advantageous mode of carrying out said method, the Ig binding protein is selected in the group consisting of anti-IgM, anti-IgG and anti-IgA (anti-IgX, with X=M, A or G).

According to another advantageous mode of carrying out said method, said arbovirus is preferably a flavivirus.

According to another advantageous mode of carrying out said method, said alkaline phosphatase is selected from the group consisting of rat, mouse, chicken, bovine, yeast and bacterial alkaline phosphatases, preferably alkaline phosphatase of E. coli.

According to a further advantageous mode of carrying out said method, said hybrid protein further comprises a polypeptide tag, useful, for instance for purifying said hybrid protein from a periplasmic extract. Examples of such polypeptide tags may be HIS (hexahistidine (SEQ ID NO: 32), c-MYC, HA, VSV-G, HSV, V5 and FLAG (Sigma products).

Thus, according to a further advantageous mode of carrying out said method, said hybrid protein comprises preferably a hexahistidine (SEQ ID NO: 32), an appropriate flaviviral ED3 domain and the alkaline phosphatase of E. coli and comprises SEQ ID NO:25.

Preferably the alkaline phosphatase consists of SEQ ID NO: 25.

According to said mode of carrying out the method, said alkaline phosphatase of E. coli is modified. More preferably said alkaline phosphatase of E. coli includes two mutations in its active site: D153G and D330N and comprises SEQ ID NO: 24 (with the numbering of Le Du et al., 2002). Such a modified PhoA have been described in European Patent Application n° 0 752 475.

Preferably the alkaline phosphatase consists of SEQ ID NO: 24.

Other modifications to the alkaline phosphatase are possible and are encompassed by the present invention.

Unexpectedly, by using the detector molecule as specified here above, i.e. comprising at least the flaviviral domain ED3 and an alkaline phosphatase of E. coli, and preferably hybrid proteins between a hexahistidine (SEQ ID NO: 32), a flaviviral domain ED3 and an alkaline phosphatase of E. coli, preferably a modified alkaline phosphatase, the IgX antibody capture immunosorbent assay for the detection of flaviviruses is significantly improved at several levels:

(i) replacement of the crude preparations of reagents (antigen or detection system) that are used in some assays, by defined and homogeneous molecular species (ii) decrease of the number of reagents and steps that are necessary for the assays (iii) replacement of all the elements of the assays that involve the manipulation of infectious viruses, animals, or cell culture in safety laboratories for their preparation, by recombinant elements that can be produced in bacteria and purified easily.

Thus, the detector molecule is preferably a (H6-ED3-PhoA)$_2$ hybrid (H6 disclosed as SEQ ID NO: 32); therefore, the binding of the (H6-ED3-PhoA)$_2$ hybrids (H6 disclosed as SEQ ID NO: 32) was revealed through the enzymatic activity of their PhoA portion. The numerous substrates of PhoA, that produce colorimetric or chemo-luminescent reactions, may be used for this revelation. Preferably, microtiter plates to immobilize the anti-IgG or anti-IgM antibodies were used. Other types and formats of supports could be used for these immobilizations, in particular optical fibers.

Thus, an assay with the (H6-ED3-PhoA)$_2$ hybrids (H6 disclosed as SEQ ID NO: 32) may be performed for the detection of other immunoglobulin types, IgA and IgE, directed against the ED3 domain, to the detection of immunoglobulins from man and different animals, for instance mouse, bovine and horse, and to their detection in other body fluids than serum. This assay may also be performed with the ED3 domains from other arboviruses and other flaviviruses than those cited since the E glycoproteins from the viruses of this taxonomic group have highly homologous structures. It may be performed with hybrids between other antigenic proteins or protein fragments, whether they come from pathogenic agents or not, and whether they are present in a monomeric or multimeric state in these agents. It may be extended to bifunctional hybrid proteins that would include another tracer than PhoA. Finally, it could be extended to cases where the oligomerization of the antigen is obtained by genetic fusion or chemical coupling with a specific protein module, distinct from the tracer. The construction of the hybrids is greatly facilitated by the possibility of chemically synthesizing the DNA segment coding for the ED3 domain on the basis of its nucleotide or amino-acid sequence.

Bifunctional dimeric hybrids like (H6-ED3-PhoA)$_2$ (H6 disclosed as SEQ ID NO: 32) or more generally (Ag-PhoA)$_2$ have numerous applications. They can be used (i) to detect antibodies directed against the antigen (Ag) that is fused with PhoA; (ii) to detect antibodies directed against the pathogen which the antigen comes from or mimics; (iii) to diagnose infections by a pathogen or validate a vaccination by a pathogen or an immunogen; (iv) to study the epidemiology of a pathogen; (v) to study the interaction between the protein or protein fragment that is fused with PhoA, and molecules, proteins or cells; (vi) to screen and identify, in a chemical library, molecules that modify the interaction between the fused protein or protein fragment and a target molecule, protein of cell.

The use of rED3 to successfully detect IgM in the serum of infected individuals has not been described previously.

The current invention relies on the possibility of simultaneously dimerising a recombinant antigen and fusing it with an enzymatic tracer, by constructing a hybrid between its gene sequence and the alkaline phosphatase gene. In this way, a reagent is obtained that can detect low affinity antibodies; for example IgM immunoglobulins, which are pentameric and appear early in infections by arboviruses. This early detection can be used as a tool in the management of epidemics. Therefore, it clearly differs from assays that are based on the detection of IgGs and are only used in retrospective studies, such as variously sandwich, reverse and indirect ELISA.

In particular the advantages of the methods and reagents according to the current invention over the prior art include: (i) the production of diagnosis reagents in low safety laboratories; (ii) the production of a single reagent per virus, in a single step and without any chemical reaction step; (iii) the ability to detect IgMs, which appear early in infection and have low affinities, with artificial dimeric antigens; (iv) the specificity of detection towards the types of viruses and infections; (iv) the simplification and speeding up of the diagnosis assay by fusion between the antigen and an enzymatic tracer.

Therefore preferably, said hybrids (H6-ED3-PhoA)$_2$ (H6 disclosed as SEQ ID NO: 32) were constructed, at the genetic level between sequences encoding a hexahistidine (SEQ ID NO: 32), the viral domain ED3, and the alkaline phosphatase of E. coli. The hexahistidine tag (SEQ ID NO: 32) enabled the purification of the hybrids on a column of nickel ions. PhoA is a dimeric periplasmic protein. The fusion of a passenger protein with PhoA at the genetic level results in the dimerisation of the hybrid protein, its export into the periplasmic space, and the preservation of the folds and functions of the two partners (Boulain and Ducancel, 2004). Moreover, the symmetrical points of insertion for the passenger protein in the crystal structure of the PhoA dimer are located on the same side of the molecule, close to one another (17.6 Å) and far from the catalytic sites (>32.5 Å) (Le Du et al., 2002).

Therefore, the construction of hybrids (ED3-PhoA-H6)$_2$ (H6 disclosed as SEQ ID NO: 32) solves the problem of the antigenic valence. The hybrids include their own enzymatic tracer and the enzymatic portion of the hybrid does not depend on the nature of its antigenic portion. With this new reagent, a MAC- or AAC- or MAC-ELISA involves only three participating molecules, according to the scheme:

Support-anti-IgX::serum::(H6-ED3-PhoA)$_2$(H6 disclosed as SEQ ID NO: 32)     (3)

where X=M, A or G.

According to another mode of carrying out the method of the invention, the envelope protein domain 3 polypeptide is selected in the group consisting of a yellow fever virus envelope protein domain 3 polypeptide, a West Nile virus envelope protein domain 3 polypeptide, a Dengue virus envelope protein domain 3 polypeptide, a St Louis encephalitis virus envelope protein domain 3 polypeptide, a Murray Valley encephalitis virus envelope protein domain 3 polypeptide and a Japanese encephalitis virus envelope protein domain 3 polypeptide.

More preferably, the ED3 domain is in particular from WNV (noted ED3.WN), from Yellow fever virus (ED3-YF) or from Dengue virus (serotypes 1, 2, 3 or 4) and preferably from serotype 1 of DENV (noted ED3.DEN1).

ED3 polypeptides of Flavivirus are described for instance in International PCT Application WO 2004/016586.

These new reagents unexpectedly simplify the MAC-, AAC- and GAC-ELISAs, contribute to make them more reproducible and quantitative, and therefore specific. They need only low levels of biological security and technical means for their preparation.

The instant invention also relates to a hybrid protein, characterized in that it comprises an appropriate polypeptide tag, an arbovirus ED3 domain and an alkaline phosphatase.

In particular the present invention relates to a hybrid protein which can be used in a method according to the current invention.

According to an advantageous embodiment of said hybrid protein, it comprises hexahistidine (SEQ ID NO: 32), an appropriate flaviviral ED3 domain and the alkaline phosphatase of E. coli.

Said hybrid protein is preferably in a multimeric form and more preferably in a dimeric form, such that for instance (H6-ED3-PhoA)₂ (H6 disclosed as SEQ ID NO: 32)

According to another advantageous embodiment of said hybrid protein:
when the ED3 domain is from DEN1 virus, said hybrid protein (H6-ED3.DEN1-PhoA (H6 disclosed as SEQ ID NO: 32)) presents the sequence (SEQ ID NO:2).
when the ED3 domain is from DEN2 virus, said hybrid protein (H6-ED3.DEN2-PhoA (H6 disclosed as SEQ ID NO: 32)) presents the (SEQ ID NO:4).
when the ED3 domain is from DEN3 virus, said hybrid protein (H6-ED3.DEN3-PhoA (H6 disclosed as SEQ ID NO: 32) presents the sequence (SEQ ID NO:6).
when the ED3 domain is from DEN4 virus, said hybrid protein (H6-ED3.DEN4-PhoA (H6 disclosed as SEQ ID NO: 32)) presents the sequence (SEQ ID NO:8).
when the ED3 domain is from West Nile virus, said hybrid protein (H6-ED3.WN-PhoA (H6 disclosed as SEQ ID NO: 32)) presents the sequence (SEQ ID NO:10) and
when the ED3 domain is from yellow fever virus, said hybrid protein (H6-ED3.YF-PhoA (H6 disclosed as SEQ ID NO: 32)) presents the sequence (SEQ ID NO:12).

The invention also relates to the nucleic acids encoding the hybrid proteins according to the invention.

Preferably, said nucleic acid is selected in the group consisting of SEQ ID NO:1 encoding H6-ED3.DEN1-PhoA hybrid protein (H6 disclosed as SEQ ID NO: 32), SEQ ID NO:3 encoding H6-ED3.DEN2-PhoA hybrid protein (H6 disclosed as SEQ ID NO: 32), SEQ ID NO:5 encoding H6-ED3.DEN3-PhoA hybrid protein (H6 disclosed as SEQ ID NO: 32), SEQ ID NO:7 encoding H6-ED3.DEN4-PhoA hybrid protein (H6 disclosed as SEQ ID NO: 32), SEQ ID NO:9 encoding H6-ED3.WN-PhoA hybrid protein (H6 disclosed as SEQ ID NO: 32) and SEQ ID NO:11 encoding H6-ED3.YF-PhoA hybrid protein (H6 disclosed as SEQ ID NO: 32).

Said hybrid proteins may be obtained according to a method similar as the ones described in EP 0 407 259 and in EP 0 752 475.

Preferably they are obtained by inserting the correct ED3 in the expression vector pEBL1 (SEQ ID NO:13), containing a modified alkaline phosphatase (SEQ ID NO: 24) comprising two mutations (D153G and D330N), with the numbering of Le Du et al., 2002.

Said expression vector has been deposited at the CNCM (Collection Nationale de Culture de Microorganismes, 28 rue du Docteur Roux, 75015 PARIS) on Apr. 23, 2007 under the accession number I-3747.

The invention also relates to a method of preparing a hybrid protein according to the invention, said method being characterized in that it comprises:
(a) obtaining an expression vector containing the sequence encoding an hybrid protein as defined here above by inserting the sequence coding for the appropriate arboviral ED3 polypeptide and preferably flaviviral ED3 polypeptide in the vector pEBL1 (SEQ ID NO:13),
(b) transforming an appropriate E. coli strain, preferably the XL1-blue strain (described by Bullock et al., 1997) with the expression vector obtained in (a),
(c) culturing said modified strains in an appropriate medium and
(d) purifying the tag-ED3-PhoA hybrid protein from the periplasmic extract.

When the tag is an hexahistidine (SEQ ID NO: 32), step (d) of purifying is performed by affinity chromatography on a column of NiNTA resin.

The different expression vectors thus obtained comprise the sequence expressing the appropriate hybrid proteins:

| Vector | Hybrid protein expression |
| --- | --- |
| pEBL11 | H6-ED3-DEN1-PhoA (H6 disclosed as SEQ ID NO: 32) |
| pEBL12 | H6-ED3-DEN2-PhoA (H6 disclosed as SEQ ID NO: 32) |
| pEBL13 | H6-ED3-DEN3-PhoA (H6 disclosed as SEQ ID NO: 32) |
| pEBL14 | H6-ED3-DEN4-PhoA (H6 disclosed as SEQ ID NO: 32) |
| pEBL15 | H6-ED3-WN-PhoA (H6 disclosed as SEQ ID NO: 32) |
| pEBL17 | H6-ED3-YF-PhoA (H6 disclosed as SEQ ID NO: 32) |

According to a mode of carrying said method, the expression vector of step (a) is selected in the group consisting of an expression vector of a hybrid protein as defined here above and more preferably the hybrid protein H6-ED3.DEN1-PhoA (H6 disclosed as SEQ ID NO: 32) (pEBL11, deposited at the CNCM (Collection Nationale de Culture de Microorganismes, 28 rue du Docteur Roux, 75015 PARIS) on Apr. 23, 2007 under the accession number I-3748) and the hybrid protein H6-ED3.WN-PhoA (H6 disclosed as SEQ ID NO: 32) (pEBL15, deposited at the CNCM (Collection Nationale de Culture de Microorganismes, 28 rue du Docteur Roux, 75015 PARIS) on Apr. 23, 2007 under the accession number I-3749).

The present invention also relates to a method for screening for arbovirus antibodies and preferably flavivirus antibodies in a subject or an animal, said method comprising:
(i) contacting a sample from said subject or animal with a solid support sensitized with an Ig binding protein which is directed against a specific class of Ig molecules of subject or the animal species under consideration,
(ii) incubating the immunocomplex formed in (i) with a detector molecule consisting of a hybrid protein comprising at least a arboviral ED3 domain and an alkaline phosphatase and
(iii) detecting the presence of said arbovirus antibodies.

Said detection is preferably performed by adding pNPP and measuring the formation of paranitrophenol.

In all the mentioned methods and kits the Ig binding protein, the ED3 domain, the alkaline phosphatase and the polypeptide tag are as defined above.

The invention also relates to a kit for diagnosing and/or screening for arbovirus antibodies and preferably flavivirus antibodies in a subject comprising:
a solid support sensitized with an Ig binding protein which is directed against a specific class of Ig molecules of the animal species under consideration and most generally consists of heterologous antibodies (anti-IgX antibodies) and at least a hybrid protein comprising at least an arbovirus ED3 domain and an alkaline phosphatase, at least one positive control, preferably a reference serum from an infected individual and at least one negative control, preferably a reference serum from a non-infected individual.

Preferably, the Ig binding protein is selected in the group consisting of anti-IgM, anti-IgG and anti-IgA (anti-IgX, with X=M, A or G), and said hybrid protein comprises a hexahistidine (SEQ ID NO: 32), a viral ED3 domain of an appropriate flavivirus and the alkaline phosphatase of *E. coli*.

According to an advantageous embodiment of said kit, the alkaline phosphatase is a modified alkaline phosphatase including two mutations in its active site: D153G and D330N (with the numbering of Le Du et al.).

Preferably the alkaline phosphatase comprises SEQ ID NO: 24.

The invention also relates to the use of a hybrid protein comprising an appropriate antigen of a pathogen and an alkaline phosphatase, for an in vitro diagnostic of infections by said pathogen or for studying the epidemiology of said pathogen.

The invention also relates to the use of a hybrid protein comprising an appropriate antigen of a pathogen and an alkaline phosphatase, for an in vitro validation of a vaccination against said pathogen or an immunogen thereof.

The invention also relates to the use of a hybrid protein comprising a protein or a fragment thereof and alkaline phosphatase to study the interaction between said protein or fragment thereof fused with PhoA and molecules, proteins or cells.

The invention also relates to a method for the diagnosis of an infection by a pathogen, for validating a vaccination by a pathogen or an immunogen thereof or for studying the epidemiology of said pathogen, characterized in that it comprises:

(i) contacting a sample from a subject or an animal with a solid support sensitized with an Ig binding protein which is directed against a specific class of Ig molecules of the animal species under consideration, (ii) incubating the immunocomplex formed in (i) with a detector molecule consisting of a hybrid protein comprising an appropriate antigen of a pathogen and alkaline phosphatase, the presence of said immunocomplex being the sign of said infection.

The invention also relates to a method for studying the interaction between a protein or a fragment thereof fused to PhoA and molecules, proteins or cells, characterized in that it comprises:

(i) contacting said molecule, protein or cell with a hybrid protein comprising the protein or a fragment thereof fused to PhoA and (ii) detecting the complex eventually formed between the protein or a fragment thereof fused to PhoA and said molecule, said protein or said cell.

The invention also relates to a method for screening for anti-arbovirus compounds, said method comprising:

(i) contacting an anti-arbovirus antibody or a receptor of a surface molecule of an arbovirus, eventually bound to a solid support with a hybrid protein comprising an epitope of an arbovirus fused to PhoA (ii) detecting the complex formed between said anti-arbovirus antibody or said receptor and said epitope by measuring an appropriate signal, for instance the formation of paranitrophenol (iii) adding a compound to be tested and (iv) detecting if the amount of complex formed between said anti-arbovirus antibody or said receptor and said epitope has decreased in relation to the amount of complex detected in step (ii), by measuring an appropriate signal and comparing the signal obtained with the signal obtained in (ii).

In all the methods the formation of the immunocomplex is directly detected by adding 4-nitrophenylphosphate (pNPP) and measuring the formation of paranitrophenol.

Besides the above provisions, the invention also comprises other provisions which would emerge from the following description, which refers to examples of implementation of the invention and also to the attached drawings, in which:

FIG. 1. Structures of plasmids pLB11, pVP5, pLIP5GN-H6 (H6 disclosed as SEQ ID NO: 32) and pEBL1. The bla and aph genes code for resistances to ampicillin and kanamycin respectively. Ss for signal sequence and H6 (SEQ ID NO: 32) for hexahistidine (SEQ ID NO: 32). Bottom part, details of the sequence between the 5'-end of the phoA signal sequence and the main part of the phoA gene in pLIP5GN-H6 (H6 disclosed as SEQ ID NO: 32) and pEBL1. FIG. 1 discloses the coded sequence for pLIP5GN-H6 as SEQ ID NOS 33, 34 and 23, respectively, in order of appearance. FIG. 1 discloses the pEBL1 coded sequence as SEQ ID NOS 20-23, respectively, in order of appearance. The vertical arrow indicates the cleavage site of the signal peptide. The residues that do not belong to the phoA gene or its product are italicized.

Figure 2:
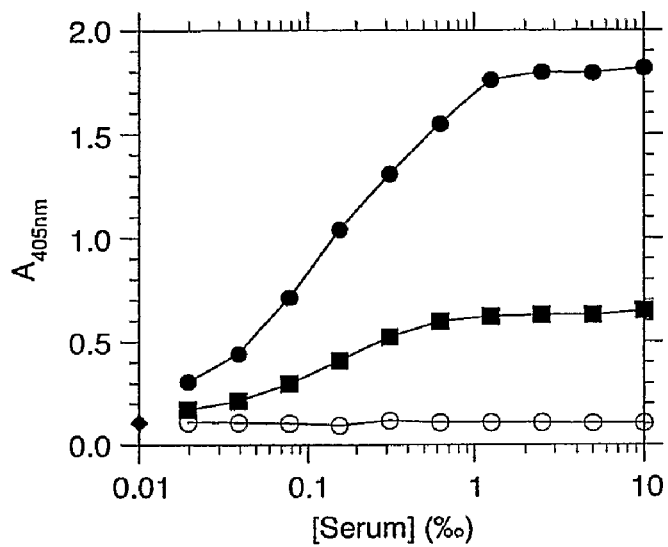

FIG. 2. Simplified GAC-ELISA of murine serums, performed with the H6-ED3.DEN1-PhoA hybrid (H6 disclosed as SEQ ID NO: 32). Closed symbols, serum from a mouse infected with DENV1; open symbols, control serum of a non-infected mouse. Squares, revelation for 2.5 h at 25° C.; Circles, revelation overnight at 4° C.; diamond, average value of the blanks. The signals of the control serum after 2.5 h and overnight superimpose.

Figure 3:
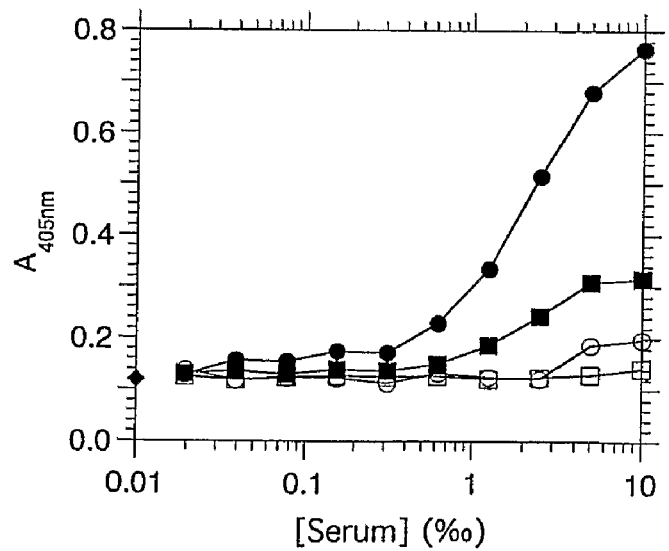

FIG. 3. Simplified MAC-ELISA of murine serums, performed with the H6-ED3.WN-PhoA hybrid (H6 disclosed as SEQ ID NO: 32). Closed symbols, serum from a mouse immunized with gpE.WN; open symbols, control serum of a non-immunized mouse. Squares, revelation for 3 h at 25° C.; circles, revelation overnight at 4° C.; diamond, average value of the blanks.

Figure 4:
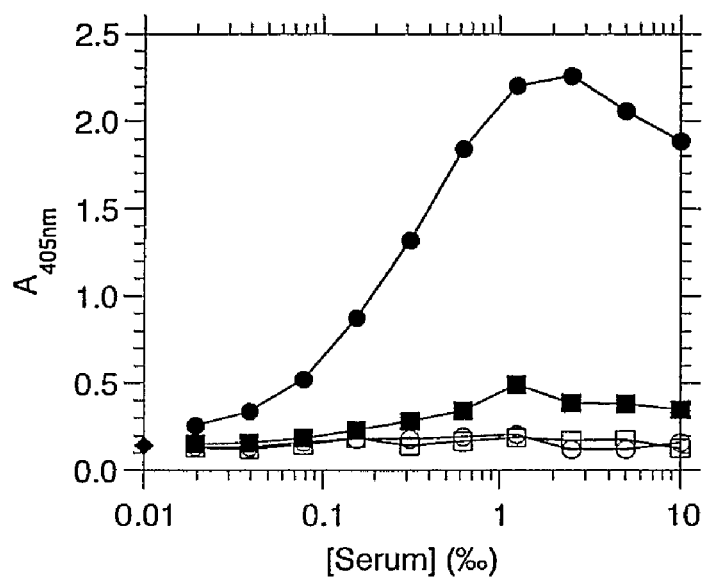

FIG. 4. Specificity of a simplified GAC-ELISA towards the antigen. The assay was performed with the H6-ED3.DEN1-PhoA (H6 disclosed as SEQ ID NO: 32) and H6-ED3.WN-PhoA hybrids (H6 disclosed as SEQ ID NO: 32) in parallel. Closed symbols, serum from a mouse infected with DENV1; open symbols, control serum of a non-infected mouse. Circles, cognate H6-ED3.DEN1-PhoA antigen (H6 disclosed as SEQ ID NO: 32); squares, non-cognate H6-ED3.WN-PhoA antigen (H6 disclosed as SEQ ID NO: 32); diamond, average value of the blanks. The revelation was conducted overnight at 4° C.

Figure 5:
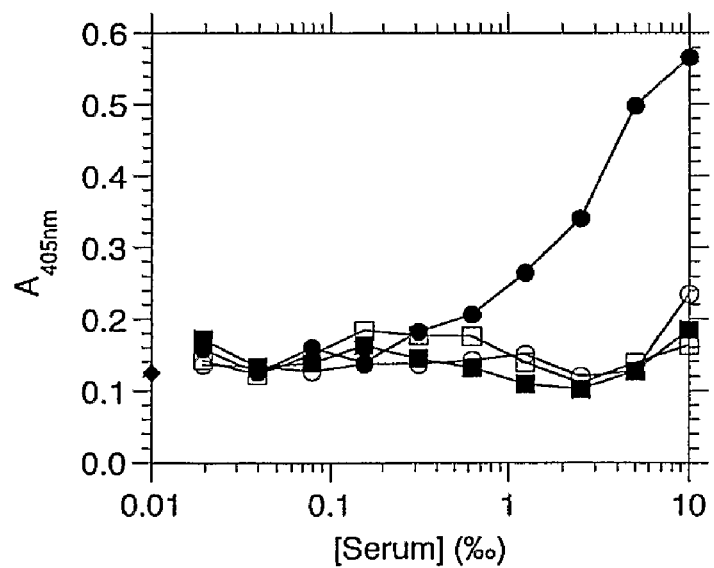

FIG. 5. Specificity of a simplified MAC-ELISA towards the antigen. The assay was performed with the H6-ED3.DEN1-PhoA (H6 disclosed as SEQ ID NO: 32) and H6-ED3.WN-PhoA hybrids (H6 disclosed as SEQ ID NO: 32) in parallel. Closed symbols, serum from a mouse infected with WNV; open symbols, control serum of a non-infected mouse. Circles, cognate H6-ED3.WN-PhoA antigen (H6 disclosed as SEQ ID NO: 32); squares, non-cognate H6-ED3.DEN1-PhoA antigen (H6 disclosed as SEQ ID NO: 32); diamond, average value of the blanks. The revelation was conducted overnight at 4° C.

Figure 6:
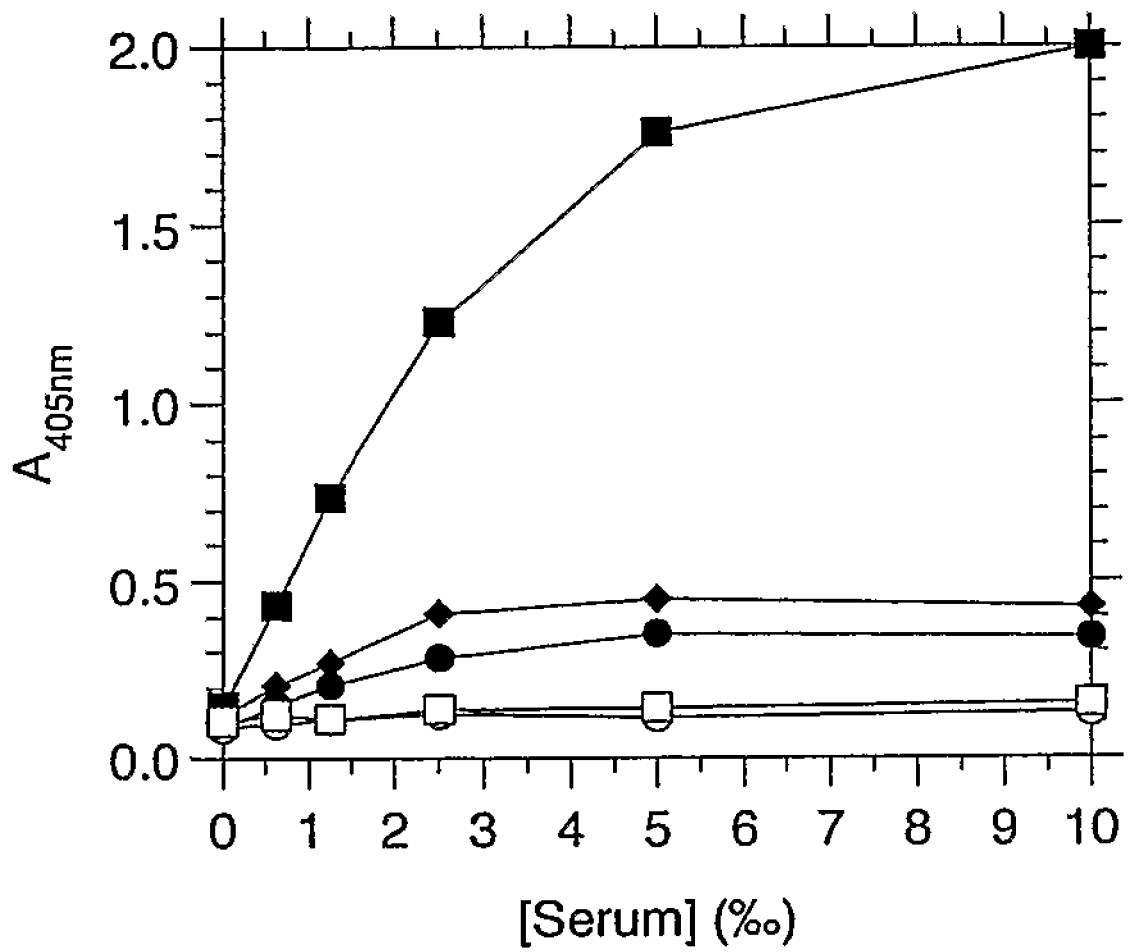

FIG. 6. Concentration dependence of the signal in a simplified MAC-ELISA of human serums, performed with the H6-ED3.DEN1-PhoA hybrid (H6 disclosed as SEQ ID NO: 32). Closed symbols, serums from patients who had experienced a primary infection with DENV1; open symbols, secondary infections with DENV1. The revelation was conducted for 3 h at 25° C.

Figure 7:
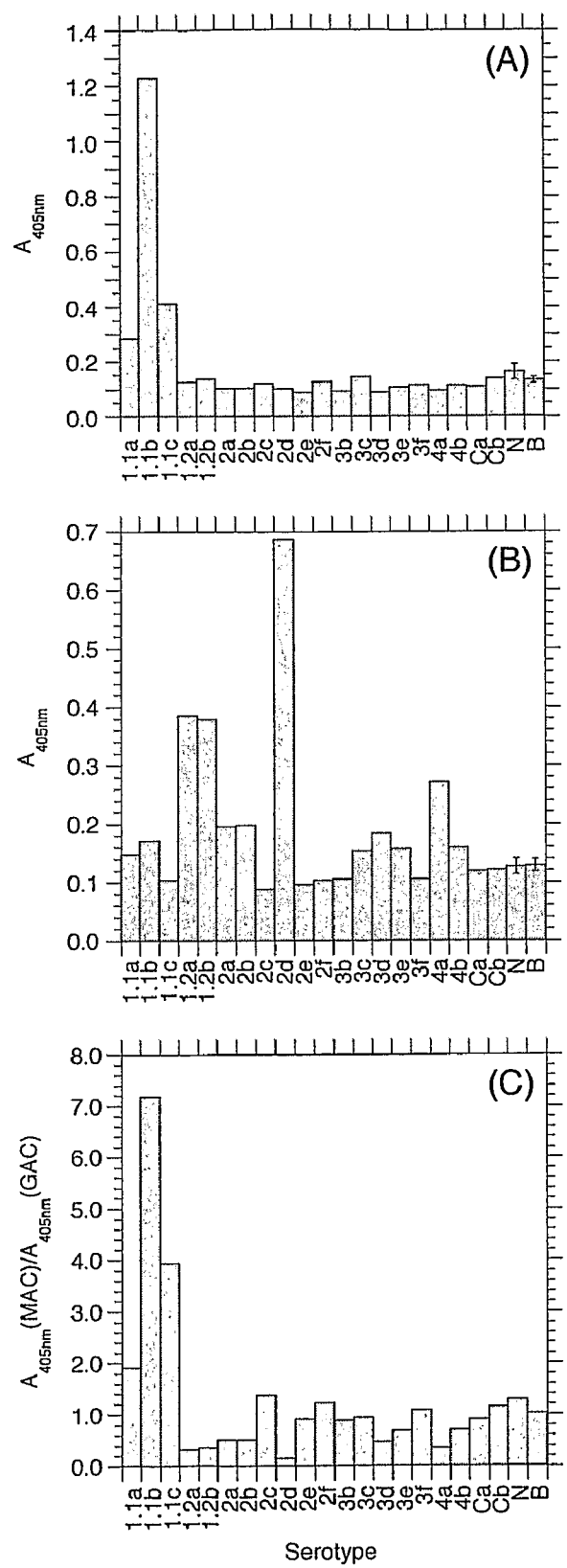

FIG. 7. Simplified MAC- and GAC-ELISA of serums from patients who had experienced infections with the four serotypes of DENV, performed with the H6-ED3.DEN1-PhoA hybrid (H6 disclosed as SEQ ID NO: 32). The serums were diluted 400-fold and the revelation of the assays was conducted for 3 h at 25° C. (A) Simplified MAC-ELISA. (B) Simplified GAC-ELISA. (C) Ratio r of the signals in the MAC- and GAC-ELISA. Samples 1.1, serums of primary infections by DENV1; 1.2, serums of secondary infections with DENV1; 2, 3 and 4, serums of infections by DENV2, -3 and -4; C, serums of healthy individuals; N and B, signals in assays where the serum or the anti-human Ig was omitted respectively.

The following examples illustrate the invention but in no way limit it.

EXAMPLE 1

Materials and Methods

Media, Buffers and Kits

The culture media LB (Sambrook and Russell, 2001) and SB (Plückthun, 1996) have been described. Ampicillin was used at 200 µg/mL and kanamycin at 50 µg/mL. LB medium with ampicillin was used for all the genetic constructions. The preparations of plasmid DNA were performed with the Qiaprep Spin Miniprep Kit, the extraction of DNA from agarose gels with the Gel Extraction Kit (both from Qiagen), the ligations of DNA with the Quick Ligation Kit (Roche), and the polyacrylamide gel electrophoreses with the NuPAGE Novex System (Invitrogen). The enzyme linked immunosorbent assays (ELISA) were performed in 96 wells microtitration plates (Maxisorb, Nunc). The PBS buffer (phosphate buffer saline) was purchased from Invitrogen or Sigma-Aldrich; bovine serum albumin (BSA) from Roche; low-fat dry milk from Regilait; Tween 20, 4-nitrophenyl phosphate (pNPP) and 5-bromo-4-chloro-3-indolyl phosphate (Xp) from Sigma-Aldrich. Buffer A contained 50 mM Tris-HCl, pH 8.0, 500 mM NaCl; buffer B, 0.05% Tween in PBS; buffer C, 0.1% Tween in PBS; buffer D, 10% ethanolamine, pH 9.8, 0.01 M $MgSO_4$; and buffer E, 20 µM $ZnCl_2$ in buffer D.

Bacterial, Plasmid and Viral Strains

The XL1-Blue strain of E. coli (Bullock et al., 1987) and plasmids pET20b+ (www.novagen.com), pUC-4K (Genbank accession N° X06404) (Vieira and Messing, 1982), pCR-Blunt (Bernard et al., 1994), pQUANTAbody (Boulain and Ducancel, 2004), pLB11 (Lisova et al., 2007) and pVP5 (Lisova et al., 2007) have been described. Hypercompetent cells of XL1-Blue (Stratagene), pCR-Blunt (Invitrogen), pET20b+ (Novagen) and pUC-4K (Amersham Biosciences) were purchased from commercial suppliers. Plasmid pLIP5GN-H6 (H6 disclosed as SEQ ID NO: 32) is a derivative of pQUANTAbody (FIG. 1). The FGA/89 strain of serotype 1 of the dengue virus (DENV1; Genbank accession number AF226687) (Duarte dos Santos et al., 2000), the IS-98-ST1 strain of the West Nile virus (WNV; Genbank AF481864; (Malkinson et al., 2002)), the recombinant form $MV_{Schw}$ of the Schwarz strain of the measles virus, and its derivative $MV_{Schw}$-$sE_{WNV}$ (Despres et al., 2005) have been described. pUC-4K carries the aph gene, which confers resistance to kanamycin, in the form of a DNA cassette that is easily mobilisable. pQUANTAbody carries a mutant allele of the phoA gene from E. coli, under control of promoter ptac. This allele codes for an alkaline phosphatase (PhoA) with two mutations in its active site, D153G and D330N, and improved catalytic properties (Boulain and Ducancel, 2004; Le Du et al., 2002; Muller et al., 2001). pLIP5GN-H6 (H6 disclosed as SEQ ID NO: 32) differs from pQUANTAbody by the presence of six codons of histidine (H6) (SEQ ID NO: 32) and the multiple cloning site region, which are both located between codons 27 and 28 of phoA, downstream of the signal sequence (FIG. 1). pLB11 and pVP5 carry the gene segments that code for ED3.DEN1 and ED3.WN respectively between the NcoI and XhoI restriction sites of pET20b+ (FIG. 1). MVSchw-sEWNV expresses the soluble form of gpE from WNV.

Antibodies and Antiserums

The goat anti-human IgM and IgG (Sigma-Aldrich) were purchased from commercial suppliers. Human serums were from the collection of the National Center of Reference for Arboviruses, Institut Pasteur of French Guiana. They were collected from patients who displayed the basic clinical symptoms of dengue (fever, headache, myalgia, arthralgia), associated or not with rash and minor hemorrhagic manifestations. The serums were characterized with standard diagnosis methods, in particular GAC- and MAC-ELISAs using mouse-brain extracts as antigens.

The goat anti-mouse IgM (Pierce) and IgG (Sigma-Aldrich) were purchased from commercial suppliers. The mouse monoclonal antibody mAb4E11 has been described (Bedouelle et al., 2006). Its epitope at the surface of the ED3.DEN1 domain has been mapped; it is discontinuous and conformational (Lisova et al., 2007). A murine serum, directed against DENV1, was obtained by infection of BALB/c mice with the virus on day J0, challenge with the same virus on day J28, and bleeding on day J53. A control serum was obtained from non-infected mice of the same species. The titer in IgG of the positive serum, defined as below and measured by an indirect ELISA against domain ED3.DEN1, was equal to 30000 (Despres et al., 2005). A serum, directed against sE from WNV, was obtained by infection of CD46-IFNAR mice with the recombinant virus $MV_{Schw}$-$sE_{WNV}$ on day J0, and bleeding on day J8. A control serum was obtained by infection of mice with the "empty" virus $MV_{Schw}$. The titers in IgM of the positive and control serums were equal to 1000 and 100 respectively.

EXAMPLE 2

Construction of the Intermediate Vector pEBL1, Deposited at the CNCM (Collection Nationale de Culture de Microorganismes, 28 rue du Docteur Roux, 75015 PARIS) on Apr. 23, 2007 Under the Accession Number I-3747

The restriction sites that are located in the cloning region of plasmid pLIP5GN-H6, are very close and double restriction cuts in this region are difficult to monitor. Therefore a cassette of resistance to kanamycin was inserted in the SalI site of this region. Plasmid pUC-4K was digested with the SalI enzyme and the DNA fragment that contained the aph gene, was purified by agarose gel electrophoresis. pLIP5GN-H6 was also digested with SalI. The purified fragment and the linear vector were recombined by ligation. The recombinant plasmid, pEBL1 (SEQ ID NO:13), was recovered by transformation of the ligation mixture into competent cells of XL1-Blue and selection of the transformed cells on LB medium containing both ampicillin and kanamycin.

More precisely:

XL1-Blue(pEBL1)

XL1-Blue(pEBL1) is an *Escherichia coli* strain containing the pEBL1 plasmid. pEBL1 was engineered to simplify the construction of fusion proteins between an hexahistidine (SEQ ID NO: 32), a desired passenger protein (ED3 of flavivirus) and an alkaline phosphatase from *E. coli* with improved catalytic properties. In pEBL1, a DNA cassette which confers resistance to kanamycin is inserted at the position of the passenger gene. Thus the insertion of the passenger gene is easier to perform and to monitor, according to a cloning strategy previously described by Hermann et al., 1990.

Bacterial Strains and Plasmids Used for the Construction of XL1-Blue(pEBL1)

See Example 1.

Activities to be Checked Confirming the Viability of the Micro-Organism

The organism is resistant to ampicillin and kanamycin: this phenotype can be checked by plating the organism on Petri dishes containing LB Agar medium, 100 µg/ml Ampicillin and 50 µg/ml Kanamycin.

EXAMPLE 3

Construction of the ED3-PhoA Hybrid Genes

Methods

The ED3-phoA hybrid genes, coding for hybrid proteins between the ED3 domains of flaviviruses and PhoA, were constructed as follows. Plasmid pEBL1 (see Example 2) was first digested with the restriction enzyme SmaI, the completion of the digestion was verified by electrophoresis, and the digested DNA was desalted by size exclusion chromatography on a Microspin G25 column (Amersham-Biosciences). The linear form of pEBL1 was then digested with the SalI enzyme and the restriction cut was monitored by electrophoresis and the appearance of a DNA fragment that corresponded to the cassette of resistance to kanamycin (1252 bp). The ED3 gene was amplified by PCR with two oligonucleotide primers and the high fidelity polymerase Pfu-Turbo (Stratagene). The primer that hybridized at the 5'-end of the ED3 gene, brought in a SalI site and the primers that hybridized at the 3'-end, ScaI and SpeI sites. The ScaI site (AGTACT) was preferred to the SmaI site (CCC-GGG) because the latter introduced a rare codon CCC. The ScaI, SpeI and SalI sites were absent from the ED3.DEN1 and ED3. WN genes. The PCR products were digested with SalI and SalI. The digestion products were purified by electrophoresis through agarose gels and extraction, and then recombined by ligation. The recombinant plasmids were introduced into the XL1-Blue strain by transformation and the recombinant bacteria, screened for the formation of blue colonies on Xp indicator medium and sensitivity to kanamycine.

The primers that were used to amplify ED3.DEN1 from plasmid pLB11, had the following sequences, where the restriction sites are underlined:

```
                                         (SEQ ID NO: 14)
5'-GCCGGCGGTCGACAAAGGGATGTCATATGTGATGTGCAC-3';

(SEQ ID NO: 15)
5'-G TTTAGTACTAGTTTTCCCTATGCTGCT TCCCTT C-3'.
```

Similarly, the primers that were used to amplify ED3. WN, had the following sequences:

```
                                         (SEQ ID NO: 16)
5'-GCCGGCGGTCGACAAAGGAACAACCTATGGCGTCTG-3';

(SEQ ID NO: 17)
5'GGTGAGTACTAGTTTTGCCAATGCTGCT ACCAGAC-3'.
```

The sequences of the recombinant plasmids, pEBL11 coding for H6-ED3.DEN1-PhoA (H6 disclosed as SEQ ID NO: 32) and pEBL15 coding for H6-ED3.WN-PhoA (H6 disclosed as SEQ ID NO: 32), were checked with oligonucleotides that hybridized outside of the cloning region in pEBL1:

```
5'-GCACTGGCACTCTTACCGTTAC-3';    (SEQ ID NO: 18)

5'-CAGTCTGATCACCCGTTAAAC-3'.     (SEQ ID NO: 19)
```

EXAMPLE 4

Production and Purification of Bifunctional ED3-PhoA Hybrids

Production and Purification

The H6-ED3-PhoA hybrids (H6 disclosed as SEQ ID NO: 32) were produced from plasmids pEBL11 and pEBL15 in strain XL1-Blue. A pre-culture of the producing strain was obtained by inoculation of SB broth (1/10 volume) with an isolated colony and overnight incubation at 37° C. The production was obtained by dilution of the pre-culture in one volume of the same medium to obtain an initial absorbance $A_{600\ nm}$=0.25-0.30, growth at 30° C. until $A_{600\ nm}$=1.5-2.0, induction of promoter ptac with 0.2 mM IPTG, and further incubation for 2 h at the same temperature. All the subsequent steps were performed at 4° C. The culture was centrifuged 10 min at 5000 rpm. The bacterial pellet was resuspended in 5 mM imidazole, 1 mg/ml polymyxin B sulfate (Sigma-Aldrich) in buffer A (1/40 volume) and the bacterial suspension mildly agitated for 1 h with a magnetic stirrer. The periplasmic extract was collected by centrifugation of the suspension for 10 min at 13000 rpm and frozen at −20° C. The ED3-PhoA hybrid was purified from the periplasmic extract by affinity chromatography on a column of NiNTA resin (0.6 ml/L of culture, Qiagen). The column was loaded with the periplasmic extract and washed with 20 mM imidazole in buffer A (10 volumes of resin). The bound proteins were eluted with a step gradient of 40 to 100 mM imidazole in buffer A. The fractions of purifications were analyzed by SDS-PAGE (12% acrylamide) in reducing conditions. Those that contained H6-ED3-PhoA (H6 disclosed as SEQ ID NO: 32) and were pure at >90%, were pooled and transferred in PBS buffer by size exclusion chromatography on a P10 column (Amersham biosciences). They were snap-frozen at −80° C. either before or after transfer in PBS, indifferently in terms of functional properties (see Results). The concentrations of the purified H6-ED3-PhoA hybrids (H6 disclosed as SEQ ID NO: were determined by using $A_{280\ nm}$, and an extinction coefficient, $A_{280\ nm}$=40 680 $M^{-1}$ $cm^{-1}$ for the monomer, calculated from their amino acid sequences with the subroutine Pepstats of the software suite EMBOSS (Rice et al., 2000).

Indirect ELISA

The indirect ELISAs were performed in microtitration plates with volumes of 200 µL/well. Antibody mAb4E11 was diluted 10000-fold with PBS. Wells 1 to 11 of a plate were loaded with the antibody solution and well 12 with PBS alone, and the plate was incubated overnight at 4° C. for the reaction of adsorption. The wells were washed with buffer B (3 times), blocked with 3% BSA in buffer B for 3 h at 25° C., and washed again in buffer B (4 times). The H6-ED3.DEN1-PhoA hybrid (H6 disclosed as SEQ ID NO: 32) (0.2 µM initial concentration) was diluted twofold serially with 1% BSA in buffer B. Wells 1-10 were loaded with the 10 first dilutions of the hybrid, well 11 with the dilution buffer alone, and well 12 with the lowest dilution of the hybrid. The plate was incubated for 1 h at 25° C. for the reaction of capture. The wells were washed as above, and the captured hybrid was revealed by addition of 5 mM (2 mg/ml) pNPP in buffer D. The formation of para-nitrophenol was measured after overnight at 4°, using $A_{405\ nm}$.

Enzyme Activity

The formation of p-nitrophenolate (pNP) from pNPP was monitored at 25° C. in buffer D or E by $A_{405\ nm}$. The initial concentration of pNPP (5 mM) was saturating (Le Du et al., 2002) and therefore, the kinetic parameter $k_{cat}$ could be calculated through the equation:

$$dA_{405\ nm}/dt = k_{cat} E_0 \epsilon_{405nm}(pNP) \qquad (4)$$

where $dA_{405\ nm}/dt$ is the initial rate of formation of pNP; $E_0$, the total concentration of $(H6-ED3-PhoA)_2$ dimer (H6 disclosed as SEQ ID NO: 32); and $\epsilon_{405nm}(pNP)=1.78\times10^4$ $M^{-1}$ $cm^{-1}$ (Muller et al., 2001). The value of $k_{cat}$ was measured for several values of $E_0$ and averaged.

Functional Properties of the H6-ED3-PhoA Hybrids

To evaluate the functionality of the H6-ED3-PhoA hybrids (H6 disclosed as SEQ ID NO: 32), their phosphatase activity was measured and their recognition by monoclonal antibody mAb4E11 was assayed. The H6-ED3.DEN1-PhoA (H6 disclosed as SEQ ID NO: 32) and H6-ED3.WN-PhoA hybrids (H6 disclosed as SEQ ID NO: 32) were active for the dephosphorylation of pNPP into pNP, with $k_{cat}$ values in buffer D and 25° C. equal to 190±18 $s^{-1}$ and 154±6 $s^{-1}$ respectively for one molecule of dimer. H6-ED3.DEN1-PhoA (H6 disclosed as SEQ ID NO: 32) bound immobilized mAb4E11 specifically in an indirect ELISA which was revealed by its intrinsic phosphatase activity. These results showed that the PhoA portion of the hybrid was correctly folded and dimeric since the dimeric form of PhoA is 100 fold more active than its monomeric form (Boulanger and Kantrowitz, 2003). They showed that the ED3.DEN1 portion of the hybrid was correctly folded and functional as an antigen since the epitope of mAb4E11 is discontinuous, conformational and included within the ED3.DEN1 domain (Lisova et al., 2007). Because the antigenic property of each hybrid molecule was revealed with its intrinsic enzymatic activity, the results showed that a significant proportion of the H6-ED3.DEN1-PhoA molecules (H6 disclosed as SEQ ID NO: 32) had all the required properties simultaneously, i.e. their PhoA portion was dimeric and active, and their ED3.DEN1 portion was antigenic and in a bivalent state. The two residues in position 7 of the PhoA polypeptide chain are located on the same side in the structure of the PhoA dimer (Le Du et al., 2002). Therefore, the two copies of the ED3 portion in the H6-ED3-PhoA dimers (H6 disclosed as SEQ ID NO: 32) should also be on the same side of the molecule and able to interact with immunoglobulins according to an avidity mode. The above results were sufficient to indicate that the H6-ED3-PhoA hybrids (H6 disclosed as SEQ ID NO: 32) could be used in GAC- and MAC-ELISAs.

The existence of a recognition between H6-ED3.DEN1-PhoA (H6 disclosed as SEQ ID NO: 32) and antibody mAb4E11, whose epitope is discontinuous and conformational, was shown by an indirect ELISA, in which mAb4E11 was immobilized in the wells of a microtiter plate and the binding of the hybrid revealed by its alkaline phosphatase activity. This experiment showed that the two portions ED3.DEN1 and PhoA of each hybrid molecule were simultaneously functional. Therefore, these two portions were properly folded, their essential disulfide bonds had formed in the oxidizing medium of the periplasm, and their assembly was dimeric since PhoA is significantly active only in this oligomerization state. Each molecule of hybrid was dimeric and bifunctional.

The experiment of indirect ELISA showed that it was possible to detect recognition between the ED3.DEN1 domain and antibody mAb4E11 with $(H6-ED3.DEN1-PhoA)_2$ (H6 disclosed as SEQ ID NO: 32). This hybrid could be used to detect interactions between ED3 and other molecules, like inhibitors, other antibodies, receptors, or even whole cells.

The values of the catalytic constants $k_{cat}$ for H6-ED3.DEN1-PhoA (H6 disclosed as SEQ ID NO: 32) and H6-ED3.WN-PhoA (H6 disclosed as SEQ ID NO: 32) confirmed the high activity of the PhoA portion of these hybrid molecules and therefore their dimeric state. The artificial dimerisation of the recombinant ED3 domains through PhoA partially mimicked their multimeric presentation at the surface of the whole viruses and therefore their multivalent mode of interaction with antibodies or other receptors.

EXAMPLE 5

GAC- and MAC-ELISAs

Methods

The capture ELISAs were performed in microtitration plates with a volume of 100 µL/well. The anti-IgG and anti-IgM antibodies were diluted in PBS (final concentrations 1 µg/mL). Wells 1 to 11 of a plate were loaded with the solution of antibody and well 12 with PBS alone. The plate was incubated overnight at 4° C. for the reaction of adsorption. The next morning, the wells were washed with buffer C (3 times), blocked with 3% (w/v) dry milk in buffer C for 1 h at 37° C., and then washed with buffer C (3 times). The serum under analysis and the control serum were diluted 100 fold with 1% powder-milk in buffer C, then serially; the H6-ED3-PhoA hybrids (H6 disclosed as SEQ ID NO: 32) were diluted in the same buffer (0.5 µM final concentration of monomer). Wells 1-10 were loaded with the 10 first dilutions of the serum, well 11 with the dilution buffer alone, and well 12 with the lowest dilution of the serum. The plate was incubated for 1 h at 37° C. for the reaction of antibody capture. The wells were washed with buffer C (3 times) and then loaded with the solution of H6-ED3-PhoA (H6 disclosed as SEQ ID NO: 32). The plate was incubated for 1 h at 37° C. for the binding reaction. The wells were washed as above and the bound H6-ED3-PhoA molecules (H6 disclosed as SEQ ID NO: 32) revealed by addition of 5 mM pNPP in buffer E. $A_{405\ nm}$ was measured either after a few hours at 25° C. or overnight at 4° C. The signal of the serum was considered as significant if its value was at least twice that of the blank controls. The titer of the serum was equal to the maximum dilution factor for which the signal remained significant. The capture ELISAs were performed for the murine serums as for the human serums, except that some washes were extended, the anti-IgM antibody was used at 2.4 μg/mL final concentration, H6-ED3.DEN1-PhoA (H6 disclosed as SEQ ID NO: 32) at 0.2 μM final concentration of monomer, and pNPP in buffer D.

Results

A Simplified GAC-ELISA for the Quantification of Anti-Flaviviral IgGs

It was tested if an H6-ED3-PhoA hybrid (H6 disclosed as SEQ ID NO: 32) could detect IgGs, directed against the cognate flavivirus, in the serum of an immunized mouse and thus simplify the protocol of GAC-ELISA which is generally used for such a serology. Therefore, an antibody, directed against the murine IgGs, was immobilized in the wells of a microtitration plate by passive adsorption on the plastics. This immobilized antibody was used to capture the IgGs that were present in the mouse serum. The IgGs that were directed against the ED3 domain, were revealed with the H6-ED3-PhoA hybrid (H6 disclosed as SEQ ID NO: 32), through the binding of its antigenic portion and the catalytic activity of its PhoA portion (Equation 3).

This assay was performed with the serum of a mouse that had been immunized with DENV1. The serum of a non-immunized mouse, a blank test without anti-IgG antibody, and blank tests without serum were used as controls (Materials and Methods). The formation of pNP from pNPP, catalyzed by the H6-ED3.DEN1-PhoA (H6 disclosed as SEQ ID NO: 32) hybrid and monitored with $A_{405\ nm}$, was used as a signal to reveal the binding reaction (FIG. 2). The $A_{405\ nm}$ signal followed a low of saturation as a function of the concentration in immune serum. The titer of the immune serum was >50000 after an overnight revelation (>12500 after 2.5 h) in these experiments that were repeated three times independently. The $A_{405\ nm}$ signal for the non-immune serum did not differ from the blank signal whereas the signal for the immune serum was 2 to 18 fold higher than the blank signal, depending on the concentration, after an overnight revelation (2 to 6 fold after 2.5 h). These results confirmed that both portions of H6-ED3.DEN1-PhoA (H6 disclosed as SEQ ID NO: 32) were simultaneously functional in one molecule of hybrid. They showed that this hybrid could sensitively, quantitatively and specifically assay the presence of IgGs, directed against the ED3.DEN1 domain, in a serum and thus detect an infection by the dengue virus.

A Simplified MAC-ELISA for the Quantification of Anti-Flaviviral IgMs

Similarly, it was tested if a H6-ED3-PhoA hybrid (H6 disclosed as SEQ ID NO: 32) could detect IgMs, directed against a flavivirus, in the serum of an immunized mouse and thus simplify the protocol of MAC-ELISA which is generally used. An antibody, directed against the murine IgMs, was immobilized. This immobilized antibody was used to capture the IgMs that were present in the mouse serum. The IgMs that were directed against the ED3 domain, were revealed with the bivalent H6-ED3-PhoA hybrid (Equation 3) (H6 disclosed as SEQ ID NO: 32).

This assay was performed with the serum of a mouse that had been immunized with the chimeric virus $MV_{Schw}$-$sE_{WNV}$, which expresses the secreted form of gpE from WNV. The serum of a mouse that had been immunized with the empty vector $MV_{Schw}$, a blank test without anti-IgM antibody, and blank tests without sera were used as controls (Materials and Methods). The H6-ED3.WN-PhoA hybrid (H6 disclosed as SEQ ID NO: 32) was used to reveal the binding reactions (FIG. 3). The $A_{405\ nm}$ signal followed a low of saturation as a function of the concentration in immune serum. The titer of the immune serum was >800 after an overnight revelation (>400 after 3 h). The $A_{405\ nm}$ signal for the non-immune serum was at most 1.7 fold higher than the blank signal after an overnight incubation whereas the signal for the immune serum was 2 to 6.4 fold higher than the blank signal, depending on the concentration. These figures were 1.2 fold for the non-immune serum and 2 to 2.6 fold for the immune serum after a revelation of 3 h. Note that the signal for the non-immune serum did not differ significantly from the blank signal for relative concentrations of serum ≦0.5%. These results confirmed that both portions of H6-ED3.WN-PhoA (H6 disclosed as SEQ ID NO: 32) were simultaneously functional in one molecule of hybrid. They showed that this hybrid could sensitively, quantitatively and specifically assay the presence of IgMs, directed against the ED3.WN domain. They suggested that the hybrid could enable one to detect an exposure to WNV precociously (at day 8).

EXAMPLE 6

Discrimination Between Flaviviruses by the ED3-PhoA Hybrids

The specificity of the simplified GAC- and MAC-ELISA according to the invention was tested by performing cross-reactions. The serum of the mouse that had been immunized with the DENV1 virus, was submitted to two parallel GAC-ELISAs that were revealed with either the H6-ED3.DEN1-PhoA hybrid (H6 disclosed as SEQ ID NO: 32) or with H6-ED3.WN-PhoA (FIG. 4) (H6 disclosed as SEQ ID NO: 32). Reciproquely, the serum of the mouse that had been immunized with the $MV_{Schw}$-$sE_{WNV}$ chimeric virus, was submitted to two parallel MAC-ELISAs that were revealed with either the H6-ED3.DEN1-PhoA hybrid (H6 disclosed as SEQ ID NO: 32) or with H6-ED3.WN-PhoA (FIG. 5) (H6 disclosed as SEQ ID NO: 32). After an overnight revelation, the cognate signal was up to 5.4 fold higher than the non-cognate signal in the GAC-ELISA, and up to 3.9 fold higher in the MAC-ELISA. Of course, these figures were much higher when the specific signals (signal of the serum minus signal of the blank) were considered. These results showed that the GAC- and MAC-ELISA, as described here, were specific and that they allowed one to determine the identity of the flavivirus that was involved in the infection or immunization.

EXAMPLE 7

Assay of Human Serums With the Simplified GAC- and MAC-ELISA

The H6-ED3.DEN1-PhoA hybrid (H6 disclosed as SEQ ID NO: 32) was used to test serums from human patients who had been infected with one of the four serotypes DENV1 to DENV4 of the dengue virus. For DENV1, three serum samples, taken between days 9 and 28 after the onset of the symptoms, corresponded to primary infections with the dengue virus; two serum samples, taken at days 13 and 18, corresponded to secondary infections. For DENV2, -3 and -4, the samples were taken between days 8 and 32, and the primary or secondary status of the infection was unknown. These serums had been previously assayed by standard methods of GAC- and MAC-ELISA, with suckling mouse brain extracts as antigens. The following controls were used: an assay in which the immobilized antibody, directed against human IgG or IgM, was omitted; an assay in which the serum was omitted; and two assays with serums of patients who had not been infected by the dengue virus.

The $A_{405\ nm}$ signal followed a law of saturation as a function of the concentration in serum, for the serums from patients with primary DENV1 infections in the MAC-ELISA (FIG. 6) and for the serums from patients with secondary DENV1 infections in the GAC-ELISA (not shown). It increased linearly up to a relative concentration of serum >2.5‰. Therefore, this relative concentration was used for the following of the analysis. A revelation of the assays during 3 h at 25° C. was sufficient.

Among the 20 tested serums, only the three serums that corresponded to primary infections, gave signals that were positive in the MAC-ELISA, i.e. more than twice the signal of the controls; all the other serums gave signals that were identical to the controls (FIG. 7A). Therefore, the simplified MAC-ELISA according to the invention could detect a primary infection with DENV1, and distinguish between infections with DENV1 and the other three serotypes. Four serum samples gave positive signals in the GAC-ELISA: the two samples from patients with a secondary DENV1 infection; one sample (2d) among the six samples from patients with a DENV2 infection; and one sample (4a) among the two samples from patients with a DENV4 infection (FIG. 7B). Therefore, the simplified GAC-ELISA according to the invention could detect a secondary infection with DENV1 at day 13 after the onset of symptoms. The patients whose serums 2d and 4a scored as positive in the simplified GAC-ELISA, might have experienced an unnoticed infection with DENV1 previously. No correlation was observed between the day at which each sample was taken and the value of the signal in the simplified MAC- and GAC-ELISAs.

The ratio r of the signals in parallel MAC- and GAC-ELISAs has been used to determine whether an infection by the dengue virus is of the primary or secondary type. Such a ratio for the signals in the simplified capture ELISAs according to the invention (FIG. 7C) was calculated. The three serums that corresponded to primary infections by DENV1, had r>1.90. All the serums that corresponded to infections by DENV2, -3 and -4, had r<1.4, except serums 2d and 4a. The serums that corresponded to secondary infections by DENV1, and serums 2d and 4a had r<0.4. Thus, the ratio r could distinguish between primary and secondary infections, and also between primary infections with DENV1 and infections with other DENV serotypes.

The (H6-ED3.DEN1-PhoA)$_2$ hybrid (H6 disclosed as SEQ ID NO: 32) was used successfully in a simplified GAC-ELISA to reveal the presence of IgGs, directed against DENV1, in the serum of a mouse that had been hyper-immunized against this virus, or in the serums of human patients who had endured a secondary infection by this virus. The same hybrid was used successfully in a simplified MAC-ELISA to reveal the presence of IgMs, directed against DENV1, in the serums of patients who had endured a primary infection by this virus. The simplified GAC-ELISA enabled us to distinguish between infection by DENV1 and WNV in the mouse. The combination of the simplified GAC- and MAC-ELISAs enabled us to distinguish between an infection by DENV1 and an infection by the three other serotypes of DENV in man, and also between a primary and a secondary infection by DENV1.

Likewise, the (H6-ED3.WN-PhoA)$_2$ hybrid (H6 disclosed as SEQ ID NO: 32) was used successfully in a simplified MAC-ELISA to reveal the presence of IgMs, directed against WNV in the serum of a mouse. This simplified MAC-ELISA enabled us to distinguish between infections by WNV and DENV1. The high specificity and sensitivity of the simplified GAC- and MAC-ELISAs came likely from two factors: the use of the ED3 domain as an antigen and the independence of the detection system, consisting of the fusion with PhoA, towards the nature of the antigen and its interactions with the immunoglobulins of the serum. The specificity of the (H6-ED3-PhoA)$_2$ (H6 disclosed as SEQ ID NO: 32) bifunctional dimers should be higher than those of the antigens and detection systems that have been used up until now.

EXAMPLE 8

Assay of Human Serums With a Simplified MAC-ELISA

In a further series of experiments serums of patients infected by one of the four serotypes DEN1 to DEN4 of the dengue virus or by the yellow fever virus (YFV) were collected and characterized by standard methods of MAC-ELISA (Talarmin et al., 1998) and PCR (Lanciotti et al., 1992). The standard MAC-ELISA used extracts of infected suckling mouse brains as antigens and the PCR used primers that were specific for each viral serotype (Table I). The primer sequences and amplification conditions were as described (Lanciotti et al., 1992). In particular the primer sequences were as follows: Primer D1: 5'-TCAATATGCT-GAAACGCGCGAGAAACCG-3' (SEQ ID NO: 26). Primer D2: 5'-TTGCACCAACAGTCAATGTCTTCAGGTTC-3' (SEQ ID NO: 27). Primer TS1: 5'-CGTCTCAGTGATC-CGGGGG-3' (SEQ ID NO: 28). Primer TS2: 5'-CGCCA-CAAGGGGCATGAACAG-3' (SEQ ID NO: 29). Primer TS3: 5'-TAACATCATCATGAGACAGAGC-3' (SEQ ID NO: 30). Primer TS4: 5'-CTC TGT TGT CTT AAA CAA GAG A-3' (SEQ ID NO: 31).

Amplification occurred in 100 µl volumes containing the following components: 50 mM KCl, 10 mM Tris (pH 8.5), 1.5 mM MgCl$_2$, 0.01% gelatin, 200 µM each of the four deoxynucleotide triphosphates, 5 mM dithiothreitol, 50 pmol each of primer, 2.5 Units of rav-2 recombinant RT (Amersham, Arlington Heights, Ill.) and 2.5 Units of Amplitaq polymerase (Perkin Elmer, Norwalk, Conn.). The reactions were allowed to proceed in a thermocycler programmed to incubate for 1 h at 42° C. and then to proceed with 35 cycles of denaturation (94° C., 30 s), primer annealing (55° C., 1 min) and primer extension (72° C., 2 min).

TABLE I

Number of human serums analyzed by simplified MAC and GAC-ELISAs.

| Serum | ELISA | DEN hybrids | YF hybrid |
|---|---|---|---|
| DEN1 | MAC | 30 | 18 |
| DEN2 | MAC | 44 | 24 |
| DEN3 | MAC | 38 | 18 |
| DEN4 | MAC | 13 | 13 |
| YF | MAC | 19 | 19 |
| DEN1 | GAC | 18 | 0 |
| DEN2 | GAC | 24 | 0 |
| DEN3 | GAC | 18 | 0 |

In said Table I, Column 1: flavivirus detected in the serum of human patients by standard diagnostic methods (see text). Column 3: number of serums tested in parallel with the H6-ED3-PhoA hybrids corresponding to the four serotypes of DENV. Column 4: number of serums tested in parallel with the four H6-ED3.DEN-PhoA hybrids (H6 disclosed as SEQ ID NO: 32) and the H6-ED3.YF-PhoA hybrid (H6 disclosed as SEQ ID NO: 32). The serums in column 4 constituted a sub-set of the serums in column 3.

Four among the 19 serums of patients that were infected with YFV, came from the Institut Pasteur of Cayenne (French Guyana) and corresponded to patients that had been recently vaccinated against YFV, and the remaining 15 serums came from the Institut Pasteur of Dakar (Senegal).

The collected serums were assayed by the simplified MAC-ELISA according to the present invention, with the five corresponding H6-ED3-PhoA hybrids (H6 disclosed as SEQ ID NO: 32) and as previously described (see Example 5). The general format of the simplified MAC-ELISA is the following:

Support-anti-huIgM::serum::(H6-ED3-PhoA)$_2$(H6 disclosed as SEQ ID NO: 32)

where anti-huIgM is an antibody directed against the human IgMs. The inventors considered the signal A of a serum assay to be positive, when it was higher than twice the signal $A_c$ of the control, i. e. $A>2A_c$. The latter consisted in an assay which was performed in n-plicates ($n\geq 3$) and in which the antibody directed against the human IgMs, was omitted.

Table II gives the proportion of positive signals for each type of serum and hybrid. For each type of serum, the proportion of positive signals was maximal for the cognate hybrid, except for the serums of patients that were infected by DENV4. In this last case, the proportion of positive signals was maximal with the ED3.DEN1-PhoA and ED3.DEN2-PhoA hybrids. The DEN2 and YF serums reacted rarely with non-cognate hybrids. In contrast, the DEN1 serums reacted often with the DEN2 and DEN3 hybrids, and the DEN4 serums with every DEN hybrid. Conversely, for each type of hybrid, the proportion of positive signals was maximal with the cognate serums, except for ED3.DEN4-PhoA which reacted weakly with every kind of serum. In particular, the DEN1 and YF hybrids reacted rarely with the non-cognate serums.

TABLE II

Analysis of human serums by a simplified MAC-ELISA, using H6-ED3-PhoA hybrids (H6 disclosed as SEQ ID NO: 32).

| | Proportion of positive serums (%) | | | | |
|---|---|---|---|---|---|
| Hybrid | DEN1 | DEN2 | DEN3 | DEN4 | YF |
| DEN1 | 83 | 11 | 16 | 23 | 0 |
| DEN2 | 63 | 73 | 26 | 23 | 4 |
| DEN3 | 37 | 9 | 47 | 15 | 17 |
| DEN4 | 3 | 7 | 3 | 8 | 15 |
| YF | 0 | 5 | 0 | 0 | 47 |

In said Table II, Column 1 gives the type of the H6-ED3-PhoA hybrid (H6 disclosed as SEQ ID NO: 32) used in the assay, i.e. the viral origin of its ED3 portion. Columns 2-6 give the proportion of positive serums in the assay for each type of serum and hybrid. The signal A of a serum was considered as positive if higher than twice the control signal $A_c$ ($A\geq 2A_c$) and negative if lower ($A<2A_c$). The number and properties of the human serums are given in Table I.

Table III gives the mean value of the ratio (serum signal)/(control signal) for each type of serum and each type of hybrid, i. e. $<A/A_c>$. For each type of serum, this mean value was maximal for the cognate hybrid, except for the DEN4 serums. However, for each type of hybrid this mean value was not maximal for the cognate serum, in general.

TABLE III

Relative signals of human serums in simplified MAC-ELISAs.

| | Relative signal for serums | | | | |
|---|---|---|---|---|---|
| Hybrid | DEN1 | DEN2 | DEN3 | DEN4 | YF |
| DEN1 | 10.0 | 1.9 | 1.4 | 1.9 | 1.3 |
| DEN2 | 5.3 | 5.0 | 2.0 | 1.8 | 1.4 |
| DEN3 | 3.0 | 2.0 | 2.6 | 1.4 | 1.6 |
| DEN4 | 1.3 | 1.6 | 1.2 | 1.3 | 1.7 |
| YF | 1.4 | 1.4 | 1.6 | 1.7 | 2.5 |

In said Table III, Column 1 gives the type of H6-ED3-PhoA hybrid (H6 disclosed as SEQ ID NO: 32) used in the assay. Columns 2-6 give the mean value of $A/A_c$ for each type of serum and hybrid. See legend to Table II for details.

EXAMPLE 9

Sensitivity and Specificity of the Simplified MAC-ELISA, Using Threshold Signals The sensitivity of the simplified MAC-ELISA is given in row 1 of Table IV, for each type of serum and cognate hybrid. This sensitivity was high for the DEN1 and DEN2 serums, medium for the DEN3 and YF serums, and low for the DEN4 serums. If one restricts itself to the four YF serums that came from the Institut Pasteur of Cayenne and corresponded to vaccinated patients, the sensitivity was much higher (four positive signals). The ED3.YF-PhoA hybrid, whose sequence corresponded to the vaccinal strain 17D of YFV, might detect the IgM that are directed against the vaccinal virus better that those that are directed against wild type strains.

TABLE IV

Sensitivity and specificities of the simplified MAC-ELISAs for human serums.

| | | Detection of | | | | |
|---|---|---|---|---|---|---|
| Property | Param | DEN1 | DEN2 | DEN3 | DEN4 | YF |
| Sensitivity (%) | $2\times A_c$ | 83 | 73 | 47 | 8 | 47 |
| Serotype specificity (%) | $2\times A_c$ | 20 | 78 | 50 | 0 | na |
| Serotype specificity (%) | $A_{max}$ | 100 | 97 | 89 | 0 | na |
| Group specificity (%) | $2\times A_c$ | 100 | 94 | 89 | 100 | 89 |
| Viral specificity (%) | $A_{max}$ | 100 | 100 | 89 | 0 | 89 |

In Table IV, sensitivity in row 1 was defined as the proportion of serums that gave a positive signal when assayed with the cognate H6-ED3-PhoA hybrid (H6 disclosed as SEQ ID NO: 32) (see diagonal in Table II). DEN serotype specificity in row 2 was defined as the proportion of serums that gave negative signals with the three non-cognate DEN hybrids, among those that gave a positive signal with the cognate DEN hybrid. DEN serotype specificity in row 3 was defined as the proportion of serums that gave a higher signal with the cognate DEN hybrid than with the three non-cognate DEN hybrids, among those that gave a positive signal with the cognate hybrid. The DEN serotype specificities in rows 2 and 3 were determined with the serums of Table I, column 3. Group specificity in row 4 was defined as the proportion of DEN serums that gave a positive signal with the cognate DEN hybrid and a negative signal with the YF hybrid; and as the proportion of YF serums that gave a positive signal with the cognate YF hybrid and a negative signal with all four DEN hybrids. Viral specificity in row 5 was defined as the proportion of serums that gave a higher signal with the cognate hybrid than with the non-cognate ones, among those that gave a positive signal with their cognate hybrid. The group and viral specificities in rows 4 and 5 were determined with the serums of Table I column 4. See Table II for other details.

The specificity of the ED3-PhoA hybrids for a DEN serotype in the simplified MAC-ELISAs was calculated as the proportion of serums that gave negative signals with the three non-cognate hybrids ($A<2A_c$), among serums that gave a positive signal with the cognate hybrid ($A>2A_c$). This specificity of serotype was high for the ED3.DEN2-PhoA hybrid, medium for the DEN3 hybrid, low for the DEN1 hybrid and nil for the DEN4 hybrid (Table IV, row 2).

The specificity of the ED3-PhoA hybrids for a viral group in the simplified MAC-ELISAs was calculated on the one hand as the proportion of DEN serums that gave a positive signal with the cognate ED3.DEN-PhoA hybrid and a negative signal with the ED3.YF-PhoA hybrid; and on the other hand as the proportion of YF serums that gave a positive signal with the cognate ED3.YF-PhoA hybrid and a negative signal with all the ED3.DEN-PhoA hybrids. This specificity for a viral group was ≧89% in every case and up to 100% for the ED3.DEN1-PhoA and ED3.DEN4-PhoA hybrids (Table IV, row 4).

EXAMPLE 10

Specificity of the Simplified MAC-ELISA, Using the Maximal Signals

The modular structure of the ED3-PhoA hybrids is such that the intensity of the signal in a simplified MAC-ELISA depends only on the properties of recognition between its ED3 portion and the antibodies of the serum. This property enables one to quantitatively compare the signals obtained for a given serum with ED3-PhoA hybrids that carry different ED3 domains. Therefore, the inventors calculated the proportion of serums that gave a positive signal with the cognate ED3-PhoA hybrid, and a higher signal with the cognate hybrid than with the non-cognate ones. The inventors calculated these proportions for the four ED3.DEN hybrids and then for the five ED3-PhoA hybrids. The serotype specificity, calculated in this way for the four DEN hybrids, was ≧89% for the DEN1, DEN2 and DEN3 hybrids, and nil with the DEN4 hybrid (Table IV, row 3). The viral specificity, calculated for the five hybrids, was also ≧89% except for the DEN4 hybrid (Table IV, row 5).

EXAMPLE 11

Assay of Human Serums with a Simplified GAC-ELISA

Serums of patients infected by one of the three serotypes DEN1, DEN2 and DEN3 of the dengue virus were collected and characterized by standard methods of IgG-specific indirect ELISA and PCR. The indirect ELISA used extracts of infected suckling mouse brains as antigens, and the PCR used primers that were specific for each viral serotype (Table I). The collected serums were assayed by the simplified GAC-ELISA according to the present invention, with the three corresponding H6-ED3-PhoA hybrids (H6 disclosed as SEQ ID NO: 32), as previously described (see Example 5). The general format of the simplified GAC-ELISA is the following:

Support-anti-huIgG::serum::(H6-ED3-PhoA)$_2$(H6 disclosed as SEQ ID NO: 32)

where anti-huIgG is an antibody directed against the human IgGs. The inventors considered that the signal of a serum assay was positive when it was higher than twice the signal of the control. The latter consisted in an assay which was performed in n-plicates (n≧3) and in which the antibody directed against the human IgGs, was omitted. The proportion of positive serums in a simplified GAC-ELISA, performed with the cognate hybrid, was low and at most 29% (Table V).

TABLE V

Sensitivity and specificities of the simplified GAC-ELISAs for human serums.

| | | Detection of | | |
|---|---|---|---|---|
| Property | Param | DEN1 | DEN2 | DEN3 |
| Sensitivity (%) | $2xA_c$ | 28 | 29 | 17 |
| Serotype specificity (%) | $2xA_c$ | 60 | 0 | 0 |
| Serotype specificity (%) | $A_{max}$ | 100 | 29 | 33 |

In Table V, the sensitivity and serotype specificity were defined as in Table IV. The number and properties of the human serums are given in Table I.

The H6-ED3-PhoA hybrids (H6 disclosed as SEQ ID NO: 32) characterised in examples 8-11, have enabled the inventors to recognize recent infections by the dengue viruses or the yellow fever virus precociously, by a simplified MAC-ELISA. The sensitivities were going from high to very high except for the DEN4 virus, in the order DEN1>DEN2>DEN3=YF>>DEN4.

These differences in sensitivity could be due to variable levels of immunogenicity of the ED3 domains, according to the virus. Under this assumption, the ED3.DEN4 domain could be less immunogenic than the ED3 domains from the three other serotypes DEN1-DEN3 or from YFV. Alternatively, the differences in sensitivity could be due to the specific strains, and therefore sequences, of viruses that the inventors used to construct the recombinant hybrids. For example, the simplified MAC-ELISA for the infection by YFV could be improved by having two hybrids at one's disposal, one corresponding to the 17D vaccine strain and the other one to a wild type strain.

The five tested hybrids had a very good specificity of viral group, i. e. dengue group versus yellow fever group, higher than 89%. They also had a very good specificity of serotype, higher than 89% except for the DEN4 hybrid, when assays of a same serum with different hybrids were compared quantitatively. The results suggested that the antibodies directed against ED3.DEN4 recognize epitopes that are shared between flaviviruses.

The simplified GAC-ELISA, performed on human serums with serotypes DEN1-DEN3 of the H6-ED3-PhoA hybrids (H6 disclosed as SEQ ID NO: 32), had low sensitivities. Whether this conclusion is general and should be extended to other viruses or organisms, remains to be determined. FIGS. 2 and 4 show the sensitivities for a simplified GAC-ELISA that was performed with the H6-ED3.DEN1-PhoA hybrid (H6 disclosed as SEQ ID NO: 32) on serums from mice that had been immunized with DENV1. The inventors have also shown that a quantitative comparison of the signals in simplified MAC- and GAC-ELISAs performed on human serums and that this could distinguish between primary and secondary infections by DENV1, see Example 7 and FIG. 7.

Thus, the recombinant H6-ED3-PhoA hybrids (H6 disclosed as SEQ ID NO: 32) can be prepared easily in low safety laboratories. They enable the detection of infections by flaviviruses precociously and allow clinicians to distinguish between groups of viruses or even between serotypes of the dengue virus.

REFERENCES

Alcon, S., Talarmin, A., Debruyne, M., Falconar, A., Deubel, V., and Flamand, M. (2002). Enzyme-linked immunosorbent assay specific to Dengue virus type 1 nonstructural protein NS1 reveals circulation of the antigen in the blood during the acute phase of disease in patients experiencing primary or secondary infections. J Clin Microbiol 40, 376-381.

AnandaRao, R., Swaminathan, S., Fernando, S., Jana, A. M., and Khanna, N. (2005). A custom-designed recombinant multiepitope protein as a dengue diagnostic reagent. Protein Expr Purif 41, 136-147.

Beasley, D. W., Holbrook, M. R., Travassos Da Rosa, A. P., Coffey, L., Carrara, A. S., Phillippi-Falkenstein, K., Bohm, R. P., Jr., Ratterree, M. S., Lillibridge, K. M., Ludwig, G. V., et al. (2004). Use of a recombinant envelope protein subunit antigen for specific serological diagnosis of West Nile virus infection. J Clin Microbiol 42, 2759-2765.

Bedouelle, H., Belkadi, L., England, P., Guijarro, J. I., Lisova, O., Urvoas, A., Delepierre, M., and Thullier, P. (2006). Diversity and junction residues as hotspots of binding energy in an antibody neutralizing the dengue virus. Febs J 273, 34-46.

Bernard, P., Gabant, P., Bahassi, E. M., and Couturier, M. (1994). Positive-selection vectors using the F plasmid ccdB killer gene. Gene 148, 71-74.

Blitvich, B. J., Marlenee, N. L., Hall, R. A., Calisher, C. H., Bowen, R. A., Roehrig, J. T., Komar, N., Langevin, S. A., and Beaty, B. J. (2003). Epitope-blocking enzyme-linked immunosorbent assays for the detection of serum antibodies to west nile virus in multiple avian species. J Clin Microbiol 41, 1041-1047.

Boulain, J. C., and Ducancel, F. (2004). Expression of recombinant alkaline phosphatase conjugates in *Escherichia coli*. Methods Mol Biol 267, 101-112.

Boulanger, R. R., Jr., and Kantrowitz, E. R. (2003). Characterization of a monomeric *Escherichia coli* alkaline phosphatase formed upon a single amino acid substitution. J Biol Chem 278, 23497-23501.

Bullock, W. O., Fernandez, J. M., and Short, J. M. (1987). XL1-Blue: a high efficiency plasmid transforming recA *Escherichia coli* strain with beta-galactosidase selection. BioTechniques 5, 376-379.

Cardosa, M. J., Tio, P. H., Nimmannitya, S., Nisalak, A., and Innis, B. (1992). IgM capture ELISA for detection of IgM antibodies to dengue virus: comparison of 2 formats using hemagglutinins and cell culture derived antigens. Southeast Asian J Trop Med Public Health 23, 726-729.

Crill, W. D., and Chang, G. J. (2004). Localization and characterization of flavivirus envelope glycoprotein cross-reactive epitopes. J Virol 78, 13975-13986.

Crill, W. D., and Roehrig, J. T. (2001). Monoclonal antibodies that bind to domain III of dengue virus E glycoprotein are the most efficient blockers of virus adsorption to Vero cells. J Virol 75, 7769-7773.

Cuzzubbo, A. J., Endy, T. P., Nisalak, A., Kalayanarooj, S., Vaughn, D. W., Ogata, S. A., Clements, D. E., and Devine, P. L. (2001). Use of recombinant envelope proteins for serological diagnosis of Dengue virus infection in an immunochromatographic assay. Clin Diagn Lab Immunol 8, 1150-1155.

Despres, P., Combredet, C., Frenkiel, M. P., Lorin, C., Brahic, M., and Tangy, F. (2005). Live measles vaccine expressing the secreted form of the West Nile virus envelope glycoprotein protects against West Nile virus encephalitis. J Infect Dis 191, 207-214.

Duarte dos Santos, C. N., Frenkiel, M. P., Courageot, M. P., Rocha, C. F., Vazeille-Falcoz, M. C., Wien, M. W., Rey, F. A., Deubel, V., and Despres, P. (2000). Determinants in the envelope E protein and viral RNA helicase NS3 that influence the induction of apoptosis in response to infection with dengue type 1 virus. Virology 274, 292-308.

Ferlenghi, I., Clarke, M., Ruttan, T., Allison, S. L., Schalich, J., Heinz, F. X., Harrison, S. C., Rey, F. A., and Fuller, S. D. (2001). Molecular organization of a recombinant subviral particle from tick-borne encephalitis virus. Mol Cell 7, 593-602.

Granwehr, B. P., Lillibridge, K. M., Higgs, S., Mason, P. W., Aronson, J. F., Campbell, G. A., and Barrett, A. D. (2004). West Nile virus: where are we now? Lancet Infect Dis 4, 547-556.

Gritsun, T. S., Holmes, E. C., and Gould, E. A. (1995). Analysis of flavivirus envelope proteins reveals variable domains that reflect their antigenicity and may determine their pathogenesis. Virus Res 35, 307-321.

Halstead, S. B. (2003). Neutralization and antibody-dependent enhancement of dengue viruses. Adv Virus Res 60, 421-467.

Hermann, M., and Bedouelle, H. (1990). A method for monitoring double restriction cuts within a polylinker. Res Microbiol 141, 187-189.

Hogrefe, W. R., Moore, R., Lape-Nixon, M., Wagner, M., and Prince, H. E. (2004). Performance of immunoglobulin G (IgG) and IgM enzyme-linked immunosorbent assays using a West Nile virus recombinant antigen (preM/E) for detection of West Nile virus- and other flavivirus-specific antibodies. J Clin Microbiol 42, 4641-4648.

Holbrook, M. R., Shope, R. E., and Barrett, A. D. (2004). Use of recombinant E protein domain III-based enzyme-linked immunosorbent assays for differentiation of tick-borne encephalitis serocomplex flaviviruses from mosquito-borne flaviviruses. J Clin Microbiol 42, 4101-4110.

Holmes, D. A., Purdy, D. E., Chao, D. Y., Noga, A. J., and Chang, G. J. (2005). Comparative analysis of immunoglobulin M (IgM) capture enzyme-linked immunosorbent assay using virus-like particles or virus-infected mouse brain antigens to detect IgM antibody in sera from patients with evident flaviviral infections. J Clin Microbiol 43, 3227-3236.

Innis, B. L., Nisalak, A., Nimmannitya, S., Kusalerdchariya, S., Chongswasdi, V., Suntayakorn, S., Puttisri, P., and Hoke, C. H. (1989). An enzyme-linked immunosorbent assay to characterize dengue infections where dengue and Japanese encephalitis co-circulate. Am J Trop Med Hyg 40, 418-427.

Johnson, A. J., Martin, D. A., Karabatsos, N., and Roehrig, J. T. (2000). Detection of anti-arboviral immunoglobulin G by using a monoclonal antibody-based capture enzyme-linked immunosorbent assay. J Clin Microbiol 38, 1827-1831.

Kanai, R., Kar, K., Anthony, K., Gould, L. H., Ledizet, M., Fikrig, E., Marasco, W. A., Koski, R. A., and Modis, Y. (2006). Crystal structure of west nile virus envelope glycoprotein reveals viral surface epitopes. J Virol 80, 11000-11008.

Kao, C. L., King, C. C., Chao, D. Y., Wu, H. L., and Chang, G. J. (2005). Laboratory diagnosis of dengue virus infection: current and future perspectives in clinical diagnosis and public health. J Microbiol Immunol Infect 38, 5-16.

Kerschbaumer, R. J., Hirschl, S., Schwager, C., Ibl, M., and Himmler, G. (1996) pDAP2: a vector for construction of alkaline phosphatase fusion proteins. Immunotechnology Volume 2, Issue 2, June, Pages 145-150

Kuhn, R. J., Zhang, W., Rossmann, M. G., Pletnev, S. V., Corver, J., Lenches, E., Jones, C. T., Mukhopadhyay, S., Chipman, P. R., Strauss, E. G., et al. (2002). Structure of dengue virus: implications for flavivirus organization, maturation, and fusion. Cell 108, 717-725.

Kuno, G. (2003). Serodiagnosis of flaviviral infections and vaccinations in humans. Adv Virus Res 61, 3-65.

Lanciotti, R. S., Calisher, C. H., Gubler, D. J, Chang, G. J., Vorndam, A. V. (1992). Rapid detection and typing of dengue viruses from clinical samples by using reverse transcriptase polymerase chain reaction. J Clin Microbiol 30, 545-551.

Le Du, M. H., Lamoure, C., Muller, B. H., Bulgakov, O. V., Lajeunesse, E., Menez, A., and Boulain, J. C. (2002). Artificial evolution of an enzyme active site: structural studies of three highly active mutants of *Escherichia coli* alkaline phosphatase. J Mol Biol 316, 941-953.

Lisova, O., Hardy, F., Petit, V., and Bedouelle, H. (2007). Mapping to completeness and transplantation of a group specific, discontinuous, neutralizing epitope in the envelope protein of the dengue virus. J. Gen. Virol., in press.

Ludolfs, D., Schilling, S., Altenschmidt, J., and Schmitz, H. (2002). Serological differentiation of infections with dengue virus serotypes 1 to 4 by using recombinant antigens. J Clin Microbiol 40, 4317-4320.

Ludolfs, D., Niedrig, M., Paweska, J. T. and Schmitz, H. (2007). Reverse ELISA for the detection of anti West Nile virus IgG antibodies in humans. Eur J Clin Micrbiol Infect Dis 26, Number 7, July, Pages 467-473.

Malkinson, M., Banet, C., Weisman, Y., Pokamunski, S., King, R., Drouet, M. T., and Deubel, V. (2002). Introduction of West Nile virus in the Middle East by migrating white storks. Emerg Infect Dis 8, 392-397.

Martin, D. A., Biggerstaff, B. J., Allen, B., Johnson, A. J., Lanciotti, R. S., and Roehrig, J. T. (2002). Use of immunoglobulin m cross-reactions in differential diagnosis of human flaviviral encephalitis infections in the United States. Clin Diagn Lab Immunol 9, 544-549.

Martin, D. A., Noga A., Kosoy O., Johnson, A. J., Petersen, L. R., Lanciotti, R. S. (2004). Evaluation of a diagnostic algorithm using immunoglobulin M enzyme-linked immunosorbent assay to differentiate human West Nile Virus and St. Louis Encephalitis virus infections during the 2002 West Nile Virus epidemic in the United States. Clin. Diagn. Lab. Immunol., 11, 1130-1133.

Martin, D. A., Muth, D. A., Brown, T., Johnson, A. J., Karabatsos, N., and Roehrig, J. T. (2000). Standardization of immunoglobulin M capture enzyme-linked immunosorbent assays for routine diagnosis of arboviral infections. J Clin Microbiol 38, 1823-1826.

Matheus, S., Deparis, X., Labeau, B., Lelarge, J., Morvan, J., and Dussart, P. (2005). Discrimination between primary and secondary dengue virus infection by an immunoglobulin G avidity test using a single acute-phase serum sample. J Clin Microbiol 43, 2793-2797.

McBride, W. J., and Bielefeldt-Ohmann, H. (2000). Dengue viral infections; pathogenesis and epidemiology. Microbes Infect 2, 1041-1050.

Modis, Y., Ogata, S., Clements, D., and Harrison, S. C. (2003). A ligand-binding pocket in the dengue virus envelope glycoprotein. Proc Natl Acad Sci USA 100, 6986-6991.

Modis, Y., Ogata, S., Clements, D., and Harrison, S. C. (2005). Variable surface epitopes in the crystal structure of dengue virus type 3 envelope glycoprotein. J Virol 79, 1223-1231.

Mongkolsapaya, J., Dejnirattisai, W., Xu, X. N., Vasanawathana, S., Tangthawornchaikul, N., Chairunsri, A., Sawasdivorn, S., Duangchinda, T., Dong, T., Rowland-Jones, S., et al. (2003). Original antigenic sin and apoptosis in the pathogenesis of dengue hemorrhagic fever. Nat Med 9, 921-927.

Muerhoff, A. S., Jiang, L., Shah, D. O., Gutierrez, R. A., Patel, J., Garolis, C., Kyrk, C. R., Leckie, G., Frank, A., Stewart, J. L., and Dawson, G. J. (2002). Detection of HCV core antigen in human serum and plasma with an automated chemiluminescent immunoassay. Transfusion 42, 349-356.

Mukhopadhyay, S., Kim, B. S., Chipman, P. R., Rossmann, M. G., and Kuhn, R. J. (2003). Structure of West Nile virus. Science 302, 248.

Muller, B. H., Lamoure, C., Le Du, M. H., Cattolico, L., Lajeunesse, E., Lemaitre, F., Pearson, A., Ducancel, F., Menez, A., and Boulain, J. C. (2001). Improving *Escherichia coli* alkaline phosphatase efficacy by additional mutations inside and outside the catalytic pocket. Chembiochem 2, 517-523.

Nawa, M., Yamada, K. I., Takasaki, T., Akatsuka, T., and Kurane, I. (2000). Serotype-cross-reactive immunoglobulin M responses in dengue virus infections determined by enzyme-linked immunosorbent assay. Clin Diagn Lab Immunol 7, 774-777.

Plückthun, A. (1996). Producing antibodies in *Escherichia Coli*: from PCR to fermentation, In Antibody Engineering, J. McCafferty, H. R. Hoogenboom, and D. J. Chiswell, eds. (New-York: Oxford University Press), pp. 203-252.

Prince, H. E., and Lape-Nixon, M. (2005). Evaluation of a West Nile virus immunoglobulin A capture enzyme-linked immunosorbent assay. Clin Diagn Lab Immunol 12, 231-233.

Purdy, D. E., Noga, A. J., and Chang, G. J. (2004). Noninfectious recombinant antigen for detection of St. Louis encephalitis virus-specific antibodies in serum by enzyme-linked immunosorbent assay. J Clin Microbiol 42, 4709-4717.

Rey, F. A., Heinz, F. X., Mandl, C., Kunz, C., and Harrison, S. C. (1995). The envelope glycoprotein from tick-borne encephalitis virus at 2 A resolution. Nature 375, 291-298.

Rice, P., Longden, I., and Bleasby, A. (2000). EMBOSS: the European Molecular Biology Open Software Suite. Trends Genet 16, 276-277.

Roehrig, J. T. (2003). Antigenic structure of flavivirus proteins. Adv Virus Res 59, 141-175.

Roehrig, J. T., Volpe, K. E., Squires, J., Hunt, A. R., Davis, B. S., and Chang, G. J. (2004). Contribution of disulfide bridging to epitope expression of the dengue type 2 virus envelope glycoprotein. J Virol 78, 2648-2652.

Sambrook, J., and Russell, D. W. (2001). Molecular Cloning: A Laboratory Manual, 3rd edn (Cold Spring Harbor, N.Y.: Cold Spring Harbor Press).

Sanchez, M. D., Pierson, T. C., McAllister, D., Hanna, S. L., Puffer, B. A., Valentine, L. E., Murtadha, M. M., Hoxie, J. A., and Doms, R. W. (2005). Characterization of neutralizing antibodies to West Nile virus. Virology 336, 70-82.

Serafin, I. L., and Aaskov, J. G. (2001). Identification of epitopes on the envelope (E) protein of dengue 2 and dengue 3 viruses using monoclonal antibodies. Arch Virol 146, 2469-2479.

Shu, P. Y., Chen, L. K., Chang, S. F., Su, C. L., Chien, L. J., Chin, C., Lin, T. H., and Huang, J. H. (2004). Dengue virus serotyping based on envelope and membrane and nonstructural protein NS1 serotype-specific capture immunoglobulin M enzyme-linked immunosorbent assays. J Clin Microbiol 42, 2489-2494.

Shu, P. Y., Chen, L. K., Chang, S. F., Yueh, Y. Y., Chow, L., Chien, L. J., Chin, C., Lin, T. H., and Huang, J. H. (2003). Comparison of capture immunoglobulin M (IgM) and IgG enzyme-linked immunosorbent assay (ELISA) and nonstructural protein NS1 serotype-specific IgG ELISA for differentiation of primary and secondary dengue virus infections. Clin Diagn Lab Immunol 10, 622-630.

Shu, P. Y., Chen, L. K., Chang, S. F., Yueh, Y. Y., Chow, L., Chien, L. J., Chin, C., Yang, H. H., Lin, T. H., and Huang, J. H. (2002). Potential application of nonstructural protein NS1 serotype-specific immunoglobulin G enzyme-linked immunosorbent assay in the seroepidemiologic study of dengue virus infection: correlation of results with those of the plaque reduction neutralization test. J Clin Microbiol 40, 1840-1844.

Shu, P. Y., and Huang, J. H. (2004). Current advances in dengue diagnosis. Clin Diagn Lab Immunol 11, 642-650.

Simmons, M., Porter, K. R., Escamilla, J., Graham, R., Watts, D. M., Eckels, K. H., and Hayes, C. G. (1998). Evaluation of recombinant dengue viral envelope B domain protein antigens for the detection of dengue complex-specific antibodies. Am J Trop Med Hyg 58, 144-151.

Talarmin, A., Labeau, B., Lelarge, J., and Sarthou, J. L. (1998). Immunoglobulin A-specific capture enzyme-linked immunosorbent assay for diagnosis of dengue fever. J Clin Microbiol 36, 1189-1192.

Teles, F. R., Prazeres, D. M., and Lima-Filho, J. L. (2005). Trends in dengue diagnosis. Rev Med Virol 15, 287-302.

Vieira, J., and Messing, J. (1982). The pUC plasmids, an M13mp7-derived system for insertion mutagenesis and sequencing with synthetic universal primers. Gene 19, 259-268.

Vorndam, V., and Kuno, G. (1997). Laboratory diagnosis of dengue virus infections, In Dengue and Dengue Hemorrhagic Fever, D. J. Gubler, and G. Kuno, eds. (Cambridge: CAB International), pp. 313-333.

WHO (1997). Dengue Haemorrhagic Fever: diagnosis, prevention, treatment and control, Second edn (Geneva: WHO Publications).

Wu, H. C., Huang, Y. L., Chao, T. T., Jan, J. T., Huang, J. L., Chiang, H. Y., King, C. C., and Shaio, M. F. (2001). Identification of B-cell epitope of dengue virus type 1 and its application in diagnosis of patients. J Clin Microbiol 39, 977-982.

Yao, Z. J., Kao, M. C., Loh, K. C., and Chung, M. C. (1995). A serotype-specific epitope of dengue virus 1 identified by phage displayed random peptide library. FEMS Microbiol Lett 127, 93-98.

Yoshii, K., Hayasaka, D., Goto, A., Obara, M., Araki, K., Yoshimatsu, K., Arikawa, J., Ivanov, L., Mizutani, T., Kariwa, H., and Takashima, I. (2003). Enzyme-linked immunosorbent assay using recombinant antigens expressed in mammalian cells for serodiagnosis of tick-borne encephalitis. J Virol Methods 108, 171-179.

---

The invention claimed is:

1. A method for the diagnosis or the screening of a subject or animal host to determine whether the subject or animal host has been infected with an arbovirus, comprising:
   (i) contacting a sample from the subject or animal with a solid support sensitized with an Ig binding protein which is directed against a specific class of Ig molecules of the subject or animal species under consideration and
   (ii) incubating the immunocomplex formed in (i) with a detector molecule comprising a hybrid protein comprising at least a dimer of an arboviral ED3 domain fused with an *E. coli* alkaline phosphatase (PhoA) having two mutations in its active site: D153G and D330N and comprising SEQ ID NO: 24, (iii) detecting said immunocomplex in said sample, (iv) correlating the detection of said immunocomplex to indicate that the subject or animal host has been infected with an arbovirus.

2. The method according to claim 1, wherein the Ig binding protein is selected in the group consisting of anti-IgM, anti-IgG and anti-IgA antibodies.

3. The method according to claim 1, wherein said arbovirus is a flavivirus.

4. The method according to claim 1, wherein said hybrid protein further comprises a polypeptide tag.

5. The method according to claim 4, wherein said polypeptide tag is selected in the group consisting of hexahistidine (SEQ ID NO: 32), c-MYC, HA, VSV-G, HSV, V5 and FLAG.

6. The method according to claim 1, wherein said hybrid protein further comprises a hexahistidine (SEQ ID NO: 32), and said arboviral ED3 domain is a flaviviral ED3 domain.

7. The method according to claim 1, wherein the ED3 domain polypeptide is selected from the group consisting of a yellow fever virus ED3 domain polypeptide, a West Nile virus ED3 domain polypeptide, a Dengue virus ED3 domain polypeptide, a St Louis encephalitis virus ED3 domain polypeptide, a Murray Valley encephalitis virus ED3 domain polypeptide and a Japanese encephalitis virus ED3 domain polypeptide.

8. A method for screening for arbovirus antibodies in a subject or an animal, said method comprising:

(i) contacting a sample from said subject or animal with a solid support sensitized with an Ig binding protein which is directed against a specific class of Ig molecules of the subject or the animal species under consideration, (ii) incubating the immunocomplex formed in (i) with a detector molecule comprising a hybrid protein comprising at least a dimer of an arboviral ED3 domain fused with an *E. coli* alkaline phosphatase (PhoA) having two mutations in its active site: D153G and D330N and comprising SEQ ID NO: 24 and (iii) detecting the presence of said arbovirus antibodies.

9. The method according to claim 8, wherein the Ig binding protein is selected in the group consisting of anti-IgM, anti-IgG and anti-IgA antibodies.

10. The method according to claim 8, wherein said arbovirus is a flavivirus.

11. The method according to claim 8, wherein said hybrid protein further comprises a polypeptide tag.

12. The method according to claim 11, wherein said polypeptide tag is selected in the group consisting of hexahistidine (SEQ ID NO: 32), c-MYC, HA, VSV-G, HSV, V5 and FLAG.

13. The method according to claim 8, wherein said hybrid protein further comprises a hexahistidine (SEQ ID NO: 32), and said arboviral ED3 domain is a flaviviral ED3 domain.

14. The method according to claim 8, wherein the ED3 domain polypeptide is selected from the group consisting of a yellow fever virus ED3 domain polypeptide, a West Nile virus ED3 domain polypeptide, a Dengue virus ED3 domain polypeptide, a St Louis encephalitis virus ED3 domain polypeptide, a Murray Valley encephalitis virus ED3 domain polypeptide and a Japanese encephalitis virus ED3 domain polypeptide.

* * * * *

SEQUENCE LISTING

```
<160> NUMBER OF SEQ ID NOS: 34

<210> SEQ ID NO 1
<211> LENGTH: 1788
<212> TYPE: DNA
<213> ORGANISM: Artificial Sequence
<220> FEATURE:
<223> OTHER INFORMATION: Description of Artificial Sequence: Synthetic
      DNA encoding H6-ED3.DEN1-PhoA gene (from pEBL11)
<220> FEATURE:
<221> NAME/KEY: sig_peptide
<222> LOCATION: (1)..(63)
<220> FEATURE:
<221> NAME/KEY: CDS
<222> LOCATION: (64)..(1785)
<223> OTHER INFORMATION: H6-ED3.DEN1-PhoA (88-105 = His-tag; 127-444 =
      ED3.DEN1; 64-81 and 454-1788 = PhoA)

<400> SEQUENCE: 1
gtgaaacaaa gcactattgc actggcactc ttaccgttac tgtttacccc tgtgacaaaa       60 gcc cgg aca cca gaa atg ccc gtc gaa cat cac cat cac cat cac gac      108
    Arg Thr Pro Glu Met Pro Val Glu His His His His His His Asp
    1               5                   10                  15 gat gac gat aag gtc gac aaa ggg atg tca tat gtg atg tgc aca ggc      156
Asp Asp Asp Lys Val Asp Lys Gly Met Ser Tyr Val Met Cys Thr Gly
                20                  25                  30 tca ttt aag cta gag aag gaa gtg gct gag acc cag cat ggg act gtc      204
Ser Phe Lys Leu Glu Lys Glu Val Ala Glu Thr Gln His Gly Thr Val
            35                  40                  45 cta gtg cag gtt aaa tac gaa gga aca gat gcg cca tgc aag atc ccc      252
Leu Val Gln Val Lys Tyr Glu Gly Thr Asp Ala Pro Cys Lys Ile Pro
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 50  |     |     |     |     | 55  |     |     |     |     | 60  |     |      |
| ttt | tcg | acc | caa | gat | gag | aaa | gga | gtg | acc | cag | aat | ggg | aga | ttg | ata | 300  |
| Phe | Ser | Thr | Gln | Asp | Glu | Lys | Gly | Val | Thr | Gln | Asn | Gly | Arg | Leu | Ile |      |
|     | 65  |     |     |     |     | 70  |     |     |     |     | 75  |     |     |     |     |      |
| aca | gcc | aat | ccc | ata | gtt | act | gac | aaa | gaa | aaa | cca | gtc | aac | att | gag | 348  |
| Thr | Ala | Asn | Pro | Ile | Val | Thr | Asp | Lys | Glu | Lys | Pro | Val | Asn | Ile | Glu |      |
| 80  |     |     |     |     | 85  |     |     |     |     | 90  |     |     |     |     | 95  |      |
| aca | gaa | cca | cct | ttt | ggt | gag | agc | tac | atc | ata | gta | ggg | gca | ggt | gaa | 396  |
| Thr | Glu | Pro | Pro | Phe | Gly | Glu | Ser | Tyr | Ile | Ile | Val | Gly | Ala | Gly | Glu |      |
|     |     |     |     |     | 100 |     |     |     |     | 105 |     |     |     |     | 110 |      |
| aaa | gct | ttg | aaa | cta | agc | tgg | ttc | aag | aag | gga | agc | agc | ata | ggg | aaa | 444  |
| Lys | Ala | Leu | Lys | Leu | Ser | Trp | Phe | Lys | Lys | Gly | Ser | Ser | Ile | Gly | Lys |      |
|     |     |     | 115 |     |     |     |     | 120 |     |     |     |     | 125 |     |     |      |
| act | agt | ggg | gtt | ctg | gaa | aac | cgg | gct | gct | cag | ggc | gat | att | act | gca | 492  |
| Thr | Ser | Gly | Val | Leu | Glu | Asn | Arg | Ala | Ala | Gln | Gly | Asp | Ile | Thr | Ala |      |
|     |     | 130 |     |     |     |     | 135 |     |     |     |     | 140 |     |     |     |      |
| ccc | ggc | ggt | gct | cgc | cgt | tta | acg | ggt | gat | cag | act | gcc | gct | ctg | cgt | 540  |
| Pro | Gly | Gly | Ala | Arg | Arg | Leu | Thr | Gly | Asp | Gln | Thr | Ala | Ala | Leu | Arg |      |
|     | 145 |     |     |     |     | 150 |     |     |     |     | 155 |     |     |     |     |      |
| gat | tct | ctt | agc | gat | aaa | cct | gca | aaa | aat | att | att | ttg | ctg | att | ggc | 588  |
| Asp | Ser | Leu | Ser | Asp | Lys | Pro | Ala | Lys | Asn | Ile | Ile | Leu | Leu | Ile | Gly |      |
| 160 |     |     |     |     | 165 |     |     |     |     | 170 |     |     |     |     | 175 |      |
| gat | ggg | atg | ggg | gac | tcg | gaa | att | act | gcc | gca | cgt | aat | tat | gcc | gaa | 636  |
| Asp | Gly | Met | Gly | Asp | Ser | Glu | Ile | Thr | Ala | Ala | Arg | Asn | Tyr | Ala | Glu |      |
|     |     |     |     | 180 |     |     |     |     | 185 |     |     |     |     | 190 |     |      |
| ggt | gcg | ggc | ggc | ttt | ttt | aaa | ggt | ata | gat | gcc | tta | ccg | ctt | acc | ggg | 684  |
| Gly | Ala | Gly | Gly | Phe | Phe | Lys | Gly | Ile | Asp | Ala | Leu | Pro | Leu | Thr | Gly |      |
|     |     |     | 195 |     |     |     |     | 200 |     |     |     |     | 205 |     |     |      |
| caa | tac | act | cac | tat | gcg | ctg | aat | aaa | aaa | acc | ggc | aaa | ccg | gac | tac | 732  |
| Gln | Tyr | Thr | His | Tyr | Ala | Leu | Asn | Lys | Lys | Thr | Gly | Lys | Pro | Asp | Tyr |      |
|     |     | 210 |     |     |     |     | 215 |     |     |     |     | 220 |     |     |     |      |
| gtc | acc | gac | tcg | gct | gca | tca | gca | acc | gcc | tgg | tca | acc | ggt | gtc | aaa | 780  |
| Val | Thr | Asp | Ser | Ala | Ala | Ser | Ala | Thr | Ala | Trp | Ser | Thr | Gly | Val | Lys |      |
|     | 225 |     |     |     |     | 230 |     |     |     |     | 235 |     |     |     |     |      |
| acc | tat | aac | ggc | gcg | ctg | ggc | gtc | gat | att | cac | gaa | aaa | gat | cac | cca | 828  |
| Thr | Tyr | Asn | Gly | Ala | Leu | Gly | Val | Asp | Ile | His | Glu | Lys | Asp | His | Pro |      |
| 240 |     |     |     |     | 245 |     |     |     |     | 250 |     |     |     |     | 255 |      |
| acg | att | ctg | gaa | atg | gca | aaa | gcc | gca | ggt | ctg | gcg | acc | ggt | aac | gtt | 876  |
| Thr | Ile | Leu | Glu | Met | Ala | Lys | Ala | Ala | Gly | Leu | Ala | Thr | Gly | Asn | Val |      |
|     |     |     |     | 260 |     |     |     |     | 265 |     |     |     |     | 270 |     |      |
| tct | acc | gca | gag | ttg | cag | ggt | gcc | acg | ccc | gct | gcg | ctg | gtg | gca | cat | 924  |
| Ser | Thr | Ala | Glu | Leu | Gln | Gly | Ala | Thr | Pro | Ala | Ala | Leu | Val | Ala | His |      |
|     |     |     | 275 |     |     |     |     | 280 |     |     |     |     | 285 |     |     |      |
| gtg | acc | tcg | cgc | aaa | tgc | tac | ggt | ccg | agc | gcg | acc | agt | gaa | aaa | tgt | 972  |
| Val | Thr | Ser | Arg | Lys | Cys | Tyr | Gly | Pro | Ser | Ala | Thr | Ser | Glu | Lys | Cys |      |
|     |     | 290 |     |     |     |     | 295 |     |     |     |     | 300 |     |     |     |      |
| ccg | ggt | aac | gct | ctg | gaa | aaa | ggc | gga | aaa | gga | tcg | att | acc | gaa | cag | 1020 |
| Pro | Gly | Asn | Ala | Leu | Glu | Lys | Gly | Gly | Lys | Gly | Ser | Ile | Thr | Glu | Gln |      |
|     | 305 |     |     |     |     | 310 |     |     |     |     | 315 |     |     |     |     |      |
| ctg | ctt | aac | gct | cgt | gcc | gac | gtt | acg | ctt | ggc | ggc | ggc | gca | aaa | acc | 1068 |
| Leu | Leu | Asn | Ala | Arg | Ala | Asp | Val | Thr | Leu | Gly | Gly | Gly | Ala | Lys | Thr |      |
| 320 |     |     |     |     | 325 |     |     |     |     | 330 |     |     |     |     | 335 |      |
| ttt | gct | gaa | acg | gca | acc | gct | ggt | gaa | tgg | cag | gga | aaa | acg | ctg | cgt | 1116 |
| Phe | Ala | Glu | Thr | Ala | Thr | Ala | Gly | Glu | Trp | Gln | Gly | Lys | Thr | Leu | Arg |      |
|     |     |     |     | 340 |     |     |     |     | 345 |     |     |     |     | 350 |     |      |
| gaa | cag | gca | cag | gcg | cgt | ggt | tat | cag | ttg | gtg | agc | gat | gct | gcc | tca | 1164 |
| Glu | Gln | Ala | Gln | Ala | Arg | Gly | Tyr | Gln | Leu | Val | Ser | Asp | Ala | Ala | Ser |      |
|     |     |     | 355 |     |     |     |     | 360 |     |     |     |     | 365 |     |     |      |
| ctg | aat | tcg | gtg | acg | gaa | gcg | aat | cag | caa | aaa | ccc | ctg | ctt | ggc | ctg | 1212 |
| Leu | Asn | Ser | Val | Thr | Glu | Ala | Asn | Gln | Gln | Lys | Pro | Leu | Leu | Gly | Leu |      |

```
                   370                 375                 380
ttt gct gac ggc aat atg cca gtg cgc tgg cta gga ccg aaa gca acg      1260
Phe Ala Asp Gly Asn Met Pro Val Arg Trp Leu Gly Pro Lys Ala Thr
385                 390                 395 tac cat ggc aat atc gat aag ccc gca gtc acc tgt acg cca aat ccg      1308
Tyr His Gly Asn Ile Asp Lys Pro Ala Val Thr Cys Thr Pro Asn Pro
400                 405                 410                 415 caa cgt aat gac agt gta cca acc ctg gcg cag atg acc gac aaa gcc      1356
Gln Arg Asn Asp Ser Val Pro Thr Leu Ala Gln Met Thr Asp Lys Ala
                420                 425                 430 att gaa ttg ttg agt aaa aat gag aaa ggc ttt ttc ctg caa gtt gaa      1404
Ile Glu Leu Leu Ser Lys Asn Glu Lys Gly Phe Phe Leu Gln Val Glu
                435                 440                 445 ggt gcg tca atc gat aaa cag aat cat gct gcg aat cct tgt ggg caa      1452
Gly Ala Ser Ile Asp Lys Gln Asn His Ala Ala Asn Pro Cys Gly Gln
                450                 455                 460 att ggc gag acg gtc gat ctc gat gaa gcc gta caa cgg gcg ctg gaa      1500
Ile Gly Glu Thr Val Asp Leu Asp Glu Ala Val Gln Arg Ala Leu Glu
465                 470                 475 ttc gct aaa aag gag ggt aac acg ctg gtc ata gtc acc gct gat cac      1548
Phe Ala Lys Lys Glu Gly Asn Thr Leu Val Ile Val Thr Ala Asp His
480                 485                 490                 495 gcc cac gcc agc cag att gtt gcg ccg gat acc aaa gct ccg ggc ctc      1596
Ala His Ala Ser Gln Ile Val Ala Pro Asp Thr Lys Ala Pro Gly Leu
                500                 505                 510 acc cag gcg cta aat acc aaa gat ggc gca gtg atg gtg atg agt tac      1644
Thr Gln Ala Leu Asn Thr Lys Asp Gly Ala Val Met Val Met Ser Tyr
                515                 520                 525 ggg aac tcc gaa gag gat tca caa gaa cat acc ggc agt cag ttg cgt      1692
Gly Asn Ser Glu Glu Asp Ser Gln Glu His Thr Gly Ser Gln Leu Arg
                530                 535                 540 att gcg gcg tat ggc ccg cat gcc gcc aat gtt gtt gga ctg acc gac      1740
Ile Ala Ala Tyr Gly Pro His Ala Ala Asn Val Val Gly Leu Thr Asp
545                 550                 555 cag acc gat ctc ttc tac acc atg aaa gcc gct ctg ggg ctg aaa taa     1788
Gln Thr Asp Leu Phe Tyr Thr Met Lys Ala Ala Leu Gly Leu Lys
560                 565                 570

<210> SEQ ID NO 2
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Arg Thr Pro Glu Met Pro Val Glu His His His His His Asp Asp
1               5                   10                  15

Asp Asp Lys Val Asp Lys Gly Met Ser Tyr Val Met Cys Thr Gly Ser
                20                  25                  30

Phe Lys Leu Glu Lys Glu Val Ala Glu Thr Gln His Gly Thr Val Leu
            35                  40                  45

Val Gln Val Lys Tyr Glu Gly Thr Asp Ala Pro Cys Lys Ile Pro Phe
        50                  55                  60

Ser Thr Gln Asp Glu Lys Gly Val Thr Gln Asn Gly Arg Leu Ile Thr
65                  70                  75                  80

Ala Asn Pro Ile Val Thr Asp Lys Glu Lys Pro Val Asn Ile Glu Thr
                85                  90                  95

Glu Pro Pro Phe Gly Glu Ser Tyr Ile Ile Val Gly Ala Gly Glu Lys
```

```
                  100                 105                 110
Ala Leu Lys Leu Ser Trp Phe Lys Lys Gly Ser Ser Ile Gly Lys Thr
            115                 120                 125
Ser Gly Val Leu Glu Asn Arg Ala Ala Gln Gly Asp Ile Thr Ala Pro
            130                 135                 140
Gly Gly Ala Arg Arg Leu Thr Gly Asp Gln Thr Ala Ala Leu Arg Asp
145                 150                 155                 160
Ser Leu Ser Asp Lys Pro Ala Lys Asn Ile Ile Leu Leu Ile Gly Asp
                165                 170                 175
Gly Met Gly Asp Ser Glu Ile Thr Ala Ala Arg Asn Tyr Ala Glu Gly
                180                 185                 190
Ala Gly Gly Phe Phe Lys Gly Ile Asp Ala Leu Pro Leu Thr Gly Gln
            195                 200                 205
Tyr Thr His Tyr Ala Leu Asn Lys Lys Thr Gly Lys Pro Asp Tyr Val
        210                 215                 220
Thr Asp Ser Ala Ala Ser Ala Thr Ala Trp Ser Thr Gly Val Lys Thr
225                 230                 235                 240
Tyr Asn Gly Ala Leu Gly Val Asp Ile His Glu Lys Asp His Pro Thr
                245                 250                 255
Ile Leu Glu Met Ala Lys Ala Ala Gly Leu Ala Thr Gly Asn Val Ser
                260                 265                 270
Thr Ala Glu Leu Gln Gly Ala Thr Pro Ala Ala Leu Val Ala His Val
            275                 280                 285
Thr Ser Arg Lys Cys Tyr Gly Pro Ser Ala Thr Ser Glu Lys Cys Pro
        290                 295                 300
Gly Asn Ala Leu Glu Lys Gly Gly Lys Gly Ser Ile Thr Glu Gln Leu
305                 310                 315                 320
Leu Asn Ala Arg Ala Asp Val Thr Leu Gly Gly Gly Ala Lys Thr Phe
                325                 330                 335
Ala Glu Thr Ala Thr Ala Gly Glu Trp Gln Gly Lys Thr Leu Arg Glu
                340                 345                 350
Gln Ala Gln Ala Arg Gly Tyr Gln Leu Val Ser Asp Ala Ala Ser Leu
            355                 360                 365
Asn Ser Val Thr Glu Ala Asn Gln Gln Lys Pro Leu Leu Gly Leu Phe
        370                 375                 380
Ala Asp Gly Asn Met Pro Val Arg Trp Leu Gly Pro Lys Ala Thr Tyr
385                 390                 395                 400
His Gly Asn Ile Asp Lys Pro Ala Val Thr Cys Thr Pro Asn Pro Gln
                405                 410                 415
Arg Asn Asp Ser Val Pro Thr Leu Ala Gln Met Thr Asp Lys Ala Ile
                420                 425                 430
Glu Leu Leu Ser Lys Asn Glu Lys Gly Phe Phe Leu Gln Val Glu Gly
            435                 440                 445
Ala Ser Ile Asp Lys Gln Asn His Ala Ala Asn Pro Cys Gly Gln Ile
        450                 455                 460
Gly Glu Thr Val Asp Leu Asp Glu Ala Val Gln Arg Ala Leu Glu Phe
465                 470                 475                 480
Ala Lys Lys Glu Gly Asn Thr Leu Val Ile Val Thr Ala Asp His Ala
                485                 490                 495
His Ala Ser Gln Ile Val Ala Pro Asp Thr Lys Ala Pro Gly Leu Thr
            500                 505                 510
Gln Ala Leu Asn Thr Lys Asp Gly Ala Val Met Val Met Ser Tyr Gly
        515                 520                 525
```

-continued

```
Asn Ser Glu Glu Asp Ser Gln Glu His Thr Gly Ser Gln Leu Arg Ile
            530                 535                 540
Ala Ala Tyr Gly Pro His Ala Ala Asn Val Val Gly Leu Thr Asp Gln
545                 550                 555                 560
Thr Asp Leu Phe Tyr Thr Met Lys Ala Ala Leu Gly Leu Lys
                565                 570

<210> SEQ ID NO 3
<211> LENGTH: 1788
<212> TYPE: DNA
<213> ORGANISM: Artificial Sequence
<220> FEATURE:
<223> OTHER INFORMATION: Description of Artificial Sequence: Synthetic
      DNA encoding H6-ED3.DEN2-PhoA gene (from pEBL12)
<220> FEATURE:
<221> NAME/KEY: sig_peptide
<222> LOCATION: (1)..(63)
<220> FEATURE:
<221> NAME/KEY: CDS
<222> LOCATION: (64)..(1785)
<223> OTHER INFORMATION: H6-ED3.DEN2-PhoA (88-105 = His-tag; 127-444 =
      ED3.DEN2; 64-81 and 454-1788 = PhoA)

<400> SEQUENCE: 3
gtgaaacaaa gcactattgc actggcactc ttaccgttac tgtttacccc tgtgacaaaa        60 gcc cgg aca cca gaa atg ccc gtc gaa cat cac cat cac cat cac gac         108
Arg Thr Pro Glu Met Pro Val Glu His His His His His His Asp
  1               5                  10                  15 gat gac gat aag gtc gac aaa gga atg tca tac tct atg tgt aca gga         156
Asp Asp Asp Lys Val Asp Lys Gly Met Ser Tyr Ser Met Cys Thr Gly
             20                  25                  30 aag ttt aaa att gtg aag gaa ata gca gaa aca caa cat gga aca ata         204
Lys Phe Lys Ile Val Lys Glu Ile Ala Glu Thr Gln His Gly Thr Ile
         35                  40                  45 gtt atc aga gta caa tat gaa ggg gac ggc tct cca tgt aag atc cct         252
Val Ile Arg Val Gln Tyr Glu Gly Asp Gly Ser Pro Cys Lys Ile Pro
     50                  55                  60 ttt gag ata atg gat ttg gaa aaa aga cac gtc tta ggt cgc ctg att         300
Phe Glu Ile Met Asp Leu Glu Lys Arg His Val Leu Gly Arg Leu Ile
 65                  70                  75 aca gtt aac ccg atc gta aca gaa aaa gat agc cca gtc aac ata gaa         348
Thr Val Asn Pro Ile Val Thr Glu Lys Asp Ser Pro Val Asn Ile Glu
 80                  85                  90                  95 gca gaa cct cca ttc gga gac agc tac atc atc ata gga gta gag ccg         396
Ala Glu Pro Pro Phe Gly Asp Ser Tyr Ile Ile Ile Gly Val Glu Pro
                100                 105                 110 gga caa ttg aaa ctc aac tgg ttt aag aaa gga agt tcc atc ggc caa         444
Gly Gln Leu Lys Leu Asn Trp Phe Lys Lys Gly Ser Ser Ile Gly Gln
            115                 120                 125 act agt ggg gtt ctg gaa aac cgg gct gct cag ggc gat att act gca         492
Thr Ser Gly Val Leu Glu Asn Arg Ala Ala Gln Gly Asp Ile Thr Ala
        130                 135                 140 ccc ggc ggt gct cgc cgt tta acg ggt gat cag act gcc gct ctg cgt         540
Pro Gly Gly Ala Arg Arg Leu Thr Gly Asp Gln Thr Ala Ala Leu Arg
    145                 150                 155 gat tct ctt agc gat aaa cct gca aaa aat att att ttg ctg att ggc         588
Asp Ser Leu Ser Asp Lys Pro Ala Lys Asn Ile Ile Leu Leu Ile Gly
160                 165                 170                 175 gat ggg atg ggg gac tcg gaa att act gcc gca cgt aat tat gcc gaa         636
Asp Gly Met Gly Asp Ser Glu Ile Thr Ala Ala Arg Asn Tyr Ala Glu
                180                 185                 190 ggt gcg ggc ggc ttt ttt aaa ggt ata gat gcc tta ccg ctt acc ggg         684
Gly Ala Gly Gly Phe Phe Lys Gly Ile Asp Ala Leu Pro Leu Thr Gly
```

-continued

```
            195                 200                 205
caa tac act cac tat gcg ctg aat aaa aaa acc ggc aaa ccg gac tac    732
Gln Tyr Thr His Tyr Ala Leu Asn Lys Lys Thr Gly Lys Pro Asp Tyr
            210                 215                 220 gtc acc gac tcg gct gca tca gca acc gcc tgg tca acc ggt gtc aaa    780
Val Thr Asp Ser Ala Ala Ser Ala Thr Ala Trp Ser Thr Gly Val Lys
225                 230                 235 acc tat aac ggc gcg ctg ggc gtc gat att cac gaa aaa gat cac cca    828
Thr Tyr Asn Gly Ala Leu Gly Val Asp Ile His Glu Lys Asp His Pro
240                 245                 250                 255 acg att ctg gaa atg gca aaa gcc gca ggt ctg gcg acc ggt aac gtt    876
Thr Ile Leu Glu Met Ala Lys Ala Ala Gly Leu Ala Thr Gly Asn Val
                260                 265                 270 tct acc gca gag ttg cag ggt gcc acg ccc gct gcg ctg gtg gca cat    924
Ser Thr Ala Glu Leu Gln Gly Ala Thr Pro Ala Ala Leu Val Ala His
            275                 280                 285 gtg acc tcg cgc aaa tgc tac ggt ccg agc gcg acc agt gaa aaa tgt    972
Val Thr Ser Arg Lys Cys Tyr Gly Pro Ser Ala Thr Ser Glu Lys Cys
        290                 295                 300 ccg ggt aac gct ctg gaa aaa ggc gga aaa gga tcg att acc gaa cag   1020
Pro Gly Asn Ala Leu Glu Lys Gly Gly Lys Gly Ser Ile Thr Glu Gln
305                 310                 315 ctg ctt aac gct cgt gcc gac gtt acg ctt ggc ggc ggc gca aaa acc   1068
Leu Leu Asn Ala Arg Ala Asp Val Thr Leu Gly Gly Gly Ala Lys Thr
320                 325                 330                 335 ttt gct gaa acg gca acc gct ggt gaa tgg cag gga aaa acg ctg cgt   1116
Phe Ala Glu Thr Ala Thr Ala Gly Glu Trp Gln Gly Lys Thr Leu Arg
                340                 345                 350 gaa cag gca cag gcg cgt ggt tat cag ttg gtg agc gat gct gcc tca   1164
Glu Gln Ala Gln Ala Arg Gly Tyr Gln Leu Val Ser Asp Ala Ala Ser
            355                 360                 365 ctg aat tcg gtg acg gaa gcg aat cag caa aaa ccc ctg ctt ggc ctg   1212
Leu Asn Ser Val Thr Glu Ala Asn Gln Gln Lys Pro Leu Leu Gly Leu
        370                 375                 380 ttt gct gac ggc aat atg cca gtg cgc tgg cta gga ccg aaa gca acg   1260
Phe Ala Asp Gly Asn Met Pro Val Arg Trp Leu Gly Pro Lys Ala Thr
385                 390                 395 tac cat ggc aat atc gat aag ccc gca gtc acc tgt acg cca aat ccg   1308
Tyr His Gly Asn Ile Asp Lys Pro Ala Val Thr Cys Thr Pro Asn Pro
400                 405                 410                 415 caa cgt aat gac agt gta cca acc ctg gcg cag atg acc gac aaa gcc   1356
Gln Arg Asn Asp Ser Val Pro Thr Leu Ala Gln Met Thr Asp Lys Ala
                420                 425                 430 att gaa ttg ttg agt aaa aat gag aaa ggc ttt ttc ctg caa gtt gaa   1404
Ile Glu Leu Leu Ser Lys Asn Glu Lys Gly Phe Phe Leu Gln Val Glu
            435                 440                 445 ggt gcg tca atc gat aaa cag aat cat gct gcg aat cct tgt ggg caa   1452
Gly Ala Ser Ile Asp Lys Gln Asn His Ala Ala Asn Pro Cys Gly Gln
        450                 455                 460 att ggc gag acg gtc gat ctc gat gaa gcc gta caa cgg gcg ctg gaa   1500
Ile Gly Glu Thr Val Asp Leu Asp Glu Ala Val Gln Arg Ala Leu Glu
465                 470                 475 ttc gct aaa aag gag ggt aac acg ctg gtc ata gtc acc gct gat cac   1548
Phe Ala Lys Lys Glu Gly Asn Thr Leu Val Ile Val Thr Ala Asp His
480                 485                 490                 495 gcc cac gcc agc cag att gtt gcg ccg gat acc aaa gct ccg ggc ctc   1596
Ala His Ala Ser Gln Ile Val Ala Pro Asp Thr Lys Ala Pro Gly Leu
                500                 505                 510 acc cag gcg cta aat acc aaa gat ggc gca gtg atg gtg atg agt tac   1644
Thr Gln Ala Leu Asn Thr Lys Asp Gly Ala Val Met Val Met Ser Tyr
```

```
                          515                 520                 525
ggg aac tcc gaa gag gat tca caa gaa cat acc ggc agt cag ttg cgt         1692
Gly Asn Ser Glu Glu Asp Ser Gln Glu His Thr Gly Ser Gln Leu Arg
            530                 535                 540 att gcg gcg tat ggc ccg cat gcc gcc aat gtt gtt gga ctg acc gac         1740
Ile Ala Ala Tyr Gly Pro His Ala Ala Asn Val Val Gly Leu Thr Asp
545                 550                 555 cag acc gat ctc ttc tac acc atg aaa gcc gct ctg ggg ctg aaa taa         1788
Gln Thr Asp Leu Phe Tyr Thr Met Lys Ala Ala Leu Gly Leu Lys
560                 565                 570

<210> SEQ ID NO 4
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Arg Thr Pro Glu Met Pro Val Glu His His His His His His Asp Asp
1               5                   10                  15

Asp Asp Lys Val Asp Lys Gly Met Ser Tyr Ser Met Cys Thr Gly Lys
            20                  25                  30

Phe Lys Ile Val Lys Glu Ile Ala Glu Thr Gln His Gly Thr Ile Val
        35                  40                  45

Ile Arg Val Gln Tyr Glu Gly Asp Gly Ser Pro Cys Lys Ile Pro Phe
    50                  55                  60

Glu Ile Met Asp Leu Glu Lys Arg His Val Leu Gly Arg Leu Ile Thr
65                  70                  75                  80

Val Asn Pro Ile Val Thr Glu Lys Asp Ser Pro Val Asn Ile Glu Ala
                85                  90                  95

Glu Pro Pro Phe Gly Asp Ser Tyr Ile Ile Gly Val Glu Pro Gly
            100                 105                 110

Gln Leu Lys Leu Asn Trp Phe Lys Lys Gly Ser Ser Ile Gly Gln Thr
        115                 120                 125

Ser Gly Val Leu Glu Asn Arg Ala Ala Gln Gly Asp Ile Thr Ala Pro
    130                 135                 140

Gly Gly Ala Arg Arg Leu Thr Gly Asp Gln Thr Ala Ala Leu Arg Asp
145                 150                 155                 160

Ser Leu Ser Asp Lys Pro Ala Lys Asn Ile Ile Leu Leu Ile Gly Asp
                165                 170                 175

Gly Met Gly Asp Ser Glu Ile Thr Ala Ala Arg Asn Tyr Ala Glu Gly
            180                 185                 190

Ala Gly Gly Phe Phe Lys Gly Ile Asp Ala Leu Pro Leu Thr Gly Gln
        195                 200                 205

Tyr Thr His Tyr Ala Leu Asn Lys Lys Thr Gly Lys Pro Asp Tyr Val
    210                 215                 220

Thr Asp Ser Ala Ala Ser Ala Thr Ala Trp Ser Thr Gly Val Lys Thr
225                 230                 235                 240

Tyr Asn Gly Ala Leu Gly Val Asp Ile His Glu Lys Asp His Pro Thr
                245                 250                 255

Ile Leu Glu Met Ala Lys Ala Ala Gly Leu Ala Thr Gly Asn Val Ser
            260                 265                 270

Thr Ala Glu Leu Gln Gly Ala Thr Pro Ala Ala Leu Val Ala His Val
        275                 280                 285

Thr Ser Arg Lys Cys Tyr Gly Pro Ser Ala Thr Ser Glu Lys Cys Pro
```

```
                        290                 295                 300
Gly Asn Ala Leu Glu Lys Gly Lys Gly Ser Ile Thr Glu Gln Leu
305                 310                 315                 320

Leu Asn Ala Arg Ala Asp Val Thr Leu Gly Gly Gly Ala Lys Thr Phe
                325                 330                 335

Ala Glu Thr Ala Thr Ala Gly Glu Trp Gln Gly Lys Thr Leu Arg Glu
            340                 345                 350

Gln Ala Gln Ala Arg Gly Tyr Gln Leu Val Ser Asp Ala Ala Ser Leu
            355                 360                 365

Asn Ser Val Thr Glu Ala Asn Gln Gln Lys Pro Leu Leu Gly Leu Phe
370                 375                 380

Ala Asp Gly Asn Met Pro Val Arg Trp Leu Gly Pro Lys Ala Thr Tyr
385                 390                 395                 400

His Gly Asn Ile Asp Lys Pro Ala Val Thr Cys Thr Pro Asn Pro Gln
                405                 410                 415

Arg Asn Asp Ser Val Pro Thr Leu Ala Gln Met Thr Asp Lys Ala Ile
                420                 425                 430

Glu Leu Leu Ser Lys Asn Glu Lys Gly Phe Phe Leu Gln Val Glu Gly
            435                 440                 445

Ala Ser Ile Asp Lys Gln Asn His Ala Ala Asn Pro Cys Gly Gln Ile
450                 455                 460

Gly Glu Thr Val Asp Leu Asp Glu Ala Val Gln Arg Ala Leu Glu Phe
465                 470                 475                 480

Ala Lys Lys Glu Gly Asn Thr Leu Val Ile Val Thr Ala Asp His Ala
                485                 490                 495

His Ala Ser Gln Ile Val Ala Pro Asp Thr Lys Ala Pro Gly Leu Thr
                500                 505                 510

Gln Ala Leu Asn Thr Lys Asp Gly Ala Val Met Val Met Ser Tyr Gly
            515                 520                 525

Asn Ser Glu Glu Asp Ser Gln Glu His Thr Gly Ser Gln Leu Arg Ile
530                 535                 540

Ala Ala Tyr Gly Pro His Ala Ala Asn Val Val Gly Leu Thr Asp Gln
545                 550                 555                 560

Thr Asp Leu Phe Tyr Thr Met Lys Ala Ala Leu Gly Leu Lys
                565                 570

<210> SEQ ID NO 5
<211> LENGTH: 1788
<212> TYPE: DNA
<213> ORGANISM: Artificial Sequence
<220> FEATURE:
<223> OTHER INFORMATION: Description of Artificial Sequence: Synthetic
      DNA encoding H6-ED3.DEN3.PhoA gene (from pEBL13)
<220> FEATURE:
<221> NAME/KEY: sig_peptide
<222> LOCATION: (1)..(63)
<220> FEATURE:
<221> NAME/KEY: CDS
<222> LOCATION: (64)..(1785)
<223> OTHER INFORMATION: H6-ED3.DEN3-PhoA (88-105 = His-tag; 127-444 =
      ED3.DEN3; 64-81 and 454-1788 = PhoA)

<400> SEQUENCE: 5
gtgaaacaaa gcactattgc actggcactc ttaccgttac tgtttacccc tgtgacaaaa        60 gcc cgg aca cca gaa atg ccc gtc gaa cat cac cat cac cat cac gac         108
    Arg Thr Pro Glu Met Pro Val Glu His His His His His His Asp
    1               5                  10                  15 gat gac gat aag gtc gac aaa ggg atg agc tat gca atg tgc ttg aat         156
Asp Asp Asp Lys Val Asp Lys Gly Met Ser Tyr Ala Met Cys Leu Asn
```

-continued

|  |  |  | 20 |  |  |  | 25 |  |  |  | 30 |  |  |  |  |
|---|---|---|---|---|---|---|---|---|---|---|---|---|---|---|---|

```
acc ttt gtg ttg aag aaa gaa gtc tcc gaa acg cag cat ggg aca ata       204
Thr Phe Val Leu Lys Lys Glu Val Ser Glu Thr Gln His Gly Thr Ile
         35                  40                  45 ctc att aag gtt gag tac aaa ggg gaa gat gca ccc tgc aag att cct       252
Leu Ile Lys Val Glu Tyr Lys Gly Glu Asp Ala Pro Cys Lys Ile Pro
 50                  55                  60 ttc tcc acg gag gat gga caa ggg aaa gct cac aat ggt aga ctg atc       300
Phe Ser Thr Glu Asp Gly Gln Gly Lys Ala His Asn Gly Arg Leu Ile
 65                  70                  75 aca gcc aac cca gtg gtg acc aag aag gag gag cct gtc aac att gag       348
Thr Ala Asn Pro Val Val Thr Lys Lys Glu Glu Pro Val Asn Ile Glu
80                  85                  90                  95 gct gaa cct cct ttt ggg gaa agt aac ata gtg att gga att gga gac       396
Ala Glu Pro Pro Phe Gly Glu Ser Asn Ile Val Ile Gly Ile Gly Asp
                100                 105                 110 aaa gcc ttg aaa atc aac tgg tac aag aag gga agc tcg att ggg aag       444
Lys Ala Leu Lys Ile Asn Trp Tyr Lys Lys Gly Ser Ser Ile Gly Lys
            115                 120                 125 act agt ggg gtt ctg gaa aac cgg gct gct cag ggc gat att act gca       492
Thr Ser Gly Val Leu Glu Asn Arg Ala Ala Gln Gly Asp Ile Thr Ala
        130                 135                 140 ccc ggc ggt gct cgc cgt tta acg ggt gat cag act gcc gct ctg cgt       540
Pro Gly Gly Ala Arg Arg Leu Thr Gly Asp Gln Thr Ala Ala Leu Arg
    145                 150                 155 gat tct ctt agc gat aaa cct gca aaa aat att att ttg ctg att ggc       588
Asp Ser Leu Ser Asp Lys Pro Ala Lys Asn Ile Ile Leu Leu Ile Gly
160                 165                 170                 175 gat ggg atg ggg gac tcg gaa att act gcc gca cgt aat tat gcc gaa       636
Asp Gly Met Gly Asp Ser Glu Ile Thr Ala Ala Arg Asn Tyr Ala Glu
                180                 185                 190 ggt gcg ggc ggc ttt ttt aaa ggt ata gat gcc tta ccg ctt acc ggg       684
Gly Ala Gly Gly Phe Phe Lys Gly Ile Asp Ala Leu Pro Leu Thr Gly
            195                 200                 205 caa tac act cac tat gcg ctg aat aaa aaa acc ggc aaa ccg gac tac       732
Gln Tyr Thr His Tyr Ala Leu Asn Lys Lys Thr Gly Lys Pro Asp Tyr
        210                 215                 220 gtc acc gac tcg gct gca tca gca acc gcc tgg tca acc ggt gtc aaa       780
Val Thr Asp Ser Ala Ala Ser Ala Thr Ala Trp Ser Thr Gly Val Lys
    225                 230                 235 acc tat aac ggc gcg ctg ggc gtc gat att cac gaa aaa gat cac cca       828
Thr Tyr Asn Gly Ala Leu Gly Val Asp Ile His Glu Lys Asp His Pro
240                 245                 250                 255 acg att ctg gaa atg gca aaa gcc gca ggt ctg gcg acc ggt aac gtt       876
Thr Ile Leu Glu Met Ala Lys Ala Ala Gly Leu Ala Thr Gly Asn Val
                260                 265                 270 tct acc gca gag ttg cag ggt gcc acg ccc gct gcg ctg gtg gca cat       924
Ser Thr Ala Glu Leu Gln Gly Ala Thr Pro Ala Ala Leu Val Ala His
            275                 280                 285 gtg acc tcg cgc aaa tgc tac ggt ccg agc gcg acc agt gaa aaa tgt       972
Val Thr Ser Arg Lys Cys Tyr Gly Pro Ser Ala Thr Ser Glu Lys Cys
        290                 295                 300 ccg ggt aac gct ctg gaa aaa ggc gga aaa gga tcg att acc gaa cag      1020
Pro Gly Asn Ala Leu Glu Lys Gly Gly Lys Gly Ser Ile Thr Glu Gln
    305                 310                 315 ctg ctt aac gct cgt gcc gac gtt acg ctt ggc ggc ggc gca aaa acc      1068
Leu Leu Asn Ala Arg Ala Asp Val Thr Leu Gly Gly Gly Ala Lys Thr
320                 325                 330                 335 ttt gct gaa acg gca acc gct ggt gaa tgg cag gga aaa acg ctg cgt      1116
Phe Ala Glu Thr Ala Thr Ala Gly Glu Trp Gln Gly Lys Thr Leu Arg
```

```
                          340                 345                 350
gaa cag gca cag gcg cgt ggt tat cag ttg gtg agc gat gct gcc tca      1164
Glu Gln Ala Gln Ala Arg Gly Tyr Gln Leu Val Ser Asp Ala Ala Ser
            355                 360                 365 ctg aat tcg gtg acg gaa gcg aat cag caa aaa ccc ctg ctt ggc ctg      1212
Leu Asn Ser Val Thr Glu Ala Asn Gln Gln Lys Pro Leu Leu Gly Leu
        370                 375                 380 ttt gct gac ggc aat atg cca gtg cgc tgg cta gga ccg aaa gca acg      1260
Phe Ala Asp Gly Asn Met Pro Val Arg Trp Leu Gly Pro Lys Ala Thr
    385                 390                 395 tac cat ggc aat atc gat aag ccc gca gtc acc tgt acg cca aat ccg      1308
Tyr His Gly Asn Ile Asp Lys Pro Ala Val Thr Cys Thr Pro Asn Pro
400                 405                 410                 415 caa cgt aat gac agt gta cca acc ctg gcg cag atg acc gac aaa gcc      1356
Gln Arg Asn Asp Ser Val Pro Thr Leu Ala Gln Met Thr Asp Lys Ala
                420                 425                 430 att gaa ttg ttg agt aaa aat gag aaa ggc ttt ttc ctg caa gtt gaa      1404
Ile Glu Leu Leu Ser Lys Asn Glu Lys Gly Phe Phe Leu Gln Val Glu
            435                 440                 445 ggt gcg tca atc gat aaa cag aat cat gct gcg aat cct tgt ggg caa      1452
Gly Ala Ser Ile Asp Lys Gln Asn His Ala Ala Asn Pro Cys Gly Gln
        450                 455                 460 att ggc gag acg gtc gat ctc gat gaa gcc gta caa cgg gcg ctg gaa      1500
Ile Gly Glu Thr Val Asp Leu Asp Glu Ala Val Gln Arg Ala Leu Glu
    465                 470                 475 ttc gct aaa aag gag ggt aac acg ctg gtc ata gtc acc gct gat cac      1548
Phe Ala Lys Lys Glu Gly Asn Thr Leu Val Ile Val Thr Ala Asp His
480                 485                 490                 495 gcc cac gcc agc cag att gtt gcg ccg gat acc aaa gct ccg ggc ctc      1596
Ala His Ala Ser Gln Ile Val Ala Pro Asp Thr Lys Ala Pro Gly Leu
                500                 505                 510 acc cag gcg cta aat acc aaa gat ggc gca gtg atg gtg atg agt tac      1644
Thr Gln Ala Leu Asn Thr Lys Asp Gly Ala Val Met Val Met Ser Tyr
            515                 520                 525 ggg aac tcc gaa gag gat tca caa gaa cat acc ggc agt cag ttg cgt      1692
Gly Asn Ser Glu Glu Asp Ser Gln Glu His Thr Gly Ser Gln Leu Arg
        530                 535                 540 att gcg gcg tat ggc ccg cat gcc gcc aat gtt gtt gga ctg acc gac      1740
Ile Ala Ala Tyr Gly Pro His Ala Ala Asn Val Val Gly Leu Thr Asp
    545                 550                 555 cag acc gat ctc ttc tac acc atg aaa gcc gct ctg ggg ctg aaa taa      1788
Gln Thr Asp Leu Phe Tyr Thr Met Lys Ala Ala Leu Gly Leu Lys
560                 565                 570

<210> SEQ ID NO 6
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Arg Thr Pro Glu Met Pro Val Glu His His His His His Asp Asp
1               5                   10                  15

Asp Asp Lys Val Asp Lys Gly Met Ser Tyr Ala Met Cys Leu Asn Thr
                20                  25                  30

Phe Val Leu Lys Lys Glu Val Ser Glu Thr Gln His Gly Thr Ile Leu
            35                  40                  45

Ile Lys Val Glu Tyr Lys Gly Glu Asp Ala Pro Cys Lys Ile Pro Phe
        50                  55                  60
```

-continued

Ser Thr Glu Asp Gly Gln Gly Lys Ala His Asn Gly Arg Leu Ile Thr
 65                  70                  75                  80

Ala Asn Pro Val Val Thr Lys Lys Glu Glu Pro Val Asn Ile Glu Ala
                 85                  90                  95

Glu Pro Pro Phe Gly Glu Ser Asn Ile Val Ile Gly Ile Gly Asp Lys
            100                 105                 110

Ala Leu Lys Ile Asn Trp Tyr Lys Lys Gly Ser Ser Ile Gly Lys Thr
        115                 120                 125

Ser Gly Val Leu Glu Asn Arg Ala Ala Gln Gly Asp Ile Thr Ala Pro
    130                 135                 140

Gly Gly Ala Arg Arg Leu Thr Gly Asp Gln Thr Ala Ala Leu Arg Asp
145                 150                 155                 160

Ser Leu Ser Asp Lys Pro Ala Lys Asn Ile Ile Leu Leu Ile Gly Asp
                165                 170                 175

Gly Met Gly Asp Ser Glu Ile Thr Ala Ala Arg Asn Tyr Ala Glu Gly
            180                 185                 190

Ala Gly Gly Phe Phe Lys Gly Ile Asp Ala Leu Pro Leu Thr Gly Gln
        195                 200                 205

Tyr Thr His Tyr Ala Leu Asn Lys Lys Thr Gly Lys Pro Asp Tyr Val
    210                 215                 220

Thr Asp Ser Ala Ala Ser Ala Thr Ala Trp Ser Thr Gly Val Lys Thr
225                 230                 235                 240

Tyr Asn Gly Ala Leu Gly Val Asp Ile His Glu Lys Asp His Pro Thr
                245                 250                 255

Ile Leu Glu Met Ala Lys Ala Ala Gly Leu Ala Thr Gly Asn Val Ser
            260                 265                 270

Thr Ala Glu Leu Gln Gly Ala Thr Pro Ala Ala Leu Val Ala His Val
        275                 280                 285

Thr Ser Arg Lys Cys Tyr Gly Pro Ser Ala Thr Ser Glu Lys Cys Pro
    290                 295                 300

Gly Asn Ala Leu Glu Lys Gly Gly Lys Gly Ser Ile Thr Glu Gln Leu
305                 310                 315                 320

Leu Asn Ala Arg Ala Asp Val Thr Leu Gly Gly Gly Ala Lys Thr Phe
                325                 330                 335

Ala Glu Thr Ala Thr Ala Gly Glu Trp Gln Gly Lys Thr Leu Arg Glu
            340                 345                 350

Gln Ala Gln Ala Arg Gly Tyr Gln Leu Val Ser Asp Ala Ala Ser Leu
        355                 360                 365

Asn Ser Val Thr Glu Ala Asn Gln Gln Lys Pro Leu Leu Gly Leu Phe
    370                 375                 380

Ala Asp Gly Asn Met Pro Val Arg Trp Leu Gly Pro Lys Ala Thr Tyr
385                 390                 395                 400

His Gly Asn Ile Asp Lys Pro Ala Val Thr Cys Thr Pro Asn Pro Gln
                405                 410                 415

Arg Asn Asp Ser Val Pro Thr Leu Ala Gln Met Thr Asp Lys Ala Ile
            420                 425                 430

Glu Leu Leu Ser Lys Asn Glu Lys Gly Phe Phe Leu Gln Val Glu Gly
        435                 440                 445

Ala Ser Ile Asp Lys Gln Asn His Ala Ala Asn Pro Cys Gly Gln Ile
    450                 455                 460

Gly Glu Thr Val Asp Leu Asp Glu Ala Val Gln Arg Ala Leu Glu Phe
465                 470                 475                 480

Ala Lys Lys Glu Gly Asn Thr Leu Val Ile Val Thr Ala Asp His Ala

```
                        485                 490                 495
His Ala Ser Gln Ile Val Ala Pro Asp Thr Lys Ala Pro Gly Leu Thr
                500                 505                 510

Gln Ala Leu Asn Thr Lys Asp Gly Ala Val Met Val Met Ser Tyr Gly
            515                 520                 525

Asn Ser Glu Glu Asp Ser Gln Glu His Thr Gly Ser Gln Leu Arg Ile
        530                 535                 540

Ala Ala Tyr Gly Pro His Ala Ala Asn Val Val Gly Leu Thr Asp Gln
545                 550                 555                 560

Thr Asp Leu Phe Tyr Thr Met Lys Ala Ala Leu Gly Leu Lys
                565                 570

<210> SEQ ID NO 7
<211> LENGTH: 1788
<212> TYPE: DNA
<213> ORGANISM: Artificial Sequence
<220> FEATURE:
<223> OTHER INFORMATION: Description of Artificial Sequence: Synthetic
      DNA encoding H6-ED3.DEN4-PhoA gene (from pEBL14)
<220> FEATURE:
<221> NAME/KEY: sig_peptide
<222> LOCATION: (1)..(63)
<220> FEATURE:
<221> NAME/KEY: CDS
<222> LOCATION: (64)..(1785)
<223> OTHER INFORMATION: H6-ED3.DEN4-PhoA (88-105 = His-tag; 127-444 =
      ED3.DEN4; 64-81 and 454-1788 = PhoA)

<400> SEQUENCE: 7
gtgaaacaaa gcactattgc actggcactc ttaccgttac tgtttacccc tgtgacaaaa       60 gcc cgg aca cca gaa atg ccc gtc gaa cat cac cat cac cat cac gac      108
Arg Thr Pro Glu Met Pro Val Glu His His His His His His Asp
  1               5                  10                  15 gat gac gat aag gtc gac aaa gga atg tca tac acg atg tgc tca gga      156
Asp Asp Asp Lys Val Asp Lys Gly Met Ser Tyr Thr Met Cys Ser Gly
                 20                  25                  30 aag ttc tca att gat aaa gag atg gca gaa aca cag cat ggg aca aca      204
Lys Phe Ser Ile Asp Lys Glu Met Ala Glu Thr Gln His Gly Thr Thr
             35                  40                  45 gtg gtg aaa gtc aag tat gag ggt gct gga gct cca tgt aaa gtt ccc      252
Val Val Lys Val Lys Tyr Glu Gly Ala Gly Ala Pro Cys Lys Val Pro
         50                  55                  60 ata gag ata aga gat gtg aac aag gaa aaa gtg gtt ggg cgt atc atc      300
Ile Glu Ile Arg Asp Val Asn Lys Glu Lys Val Val Gly Arg Ile Ile
     65                  70                  75 tca tct acc cct ttt gct gag aat acc aat agt gtg acc aat ata gaa      348
Ser Ser Thr Pro Phe Ala Glu Asn Thr Asn Ser Val Thr Asn Ile Glu
 80                  85                  90                  95 ttg gaa ccc cct ttt ggg gat agc tac ata gta ata ggt gta gga gac      396
Leu Glu Pro Pro Phe Gly Asp Ser Tyr Ile Val Ile Gly Val Gly Asp
                100                 105                 110 agt gca tta aca ctc cat tgg ttc agg aaa ggg agt tcc att ggc aag      444
Ser Ala Leu Thr Leu His Trp Phe Arg Lys Gly Ser Ser Ile Gly Lys
            115                 120                 125 act agt ggg gtt ctg gaa aac cgg gct gct cag ggc gat att act gca      492
Thr Ser Gly Val Leu Glu Asn Arg Ala Ala Gln Gly Asp Ile Thr Ala
        130                 135                 140 ccc ggc ggt gct cgc cgt tta acg ggt gat cag act gcc gct ctg cgt      540
Pro Gly Gly Ala Arg Arg Leu Thr Gly Asp Gln Thr Ala Ala Leu Arg
    145                 150                 155 gat tct ctt agc gat aaa cct gca aaa aat att att ttg ctg att ggc      588
Asp Ser Leu Ser Asp Lys Pro Ala Lys Asn Ile Ile Leu Leu Ile Gly
```

```
                160                 165                 170                 175
gat ggg atg ggg gac tcg gaa att act gcc gca cgt aat tat gcc gaa      636
Asp Gly Met Gly Asp Ser Glu Ile Thr Ala Ala Arg Asn Tyr Ala Glu
                    180                 185                 190 ggt gcg ggc ggc ttt ttt aaa ggt ata gat gcc tta ccg ctt acc ggg      684
Gly Ala Gly Gly Phe Phe Lys Gly Ile Asp Ala Leu Pro Leu Thr Gly
            195                 200                 205 caa tac act cac tat gcg ctg aat aaa aaa acc ggc aaa ccg gac tac      732
Gln Tyr Thr His Tyr Ala Leu Asn Lys Lys Thr Gly Lys Pro Asp Tyr
        210                 215                 220 gtc acc gac tcg gct gca tca gca acc gcc tgg tca acc ggt gtc aaa      780
Val Thr Asp Ser Ala Ala Ser Ala Thr Ala Trp Ser Thr Gly Val Lys
    225                 230                 235 acc tat aac ggc gcg ctg ggc gtc gat att cac gaa aaa gat cac cca      828
Thr Tyr Asn Gly Ala Leu Gly Val Asp Ile His Glu Lys Asp His Pro
240                 245                 250                 255 acg att ctg gaa atg gca aaa gcc gca ggt ctg gcg acc ggt aac gtt      876
Thr Ile Leu Glu Met Ala Lys Ala Ala Gly Leu Ala Thr Gly Asn Val
                260                 265                 270 tct acc gca gag ttg cag ggt gcc acg ccc gct gcg ctg gtg gca cat      924
Ser Thr Ala Glu Leu Gln Gly Ala Thr Pro Ala Ala Leu Val Ala His
            275                 280                 285 gtg acc tcg cgc aaa tgc tac ggt ccg agc gcg acc agt gaa aaa tgt      972
Val Thr Ser Arg Lys Cys Tyr Gly Pro Ser Ala Thr Ser Glu Lys Cys
        290                 295                 300 ccg ggt aac gct ctg gaa aaa ggc gga aaa gga tcg att acc gaa cag     1020
Pro Gly Asn Ala Leu Glu Lys Gly Gly Lys Gly Ser Ile Thr Glu Gln
    305                 310                 315 ctg ctt aac gct cgt gcc gac gtt acg ctt ggc ggc ggc gca aaa acc     1068
Leu Leu Asn Ala Arg Ala Asp Val Thr Leu Gly Gly Gly Ala Lys Thr
320                 325                 330                 335 ttt gct gaa acg gca acc gct ggt gaa tgg cag gga aaa acg ctg cgt     1116
Phe Ala Glu Thr Ala Thr Ala Gly Glu Trp Gln Gly Lys Thr Leu Arg
                340                 345                 350 gaa cag gca cag gcg cgt ggt tat cag ttg gtg agc gat gct gcc tca     1164
Glu Gln Ala Gln Ala Arg Gly Tyr Gln Leu Val Ser Asp Ala Ala Ser
            355                 360                 365 ctg aat tcg gtg acg gaa gcg aat cag caa aaa ccc ctg ctt ggc ctg     1212
Leu Asn Ser Val Thr Glu Ala Asn Gln Gln Lys Pro Leu Leu Gly Leu
        370                 375                 380 ttt gct gac ggc aat atg cca gtg cgc tgg cta gga ccg aaa gca acg     1260
Phe Ala Asp Gly Asn Met Pro Val Arg Trp Leu Gly Pro Lys Ala Thr
    385                 390                 395 tac cat ggc aat atc gat aag ccc gca gtc acc tgt acg cca aat ccg     1308
Tyr His Gly Asn Ile Asp Lys Pro Ala Val Thr Cys Thr Pro Asn Pro
400                 405                 410                 415 caa cgt aat gac agt gta cca acc ctg gcg cag atg acc gac aaa gcc     1356
Gln Arg Asn Asp Ser Val Pro Thr Leu Ala Gln Met Thr Asp Lys Ala
                420                 425                 430 att gaa ttg ttg agt aaa aat gag aaa ggc ttt ttc ctg caa gtt gaa     1404
Ile Glu Leu Leu Ser Lys Asn Glu Lys Gly Phe Phe Leu Gln Val Glu
            435                 440                 445 ggt gcg tca atc gat aaa cag aat cat gct gcg aat cct tgt ggg caa     1452
Gly Ala Ser Ile Asp Lys Gln Asn His Ala Ala Asn Pro Cys Gly Gln
        450                 455                 460 att ggc gag acg gtc gat ctc gat gaa gcc gta caa cgg gcg ctg gaa     1500
Ile Gly Glu Thr Val Asp Leu Asp Glu Ala Val Gln Arg Ala Leu Glu
    465                 470                 475 ttc gct aaa aag gag ggt aac acg ctg gtc ata gtc acc gct gat cac     1548
Phe Ala Lys Lys Glu Gly Asn Thr Leu Val Ile Val Thr Ala Asp His
```

```
                480             485             490             495
gcc cac gcc agc cag att gtt gcg ccg gat acc aaa gct ccg ggc ctc     1596
Ala His Ala Ser Gln Ile Val Ala Pro Asp Thr Lys Ala Pro Gly Leu
                500                 505                 510 acc cag gcg cta aat acc aaa gat ggc gca gtg atg gtg atg agt tac     1644
Thr Gln Ala Leu Asn Thr Lys Asp Gly Ala Val Met Val Met Ser Tyr
                515                 520                 525 ggg aac tcc gaa gag gat tca caa gaa cat acc ggc agt cag ttg cgt     1692
Gly Asn Ser Glu Glu Asp Ser Gln Glu His Thr Gly Ser Gln Leu Arg
            530                 535                 540 att gcg gcg tat ggc ccg cat gcc gcc aat gtt gtt gga ctg acc gac     1740
Ile Ala Ala Tyr Gly Pro His Ala Ala Asn Val Val Gly Leu Thr Asp
        545                 550                 555 cag acc gat ctc ttc tac acc atg aaa gcc gct ctg ggg ctg aaa taa    1788
Gln Thr Asp Leu Phe Tyr Thr Met Lys Ala Ala Leu Gly Leu Lys
560                 565                 570

<210> SEQ ID NO 8
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Arg Thr Pro Glu Met Pro Val Glu His His His His His His Asp Asp
1               5                   10                  15

Asp Asp Lys Val Asp Lys Gly Met Ser Tyr Thr Met Cys Ser Gly Lys
            20                  25                  30

Phe Ser Ile Asp Lys Glu Met Ala Glu Thr Gln His Gly Thr Thr Val
        35                  40                  45

Val Lys Val Lys Tyr Glu Gly Ala Gly Ala Pro Cys Lys Val Pro Ile
    50                  55                  60

Glu Ile Arg Asp Val Asn Lys Glu Lys Val Val Gly Arg Ile Ile Ser
65                  70                  75                  80

Ser Thr Pro Phe Ala Glu Asn Thr Asn Ser Val Thr Asn Ile Glu Leu
                85                  90                  95

Glu Pro Pro Phe Gly Asp Ser Tyr Ile Val Ile Gly Val Gly Asp Ser
            100                 105                 110

Ala Leu Thr Leu His Trp Phe Arg Lys Gly Ser Ser Ile Gly Lys Thr
        115                 120                 125

Ser Gly Val Leu Glu Asn Arg Ala Ala Gln Gly Asp Ile Thr Ala Pro
    130                 135                 140

Gly Gly Ala Arg Arg Leu Thr Gly Asp Gln Thr Ala Ala Leu Arg Asp
145                 150                 155                 160

Ser Leu Ser Asp Lys Pro Ala Lys Asn Ile Ile Leu Leu Ile Gly Asp
                165                 170                 175

Gly Met Gly Asp Ser Glu Ile Thr Ala Ala Arg Asn Tyr Ala Glu Gly
            180                 185                 190

Ala Gly Gly Phe Phe Lys Gly Ile Asp Ala Leu Pro Leu Thr Gly Gln
        195                 200                 205

Tyr Thr His Tyr Ala Leu Asn Lys Lys Thr Gly Lys Pro Asp Tyr Val
    210                 215                 220

Thr Asp Ser Ala Ala Ser Ala Thr Ala Trp Ser Thr Gly Val Lys Thr
225                 230                 235                 240

Tyr Asn Gly Ala Leu Gly Val Asp Ile His Glu Lys Asp His Pro Thr
                245                 250                 255
```

Ile Leu Glu Met Ala Lys Ala Ala Gly Leu Ala Thr Gly Asn Val Ser
            260                 265                 270

Thr Ala Glu Leu Gln Gly Ala Thr Pro Ala Ala Leu Val Ala His Val
        275                 280                 285

Thr Ser Arg Lys Cys Tyr Gly Pro Ser Ala Thr Ser Glu Lys Cys Pro
    290                 295                 300

Gly Asn Ala Leu Glu Lys Gly Lys Gly Ser Ile Thr Glu Gln Leu
305                 310                 315                 320

Leu Asn Ala Arg Ala Asp Val Thr Leu Gly Gly Gly Ala Lys Thr Phe
                325                 330                 335

Ala Glu Thr Ala Thr Ala Gly Glu Trp Gln Gly Lys Thr Leu Arg Glu
            340                 345                 350

Gln Ala Gln Ala Arg Gly Tyr Gln Leu Val Ser Asp Ala Ala Ser Leu
        355                 360                 365

Asn Ser Val Thr Glu Ala Asn Gln Gln Lys Pro Leu Leu Gly Leu Phe
    370                 375                 380

Ala Asp Gly Asn Met Pro Val Arg Trp Leu Gly Pro Lys Ala Thr Tyr
385                 390                 395                 400

His Gly Asn Ile Asp Lys Pro Ala Val Thr Cys Thr Pro Asn Pro Gln
                405                 410                 415

Arg Asn Asp Ser Val Pro Thr Leu Ala Gln Met Thr Asp Lys Ala Ile
            420                 425                 430

Glu Leu Leu Ser Lys Asn Glu Lys Gly Phe Phe Leu Gln Val Glu Gly
        435                 440                 445

Ala Ser Ile Asp Lys Gln Asn His Ala Ala Asn Pro Cys Gly Gln Ile
    450                 455                 460

Gly Glu Thr Val Asp Leu Asp Glu Ala Val Gln Arg Ala Leu Glu Phe
465                 470                 475                 480

Ala Lys Lys Glu Gly Asn Thr Leu Val Ile Val Thr Ala Asp His Ala
                485                 490                 495

His Ala Ser Gln Ile Val Ala Pro Asp Thr Lys Ala Pro Gly Leu Thr
            500                 505                 510

Gln Ala Leu Asn Thr Lys Asp Gly Ala Val Met Val Met Ser Tyr Gly
        515                 520                 525

Asn Ser Glu Glu Asp Ser Gln Glu His Thr Gly Ser Gln Leu Arg Ile
    530                 535                 540

Ala Ala Tyr Gly Pro His Ala Ala Asn Val Val Gly Leu Thr Asp Gln
545                 550                 555                 560

Thr Asp Leu Phe Tyr Thr Met Lys Ala Ala Leu Gly Leu Lys
                565                 570

<210> SEQ ID NO 9
<211> LENGTH: 1797
<212> TYPE: DNA
<213> ORGANISM: Artificial Sequence
<220> FEATURE:
<223> OTHER INFORMATION: Description of Artificial Sequence: Synthetic
    DNA encoding H6-ED3.WN-PhoA gene (from pEBL15)
<220> FEATURE:
<221> NAME/KEY: sig_peptide
<222> LOCATION: (1)..(63)
<220> FEATURE:
<221> NAME/KEY: CDS
<222> LOCATION: (64)..(1794)
<223> OTHER INFORMATION: H6-ED3.WN-PhoA (88-105 = His-tag; 127-453 =
    ED3.WN; 64-81 and 463-1797 = PhoA)

<400> SEQUENCE: 9

```
gtgaaacaaa gcactattgc actggcactc ttaccgttac tgtttacccc tgtgacaaaa      60
```

| | | | | | | | | | | | | | | | | |
|---|---|---|---|---|---|---|---|---|---|---|---|---|---|---|---|---|
| gcc | cgg | aca | cca | gaa | atg | ccc | gtc | gaa | cat | cac | cat | cac | cat | cac | gac | 108 |
| Arg | Thr | Pro | Glu | Met | Pro | Val | Glu | His | His | His | His | His | His | Asp | |
| 1 | | | | 5 | | | | | 10 | | | | | 15 | | |

| gat | gac | gat | aag | gtc | gac | aaa | gga | aca | acc | tat | ggc | gtc | tgt | tca | aag | 156 |
|---|---|---|---|---|---|---|---|---|---|---|---|---|---|---|---|---|
| Asp | Asp | Asp | Lys | Val | Asp | Lys | Gly | Thr | Thr | Tyr | Gly | Val | Cys | Ser | Lys | |
| | | | 20 | | | | | 25 | | | | | 30 | | | |

| gct | ttc | aag | ttt | ctt | ggg | act | ccc | gca | gac | aca | ggt | cac | ggc | act | gtg | 204 |
|---|---|---|---|---|---|---|---|---|---|---|---|---|---|---|---|---|
| Ala | Phe | Lys | Phe | Leu | Gly | Thr | Pro | Ala | Asp | Thr | Gly | His | Gly | Thr | Val | |
| | | 35 | | | | | 40 | | | | | 45 | | | | |

| gtg | ttg | gaa | ttg | cag | tac | act | ggc | acg | gat | gga | cct | tgc | aaa | gtt | cct | 252 |
|---|---|---|---|---|---|---|---|---|---|---|---|---|---|---|---|---|
| Val | Leu | Glu | Leu | Gln | Tyr | Thr | Gly | Thr | Asp | Gly | Pro | Cys | Lys | Val | Pro | |
| 50 | | | | | 55 | | | | | 60 | | | | | | |

| atc | tcg | tca | gtg | gct | tca | ttg | aac | gac | cta | acg | cca | gtg | ggc | aga | ttg | 300 |
|---|---|---|---|---|---|---|---|---|---|---|---|---|---|---|---|---|
| Ile | Ser | Ser | Val | Ala | Ser | Leu | Asn | Asp | Leu | Thr | Pro | Val | Gly | Arg | Leu | |
| 65 | | | | | 70 | | | | | 75 | | | | | | |

| gtc | act | gtc | aac | cct | ttt | gtt | tca | gtg | gcc | acg | gcc | aac | gct | aag | gtc | 348 |
|---|---|---|---|---|---|---|---|---|---|---|---|---|---|---|---|---|
| Val | Thr | Val | Asn | Pro | Phe | Val | Ser | Val | Ala | Thr | Ala | Asn | Ala | Lys | Val | |
| 80 | | | | 85 | | | | | 90 | | | | | 95 | | |

| ctg | att | gaa | ttg | gaa | cca | ccc | ttt | gga | gac | tca | tac | ata | gtg | gtg | ggc | 396 |
|---|---|---|---|---|---|---|---|---|---|---|---|---|---|---|---|---|
| Leu | Ile | Glu | Leu | Glu | Pro | Pro | Phe | Gly | Asp | Ser | Tyr | Ile | Val | Val | Gly | |
| | | | 100 | | | | | 105 | | | | | 110 | | | |

| aga | gga | gaa | caa | cag | att | aat | cac | cat | tgg | cac | aag | tct | ggt | agc | agc | 444 |
|---|---|---|---|---|---|---|---|---|---|---|---|---|---|---|---|---|
| Arg | Gly | Glu | Gln | Gln | Ile | Asn | His | His | Trp | His | Lys | Ser | Gly | Ser | Ser | |
| | | 115 | | | | | 120 | | | | | 125 | | | | |

| att | ggc | aaa | act | agt | ggg | gtt | ctg | gaa | aac | cgg | gct | gct | cag | ggc | gat | 492 |
|---|---|---|---|---|---|---|---|---|---|---|---|---|---|---|---|---|
| Ile | Gly | Lys | Thr | Ser | Gly | Val | Leu | Glu | Asn | Arg | Ala | Ala | Gln | Gly | Asp | |
| | | 130 | | | | | 135 | | | | | 140 | | | | |

| att | act | gca | ccc | ggc | ggt | gct | cgc | cgt | tta | acg | ggt | gat | cag | act | gcc | 540 |
|---|---|---|---|---|---|---|---|---|---|---|---|---|---|---|---|---|
| Ile | Thr | Ala | Pro | Gly | Gly | Ala | Arg | Arg | Leu | Thr | Gly | Asp | Gln | Thr | Ala | |
| 145 | | | | | 150 | | | | | 155 | | | | | | |

| gct | ctg | cgt | gat | tct | ctt | agc | gat | aaa | cct | gca | aaa | aat | att | att | ttg | 588 |
|---|---|---|---|---|---|---|---|---|---|---|---|---|---|---|---|---|
| Ala | Leu | Arg | Asp | Ser | Leu | Ser | Asp | Lys | Pro | Ala | Lys | Asn | Ile | Ile | Leu | |
| 160 | | | | 165 | | | | | 170 | | | | | 175 | | |

| ctg | att | ggc | gat | ggg | atg | ggg | gac | tcg | gaa | att | act | gcc | gca | cgt | aat | 636 |
|---|---|---|---|---|---|---|---|---|---|---|---|---|---|---|---|---|
| Leu | Ile | Gly | Asp | Gly | Met | Gly | Asp | Ser | Glu | Ile | Thr | Ala | Ala | Arg | Asn | |
| | | | 180 | | | | | 185 | | | | | 190 | | | |

| tat | gcc | gaa | ggt | gcg | ggc | ggc | ttt | ttt | aaa | ggt | ata | gat | gcc | tta | ccg | 684 |
|---|---|---|---|---|---|---|---|---|---|---|---|---|---|---|---|---|
| Tyr | Ala | Glu | Gly | Ala | Gly | Gly | Phe | Phe | Lys | Gly | Ile | Asp | Ala | Leu | Pro | |
| | | 195 | | | | | 200 | | | | | 205 | | | | |

| ctt | acc | ggg | caa | tac | act | cac | tat | gcg | ctg | aat | aaa | aaa | acc | ggc | aaa | 732 |
|---|---|---|---|---|---|---|---|---|---|---|---|---|---|---|---|---|
| Leu | Thr | Gly | Gln | Tyr | Thr | His | Tyr | Ala | Leu | Asn | Lys | Lys | Thr | Gly | Lys | |
| | | 210 | | | | | 215 | | | | | 220 | | | | |

| ccg | gac | tac | gtc | acc | gac | tcg | gct | gca | tca | gca | acc | gcc | tgg | tca | acc | 780 |
|---|---|---|---|---|---|---|---|---|---|---|---|---|---|---|---|---|
| Pro | Asp | Tyr | Val | Thr | Asp | Ser | Ala | Ala | Ser | Ala | Thr | Ala | Trp | Ser | Thr | |
| 225 | | | | | 230 | | | | | 235 | | | | | | |

| ggt | gtc | aaa | acc | tat | aac | ggc | gcg | ctg | ggc | gtc | gat | att | cac | gaa | aaa | 828 |
|---|---|---|---|---|---|---|---|---|---|---|---|---|---|---|---|---|
| Gly | Val | Lys | Thr | Tyr | Asn | Gly | Ala | Leu | Gly | Val | Asp | Ile | His | Glu | Lys | |
| 240 | | | | 245 | | | | | 250 | | | | | 255 | | |

| gat | cac | cca | acg | att | ctg | gaa | atg | gca | aaa | gcc | gca | ggt | ctg | gcg | acc | 876 |
|---|---|---|---|---|---|---|---|---|---|---|---|---|---|---|---|---|
| Asp | His | Pro | Thr | Ile | Leu | Glu | Met | Ala | Lys | Ala | Ala | Gly | Leu | Ala | Thr | |
| | | | 260 | | | | | 265 | | | | | 270 | | | |

| ggt | aac | gtt | tct | acc | gca | gag | ttg | cag | ggt | gcc | acg | ccc | gct | gcg | ctg | 924 |
|---|---|---|---|---|---|---|---|---|---|---|---|---|---|---|---|---|
| Gly | Asn | Val | Ser | Thr | Ala | Glu | Leu | Gln | Gly | Ala | Thr | Pro | Ala | Ala | Leu | |
| | | | 275 | | | | | 280 | | | | | 285 | | | |

| gtg | gca | cat | gtg | acc | tcg | cgc | aaa | tgc | tac | ggt | ccg | agc | gcg | acc | agt | 972 |
|---|---|---|---|---|---|---|---|---|---|---|---|---|---|---|---|---|
| Val | Ala | His | Val | Thr | Ser | Arg | Lys | Cys | Tyr | Gly | Pro | Ser | Ala | Thr | Ser | |
| | | | 290 | | | | | 295 | | | | | 300 | | | |

| gaa | aaa | tgt | ccg | ggt | aac | gct | ctg | gaa | aaa | ggc | gga | aaa | gga | tcg | att | 1020 |
|---|---|---|---|---|---|---|---|---|---|---|---|---|---|---|---|---|
| Glu | Lys | Cys | Pro | Gly | Asn | Ala | Leu | Glu | Lys | Gly | Gly | Lys | Gly | Ser | Ile | |

```
           305                 310                 315
acc gaa cag ctg ctt aac gct cgt gcc gac gtt acg ctt ggc ggc ggc    1068
Thr Glu Gln Leu Leu Asn Ala Arg Ala Asp Val Thr Leu Gly Gly Gly
320                 325                 330                 335 gca aaa acc ttt gct gaa acg gca acc gct ggt gaa tgg cag gga aaa    1116
Ala Lys Thr Phe Ala Glu Thr Ala Thr Ala Gly Glu Trp Gln Gly Lys
                340                 345                 350 acg ctg cgt gaa cag gca cag gcg cgt ggt tat cag ttg gtg agc gat    1164
Thr Leu Arg Glu Gln Ala Gln Ala Arg Gly Tyr Gln Leu Val Ser Asp
            355                 360                 365 gct gcc tca ctg aat tcg gtg acg gaa gcg aat cag caa aaa ccc ctg    1212
Ala Ala Ser Leu Asn Ser Val Thr Glu Ala Asn Gln Gln Lys Pro Leu
        370                 375                 380 ctt ggc ctg ttt gct gac ggc aat atg cca gtg cgc tgg cta gga ccg    1260
Leu Gly Leu Phe Ala Asp Gly Asn Met Pro Val Arg Trp Leu Gly Pro
385                 390                 395 aaa gca acg tac cat ggc aat atc gat aag ccc gca gtc acc tgt acg    1308
Lys Ala Thr Tyr His Gly Asn Ile Asp Lys Pro Ala Val Thr Cys Thr
400                 405                 410                 415 cca aat ccg caa cgt aat gac agt gta cca acc ctg gcg cag atg acc    1356
Pro Asn Pro Gln Arg Asn Asp Ser Val Pro Thr Leu Ala Gln Met Thr
                420                 425                 430 gac aaa gcc att gaa ttg ttg agt aaa aat gag aaa ggc ttt ttc ctg    1404
Asp Lys Ala Ile Glu Leu Leu Ser Lys Asn Glu Lys Gly Phe Phe Leu
            435                 440                 445 caa gtt gaa ggt gcg tca atc gat aaa cag aat cat gct gcg aat cct    1452
Gln Val Glu Gly Ala Ser Ile Asp Lys Gln Asn His Ala Ala Asn Pro
        450                 455                 460 tgt ggg caa att ggc gag acg gtc gat ctc gat gaa gcc gta caa cgg    1500
Cys Gly Gln Ile Gly Glu Thr Val Asp Leu Asp Glu Ala Val Gln Arg
465                 470                 475 gcg ctg gaa ttc gct aaa aag gag ggt aac acg ctg gtc ata gtc acc    1548
Ala Leu Glu Phe Ala Lys Lys Glu Gly Asn Thr Leu Val Ile Val Thr
480                 485                 490                 495 gct gat cac gcc cac gcc agc cag att gtt gcg ccg gat acc aaa gct    1596
Ala Asp His Ala His Ala Ser Gln Ile Val Ala Pro Asp Thr Lys Ala
                500                 505                 510 ccg ggc ctc acc cag gcg cta aat acc aaa gat ggc gca gtg atg gtg    1644
Pro Gly Leu Thr Gln Ala Leu Asn Thr Lys Asp Gly Ala Val Met Val
            515                 520                 525 atg agt tac ggg aac tcc gaa gag gat tca caa gaa cat acc ggc agt    1692
Met Ser Tyr Gly Asn Ser Glu Glu Asp Ser Gln Glu His Thr Gly Ser
        530                 535                 540 cag ttg cgt att gcg gcg tat ggc ccg cat gcc gcc aat gtt gtt gga    1740
Gln Leu Arg Ile Ala Ala Tyr Gly Pro His Ala Ala Asn Val Val Gly
545                 550                 555 ctg acc gac cag acc gat ctc ttc tac acc atg aaa gcc gct ctg ggg    1788
Leu Thr Asp Gln Thr Asp Leu Phe Tyr Thr Met Lys Ala Ala Leu Gly
560                 565                 570                 575 ctg aaa taa                                                        1797
Leu Lys

<210> SEQ ID NO 10
<211> LENGTH: 577
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10
```

-continued

```
Arg Thr Pro Glu Met Pro Val Glu His His His His His Asp Asp
1               5                   10                  15

Asp Asp Lys Val Asp Lys Gly Thr Thr Tyr Gly Val Cys Ser Lys Ala
            20                  25                  30

Phe Lys Phe Leu Gly Thr Pro Ala Asp Thr Gly His Gly Thr Val Val
        35                  40                  45

Leu Glu Leu Gln Tyr Thr Gly Thr Asp Gly Pro Cys Lys Val Pro Ile
    50                  55                  60

Ser Ser Val Ala Ser Leu Asn Asp Leu Thr Pro Val Gly Arg Leu Val
65                  70                  75                  80

Thr Val Asn Pro Phe Val Ser Val Ala Thr Ala Asn Ala Lys Val Leu
                85                  90                  95

Ile Glu Leu Glu Pro Pro Phe Gly Asp Ser Tyr Ile Val Val Gly Arg
            100                 105                 110

Gly Glu Gln Gln Ile Asn His His Trp His Lys Ser Gly Ser Ser Ile
        115                 120                 125

Gly Lys Thr Ser Gly Val Leu Glu Asn Arg Ala Ala Gln Gly Asp Ile
    130                 135                 140

Thr Ala Pro Gly Gly Ala Arg Arg Leu Thr Gly Asp Gln Thr Ala Ala
145                 150                 155                 160

Leu Arg Asp Ser Leu Ser Asp Lys Pro Ala Lys Asn Ile Ile Leu Leu
                165                 170                 175

Ile Gly Asp Gly Met Gly Asp Ser Glu Ile Thr Ala Ala Arg Asn Tyr
            180                 185                 190

Ala Glu Gly Ala Gly Gly Phe Phe Lys Gly Ile Asp Ala Leu Pro Leu
        195                 200                 205

Thr Gly Gln Tyr Thr His Tyr Ala Leu Asn Lys Lys Thr Gly Lys Pro
    210                 215                 220

Asp Tyr Val Thr Asp Ser Ala Ala Ser Ala Thr Ala Trp Ser Thr Gly
225                 230                 235                 240

Val Lys Thr Tyr Asn Gly Ala Leu Gly Val Asp Ile His Glu Lys Asp
                245                 250                 255

His Pro Thr Ile Leu Glu Met Ala Lys Ala Ala Gly Leu Ala Thr Gly
            260                 265                 270

Asn Val Ser Thr Ala Glu Leu Gln Gly Ala Thr Pro Ala Ala Leu Val
        275                 280                 285

Ala His Val Thr Ser Arg Lys Cys Tyr Gly Pro Ser Ala Thr Ser Glu
    290                 295                 300

Lys Cys Pro Gly Asn Ala Leu Glu Lys Gly Gly Lys Gly Ser Ile Thr
305                 310                 315                 320

Glu Gln Leu Leu Asn Ala Arg Ala Asp Val Thr Leu Gly Gly Gly Ala
                325                 330                 335

Lys Thr Phe Ala Glu Thr Ala Thr Ala Gly Glu Trp Gln Gly Lys Thr
            340                 345                 350

Leu Arg Glu Gln Ala Gln Ala Arg Gly Tyr Gln Leu Val Ser Asp Ala
        355                 360                 365

Ala Ser Leu Asn Ser Val Thr Glu Ala Asn Gln Lys Pro Leu Leu
    370                 375                 380

Gly Leu Phe Ala Asp Gly Asn Met Pro Val Arg Trp Leu Gly Pro Lys
385                 390                 395                 400

Ala Thr Tyr His Gly Asn Ile Asp Lys Pro Ala Val Thr Cys Thr Pro
                405                 410                 415

Asn Pro Gln Arg Asn Asp Ser Val Pro Thr Leu Ala Gln Met Thr Asp
            420                 425                 430
```

```
Lys Ala Ile Glu Leu Leu Ser Lys Asn Glu Lys Gly Phe Phe Leu Gln
            435                 440                 445

Val Glu Gly Ala Ser Ile Asp Lys Gln Asn His Ala Ala Asn Pro Cys
    450                 455                 460

Gly Gln Ile Gly Glu Thr Val Asp Leu Asp Glu Ala Val Gln Arg Ala
465                 470                 475                 480

Leu Glu Phe Ala Lys Lys Glu Gly Asn Thr Leu Val Ile Val Thr Ala
                485                 490                 495

Asp His Ala His Ala Ser Gln Ile Val Ala Pro Asp Thr Lys Ala Pro
                500                 505                 510

Gly Leu Thr Gln Ala Leu Asn Thr Lys Asp Gly Ala Val Met Val Met
            515                 520                 525

Ser Tyr Gly Asn Ser Glu Glu Asp Ser Gln Glu His Thr Gly Ser Gln
            530                 535                 540

Leu Arg Ile Ala Ala Tyr Gly Pro His Ala Ala Asn Val Val Gly Leu
545                 550                 555                 560

Thr Asp Gln Thr Asp Leu Phe Tyr Thr Met Lys Ala Ala Leu Gly Leu
                565                 570                 575

Lys

<210> SEQ ID NO 11
<211> LENGTH: 1788
<212> TYPE: DNA
<213> ORGANISM: Artificial Sequence
<220> FEATURE:
<223> OTHER INFORMATION: Description of Artificial Sequence: Synthetic
      DNA encoding H6-ED3.YF-PhoA gene (from pEBL17)
<220> FEATURE:
<221> NAME/KEY: sig_peptide
<222> LOCATION: (1)..(63)
<220> FEATURE:
<221> NAME/KEY: CDS
<222> LOCATION: (64)..(1785)
<223> OTHER INFORMATION: H6-ED3.YF-PhoA (88-105 = His-tag; 127-444 =
      ED3.YF; 64-81 and 454-1788 = PhoA)

<400> SEQUENCE: 11
gtgaaacaaa gcactattgc actggcactc ttaccgttac tgtttacccc tgtgacaaaa      60 gcc cgg aca cca gaa atg ccc gtc gaa cat cac cat cac cat cac gac       108
Arg Thr Pro Glu Met Pro Val Glu His His His His His His Asp
  1               5                  10                  15 gat gac gat aag gtc gac aaa ggg aca tcc tac aaa ata tgc act gac       156
Asp Asp Asp Lys Val Asp Lys Gly Thr Ser Tyr Lys Ile Cys Thr Asp
                 20                  25                  30 aaa atg ttt ttt gtc aag aac cca act gac act ggt cat ggc act gtt       204
Lys Met Phe Phe Val Lys Asn Pro Thr Asp Thr Gly His Gly Thr Val
            35                  40                  45 gtg atg cag gtg aaa gtg tca aaa gga gcc ccc tgc agg att cca gtg       252
Val Met Gln Val Lys Val Ser Lys Gly Ala Pro Cys Arg Ile Pro Val
        50                  55                  60 ata gta gct gat gat ctt aca gcg gca atc aat aaa ggc att ttg gtt       300
Ile Val Ala Asp Asp Leu Thr Ala Ala Ile Asn Lys Gly Ile Leu Val
    65                  70                  75 aca gtt aac ccc atc gcc tca acc aat gat gat gaa gtg ctg att gag       348
Thr Val Asn Pro Ile Ala Ser Thr Asn Asp Asp Glu Val Leu Ile Glu
80                  85                  90                  95 gtg aac cca cct ttt gga gac agc tac att atc gtt ggg aga gga gat       396
Val Asn Pro Pro Phe Gly Asp Ser Tyr Ile Ile Val Gly Arg Gly Asp
                100                 105                 110 tca cgt ctc act tac cag tgg cac aaa gag gga agc tca ata gga aag       444
```

```
            Ser Arg Leu Thr Tyr Gln Trp His Lys Glu Gly Ser Ser Ile Gly Lys
                        115                 120                 125 act agt ggg gtt ctg gaa aac cgg gct gct cag ggc gat att act gca       492
Thr Ser Gly Val Leu Glu Asn Arg Ala Ala Gln Gly Asp Ile Thr Ala
            130                 135                 140 ccc ggc ggt gct cgc cgt tta acg ggt gat cag act gcc gct ctg cgt       540
Pro Gly Gly Ala Arg Arg Leu Thr Gly Asp Gln Thr Ala Ala Leu Arg
145                 150                 155 gat tct ctt agc gat aaa cct gca aaa aat att att ttg ctg att ggc       588
Asp Ser Leu Ser Asp Lys Pro Ala Lys Asn Ile Ile Leu Leu Ile Gly
160                 165                 170                 175 gat ggg atg ggg gac tcg gaa att act gcc gca cgt aat tat gcc gaa       636
Asp Gly Met Gly Asp Ser Glu Ile Thr Ala Ala Arg Asn Tyr Ala Glu
                180                 185                 190 ggt gcg ggc ggc ttt ttt aaa ggt ata gat gcc tta ccg ctt acc ggg       684
Gly Ala Gly Gly Phe Phe Lys Gly Ile Asp Ala Leu Pro Leu Thr Gly
            195                 200                 205 caa tac act cac tat gcg ctg aat aaa aaa acc ggc aaa ccg gac tac       732
Gln Tyr Thr His Tyr Ala Leu Asn Lys Lys Thr Gly Lys Pro Asp Tyr
        210                 215                 220 gtc acc gac tcg gct gca tca gca acc gcc tgg tca acc ggt gtc aaa       780
Val Thr Asp Ser Ala Ala Ser Ala Thr Ala Trp Ser Thr Gly Val Lys
225                 230                 235 acc tat aac ggc gcg ctg ggc gtc gat att cac gaa aaa gat cac cca       828
Thr Tyr Asn Gly Ala Leu Gly Val Asp Ile His Glu Lys Asp His Pro
240                 245                 250                 255 acg att ctg gaa atg gca aaa gcc gca ggt ctg gcg acc ggt aac gtt       876
Thr Ile Leu Glu Met Ala Lys Ala Ala Gly Leu Ala Thr Gly Asn Val
                260                 265                 270 tct acc gca gag ttg cag ggt gcc acg ccc gct gcg ctg gtg gca cat       924
Ser Thr Ala Glu Leu Gln Gly Ala Thr Pro Ala Ala Leu Val Ala His
            275                 280                 285 gtg acc tcg cgc aaa tgc tac ggt ccg agc gcg acc agt gaa aaa tgt       972
Val Thr Ser Arg Lys Cys Tyr Gly Pro Ser Ala Thr Ser Glu Lys Cys
        290                 295                 300 ccg ggt aac gct ctg gaa aaa ggc gga aaa gga tcg att acc gaa cag      1020
Pro Gly Asn Ala Leu Glu Lys Gly Gly Lys Gly Ser Ile Thr Glu Gln
305                 310                 315 ctg ctt aac gct cgt gcc gac gtt acg ctt ggc ggc ggc gca aaa acc      1068
Leu Leu Asn Ala Arg Ala Asp Val Thr Leu Gly Gly Gly Ala Lys Thr
320                 325                 330                 335 ttt gct gaa acg gca acc gct ggt gaa tgg cag gga aaa acg ctg cgt      1116
Phe Ala Glu Thr Ala Thr Ala Gly Glu Trp Gln Gly Lys Thr Leu Arg
                340                 345                 350 gaa cag gca cag gcg cgt ggt tat cag ttg gtg agc gat gct gcc tca      1164
Glu Gln Ala Gln Ala Arg Gly Tyr Gln Leu Val Ser Asp Ala Ala Ser
            355                 360                 365 ctg aat tcg gtg acg gaa gcg aat cag caa aaa ccc ctg ctt ggc ctg      1212
Leu Asn Ser Val Thr Glu Ala Asn Gln Gln Lys Pro Leu Leu Gly Leu
        370                 375                 380 ttt gct gac ggc aat atg cca gtg cgc tgg cta gga ccg aaa gca acg      1260
Phe Ala Asp Gly Asn Met Pro Val Arg Trp Leu Gly Pro Lys Ala Thr
385                 390                 395 tac cat ggc aat atc gat aag ccc gca gtc acc tgt acg cca aat ccg      1308
Tyr His Gly Asn Ile Asp Lys Pro Ala Val Thr Cys Thr Pro Asn Pro
400                 405                 410                 415 caa cgt aat gac agt gta cca acc ctg gcg cag atg acc gac aaa gcc      1356
Gln Arg Asn Asp Ser Val Pro Thr Leu Ala Gln Met Thr Asp Lys Ala
                420                 425                 430 att gaa ttg ttg agt aaa aat gag aaa ggc ttt ttc ctg caa gtt gaa      1404
```

```
Ile Glu Leu Leu Ser Lys Asn Glu Lys Gly Phe Phe Leu Gln Val Glu
            435                 440                 445 ggt gcg tca atc gat aaa cag aat cat gct gcg aat cct tgt ggg caa      1452
Gly Ala Ser Ile Asp Lys Gln Asn His Ala Ala Asn Pro Cys Gly Gln
            450                 455                 460 att ggc gag acg gtc gat ctc gat gaa gcc gta caa cgg gcg ctg gaa      1500
Ile Gly Glu Thr Val Asp Leu Asp Glu Ala Val Gln Arg Ala Leu Glu
465                 470                 475 ttc gct aaa aag gag ggt aac acg ctg gtc ata gtc acc gct gat cac      1548
Phe Ala Lys Lys Glu Gly Asn Thr Leu Val Ile Val Thr Ala Asp His
480                 485                 490                 495 gcc cac gcc agc cag att gtt gcg ccg gat acc aaa gct ccg ggc ctc      1596
Ala His Ala Ser Gln Ile Val Ala Pro Asp Thr Lys Ala Pro Gly Leu
                500                 505                 510 acc cag gcg cta aat acc aaa gat ggc gca gtg atg gtg atg agt tac      1644
Thr Gln Ala Leu Asn Thr Lys Asp Gly Ala Val Met Val Met Ser Tyr
            515                 520                 525 ggg aac tcc gaa gag gat tca caa gaa cat acc ggc agt cag ttg cgt      1692
Gly Asn Ser Glu Glu Asp Ser Gln Glu His Thr Gly Ser Gln Leu Arg
            530                 535                 540 att gcg gcg tat ggc ccg cat gcc gcc aat gtt gtt gga ctg acc gac      1740
Ile Ala Ala Tyr Gly Pro His Ala Ala Asn Val Val Gly Leu Thr Asp
545                 550                 555 cag acc gat ctc ttc tac acc atg aaa gcc gct ctg ggg ctg aaa taa      1788
Gln Thr Asp Leu Phe Tyr Thr Met Lys Ala Ala Leu Gly Leu Lys
560                 565                 570

<210> SEQ ID NO 12
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Arg Thr Pro Glu Met Pro Val Glu His His His His His Asp Asp
1               5                  10                  15

Asp Asp Lys Val Asp Lys Gly Thr Ser Tyr Lys Ile Cys Thr Asp Lys
                20                  25                  30

Met Phe Phe Val Lys Asn Pro Thr Asp Thr Gly His Gly Thr Val Val
            35                  40                  45

Met Gln Val Lys Val Ser Lys Gly Ala Pro Cys Arg Ile Pro Val Ile
        50                  55                  60

Val Ala Asp Asp Leu Thr Ala Ala Ile Asn Lys Gly Ile Leu Val Thr
65                  70                  75                  80

Val Asn Pro Ile Ala Ser Thr Asn Asp Asp Glu Val Leu Ile Glu Val
                85                  90                  95

Asn Pro Pro Phe Gly Asp Ser Tyr Ile Ile Val Gly Arg Gly Asp Ser
            100                 105                 110

Arg Leu Thr Tyr Gln Trp His Lys Glu Gly Ser Ser Ile Gly Lys Thr
        115                 120                 125

Ser Gly Val Leu Glu Asn Arg Ala Ala Gln Gly Asp Ile Thr Ala Pro
    130                 135                 140

Gly Gly Ala Arg Arg Leu Thr Gly Asp Gln Thr Ala Ala Leu Arg Asp
145                 150                 155                 160

Ser Leu Ser Asp Lys Pro Ala Lys Asn Ile Ile Leu Leu Ile Gly Asp
                165                 170                 175

Gly Met Gly Asp Ser Glu Ile Thr Ala Ala Arg Asn Tyr Ala Glu Gly
```

```
                        180                 185                 190
Ala Gly Gly Phe Phe Lys Gly Ile Asp Ala Leu Pro Leu Thr Gly Gln
            195                 200                 205

Tyr Thr His Tyr Ala Leu Asn Lys Lys Thr Gly Lys Pro Asp Tyr Val
        210                 215                 220

Thr Asp Ser Ala Ala Ser Ala Thr Ala Trp Ser Thr Gly Val Lys Thr
225                 230                 235                 240

Tyr Asn Gly Ala Leu Gly Val Asp Ile His Glu Lys Asp His Pro Thr
                245                 250                 255

Ile Leu Glu Met Ala Lys Ala Ala Gly Leu Ala Thr Gly Asn Val Ser
            260                 265                 270

Thr Ala Glu Leu Gln Gly Ala Thr Pro Ala Ala Leu Val Ala His Val
        275                 280                 285

Thr Ser Arg Lys Cys Tyr Gly Pro Ser Ala Thr Ser Glu Lys Cys Pro
    290                 295                 300

Gly Asn Ala Leu Glu Lys Gly Lys Gly Ser Ile Thr Glu Gln Leu
305                 310                 315             320

Leu Asn Ala Arg Ala Asp Val Thr Leu Gly Gly Ala Lys Thr Phe
                325                 330                 335

Ala Glu Thr Ala Thr Ala Gly Glu Trp Gln Gly Lys Thr Leu Arg Glu
            340                 345                 350

Gln Ala Gln Ala Arg Gly Tyr Gln Leu Val Ser Asp Ala Ser Leu
        355                 360                 365

Asn Ser Val Thr Glu Ala Asn Gln Gln Lys Pro Leu Leu Gly Leu Phe
    370                 375                 380

Ala Asp Gly Asn Met Pro Val Arg Trp Leu Gly Pro Lys Ala Thr Tyr
385                 390                 395                 400

His Gly Asn Ile Asp Lys Pro Ala Val Thr Cys Thr Pro Asn Pro Gln
                405                 410                 415

Arg Asn Asp Ser Val Pro Thr Leu Ala Gln Met Thr Asp Lys Ala Ile
            420                 425                 430

Glu Leu Leu Ser Lys Asn Glu Lys Gly Phe Phe Leu Gln Val Glu Gly
        435                 440                 445

Ala Ser Ile Asp Lys Gln Asn His Ala Ala Asn Pro Cys Gly Gln Ile
    450                 455                 460

Gly Glu Thr Val Asp Leu Asp Glu Ala Val Gln Arg Ala Leu Glu Phe
465                 470                 475                 480

Ala Lys Lys Glu Gly Asn Thr Leu Val Ile Val Thr Ala Asp His Ala
                485                 490                 495

His Ala Ser Gln Ile Val Ala Pro Asp Thr Lys Ala Pro Gly Leu Thr
            500                 505                 510

Gln Ala Leu Asn Thr Lys Asp Gly Ala Val Met Val Met Ser Tyr Gly
        515                 520                 525

Asn Ser Glu Glu Asp Ser Gln Glu His Thr Gly Ser Gln Leu Arg Ile
    530                 535                 540

Ala Ala Tyr Gly Pro His Ala Ala Asn Val Val Gly Leu Thr Asp Gln
545                 550                 555                 560

Thr Asp Leu Phe Tyr Thr Met Lys Ala Ala Leu Gly Leu Lys
                565                 570

<210> SEQ ID NO 13
<211> LENGTH: 7727
<212> TYPE: DNA
<213> ORGANISM: Artificial Sequence
<220> FEATURE:
```

<223> OTHER INFORMATION: Description of Artificial Sequence: Synthetic
      Plasmid pEBL1 sequence
<220> FEATURE:
<221> NAME/KEY: misc_feature
<222> LOCATION: (1732)..(2976)
<223> OTHER INFORMATION: kanamycine resistance cassette (from pUC4K)
      (antisense)

<400> SEQUENCE: 13

| | | | | | |
|---|---|---|---|---|---|
| aggcccttc | gtcttcaaga | attcgacacc | atcgaatggt | gcaaaacctt | tcgcggtatg | 60 |
| gcatgatagc | gcccggaaga | gagtcaattc | agggtggtga | atgtgaaacc | agtaacgtta | 120 |
| tacgatgtcg | cagagtatgc | cggtgtctct | tatcagaccg | tttcccgcgt | ggtgaaccag | 180 |
| gccagccacg | tttctgcgaa | aacgcgggaa | aaagtggaag | cggcgatggc | ggagctgaat | 240 |
| tacattccca | accgcgtggc | acaacaactg | gcgggcaaac | agtcgttgct | gattggcgtt | 300 |
| gccacctcca | gtctggccct | gcacgcgccg | tcgcaaattg | tcgcggcgat | taaatctcgc | 360 |
| gccgatcaac | tgggtgccag | cgtggtggtg | tcgatggtag | aacgaagcgg | cgtcgaagcc | 420 |
| tgtaaagcgg | cggtgcacaa | tcttctcgcg | caacgcgtca | gtgggctgat | cattaactat | 480 |
| ccgctggatg | accaggatgc | cattgctgtg | gaagctgcct | gcactaatgt | tccggcgtta | 540 |
| tttcttgatg | tctctgacca | gacacccatc | aacagtatta | ttttctccca | tgaagacggt | 600 |
| acgcgactgg | gcgtggagca | tctggtcgca | ttgggtcacc | agcaaatcgc | gctgttagcg | 660 |
| ggcccattaa | gttctgtctc | ggcgcgtctg | cgtctggctg | gctggcataa | atatctcact | 720 |
| cgcaatcaaa | ttcagccgat | agcggaacgg | gaaggcgact | ggagtgccat | gtccggtttt | 780 |
| caacaaacca | tgcaaatgct | gaatgagggc | atcgttccca | ctgcgatgct | ggttgccaac | 840 |
| gatcagatgg | cgctgggcgc | aatgcgcgcc | attaccgagt | ccgggctgcg | cgttggtgcg | 900 |
| gatatctcgg | tagtgggata | cgacgatacc | gaagacagct | catgttatat | cccgccgtca | 960 |
| accaccatca | acaggattt | cgcctgctg | ggcaaacca | gcgtggaccg | cttgctgcaa | 1020 |
| ctctctcagg | gccaggcggt | gaagggcaat | cagctgttgc | ccgtctcact | ggtgaaaaga | 1080 |
| aaaaccaccc | tggcgcccaa | tacgcaaacc | gcctctcccc | gcgcgttggc | cgattcatta | 1140 |
| atgcagctgg | cacgacaggt | ttcccgactg | gaaagcgggc | agtgaattct | ggcgaatcct | 1200 |
| ctgaccagcc | agaaaacgac | ctttctgtgg | tgaaaccgga | tgctgcaatt | cagagcgcca | 1260 |
| gcaagtgggg | gacagcagaa | gacctgaccg | ccgcagagtg | gatgtttgac | atggtgaaga | 1320 |
| ctatcgcacc | atcagccaga | aaaccgaatt | ttgctgggtg | gctaacgat | atccgcctga | 1380 |
| tgcgtgaacg | tgacgacgt | aaccaccgcg | acatgtgtgt | gctgttccgc | tgggcatgcc | 1440 |
| aggacaactt | ctggtccggt | aacgtgctga | gcccggccaa | gcttactccc | catcccctg | 1500 |
| ttgacaatta | atcatcggct | cgtataatgt | gtggaattgt | gagcggataa | caatttcaca | 1560 |
| caggaaacag | gatcctttaa | tgtatttgta | catggagaaa | ataaagtgaa | acaaagcact | 1620 |
| attgcactgg | cactcttacc | gttactgttt | accctgtga | caaagcccg | gacaccagaa | 1680 |
| atgcccgtcg | aacatcacca | tcaccatcac | gacgatgacg | ataaggtcga | cctgcagggg | 1740 |
| gggggggaa | agccacgttg | tgtctcaaaa | tctctgatgt | tacattgcac | aagataaaaa | 1800 |
| tatatcatca | tgaacaataa | aactgtctgc | ttacataaac | agtaatacaa | gggtgttat | 1860 |
| gagccatatt | caacgggaaa | cgtcttgctc | gaggccgcga | ttaaattcca | acatggatgc | 1920 |
| tgatttatat | gggtataaat | gggctcgcga | taatgtcggg | caatcaggtg | cgacaatcta | 1980 |
| tcgattgtat | gggaagcccg | atgcgccaga | gttgtttctg | aaacatggca | aaggtagcgt | 2040 |
| tgccaatgat | gttacagatg | agatggtcag | actaaactgg | ctgacggaat | ttatgcctct | 2100 |

```
tccgaccatc aagcatttta tccgtactcc tgatgatgca tggttactca ccactgcgat    2160 cccgggaaa acagcattcc aggtattaga agaatatcct gattcaggtg aaaatattgt    2220
tgatgcgctg gcagtgttcc tgcgccggtt gcattcgatt cctgtttgta attgtccttt    2280
taacagcgat cgcgtatttc gtctcgctca ggcgcaatca cgaatgaata acggtttggt    2340
tgatgcgagt gattttgatg acgagcgtaa tggtggcctg ttgaacaagt ctggaaagaa    2400
atgcataagc ttttgccatt ctcaccggat tcagtcgtca ctcatggtga tttctcactt    2460
gataaccttg tttttgacga ggggaaatta ataggttgta ttgatgttgg acgagtcgga    2520
atcgcagacc gataccagga tcttgccatc ctatggaact gcctcggtga gttttctcct    2580
tcattacaga aacggctttt tcaaaaatat ggtattgata atcctgatat gaataaattg    2640
cagtttcatt tgatgctcga tgagtttttc taatcagaat tggttaattg gttgtaacac    2700
tggcagagca ttacgctgac ttgacgggac ggcggctttg ttgaataaat cgaacttttg    2760
ctgagttgaa ggatcagatc acgcatcttc ccgacaacgc agaccgttcc gtggcaaagc    2820
aaaagttcaa atcaccaac tggtccacct acaacaaagc tctcatcaac cgtggctccc    2880
tcactttctg gctggatgat ggggcgattc aggcctggta tgagtcagca acaccttctt    2940
cacgaggcag acctcagcgc ccccccccc ctgcaggtcg acgagctccc ggggttctgg    3000
aaaaccgggc tgctcaggc gatattactg caccggcgg tgctcgccgt ttaacgggtg    3060
atcagactgc cgctctgcgt gattctctta gcgataaacc tgcaaaaaat attattttgc    3120
tgattggcga tgggatgggg gactcggaaa ttactgccgc acgtaattat gccgaaggtg    3180
cgggcggctt ttttaaaggt atagatgcct taccgcttac cgggcaatac actcactatg    3240
cgctgaataa aaaaaccggc aaaccggact acgtcaccga ctcggctgca tcagcaaccg    3300
cctggtcaac cggtgtcaaa acctataacg gcgcgctggg cgtcgatatt cacgaaaaag    3360
atcacccaac gattctggaa atggcaaaag ccgcaggtct ggcgaccggt aacgtttcta    3420
ccgcagagtt gcagggtgcc acgcccgctg cgctggtggc acatgtgacc tcgcgcaaat    3480
gctacggtcc gagcgcgacc agtgaaaaat gtccgggtaa cgctctggaa aaaggcggaa    3540
aaggatcgat taccgaacag ctgcttaacg ctcgtgccga cgttacgctt ggcggcggcg    3600
caaaaacctt tgctgaaacg gcaaccgctg gtgaatggca gggaaaaacg ctgcgtgaac    3660
aggcacaggc gcgtggttat cagttggtga gcgatgctgc ctcactgaat tcggtgacgg    3720
aagcgaatca gcaaaaaccc ctgcttggcc tgtttgctga cggcaatatg ccagtgcgct    3780
ggctaggacc gaaagcaacg taccatggca atatcgataa gcccgcagtc acctgtacgc    3840
caaatccgca acgtaatgac agtgtaccaa ccctggcgca gatgaccgac aaagccattg    3900
aattgttgag taaaaatgag aaaggctttt tcctgcaagt tgaaggtgcg tcaatcgata    3960
aacagaatca tgctgcgaat ccttgtgggc aaattggcga dacggtcgat ctcgatgaag    4020
ccgtacaacg ggcgctggaa ttcgctaaaa aggagggtaa cacgctggtc atagtcaccg    4080
ctgatcacgc ccacgccagc cagattgttg cgccggatac caaagctccg ggcctcaccc    4140
aggcgctaaa taccaaagat ggcgcagtga tggtgatgag ttacgggaac tccgaagagg    4200
attcacaaga acataccggc agtcagttgc gtattgcggc gtatggcccg catgccgcca    4260
atgttgttgg actgaccgac cagaccgatc tcttctacac catgaaagcc gctctggggc    4320
tgaaataaaa ccgcgcccgg cagtgaattt tcgctgccgg gtggtttttt tgctgttagc    4380
aaccagactt aatggcagat cacggcgcca tacgctcatg gttaaaacat gaagagggat    4440
ggtgctatga aaataacatt actggttacc ttgcttttcg gtctggtttt tttaaccacc    4500
```

```
gtcggcgctg ccgagagaac tttaaccoca caacaacagc gtatgacctc ctgtaatcag    4560
caggcgacgg cgcaggcgtt gaaagggat gctcgtaaga cctacatgag tgattgcctg    4620
aagaacagca agtctgcgcc tggcgaaaaa agtttgacgc cacagcagca aaagatgcgc    4680
gaatgcaata atcaagcaac acaacaatct ctgaaaggtg atgatcgtaa taagtttatg    4740
agtgcctgcc tcaagaaagc cgcctgatac ctgatagtgc taacgggtga gctacgaaaa    4800
tggctcaccc gaaatatcat acttctgcct ttagctccgt ctctataatt tgggaaaatt    4860
gtttctgaat gttcccaaaa ataatgaatg atgaaaactt tttcaaaaaa gcggcggcgc    4920
acggggagga acctccttta actcctcaaa acgaacatca gcggtccggg ctgcgcttcg    4980
cccgtcgcgt cagactaccc cgtgcggttg gcctggctgg catgttctta ccgattgctt    5040
caacgctggt ttcacacccg ccgccgggct ggtggtggct ggtgttggtc ggctgggcgt    5100
tcgtctggcc gcatttagcc tggcagatag cgagcagggc cgtcgatccg cttagccggg    5160
aaatttacaa cttaaaaacc gatgcagtat tagcgggaat gtgggtaggc gtaatgggcg    5220
taaacgtgct gccttccacc gcgatgttga tgattatgtg tctgaatttg atgggggcag    5280
gcggcccccg tctgtttgtc gcgggtctgg tgttgatggt ggtttcctgc cttgtcaccc    5340
tcgagcaaga cgtttcccgt tgaatatggc tcataacacc ccttgtatta ctgtttatgt    5400
aagcagacag ttttattgtt catgatgata tattttatc ttgtgcaatg taacatcaga    5460
gattttgaga cacaacgtgg ctttgttgaa taaatcgaac ttttgctgag ttgaaggatc    5520
agatcacgca tcttcccgac aacgcagacc gttccgtggc aaagcaaaag ttcaaaatca    5580
ccaactggtc cacctacaac aaagctctca tcaaccgtgg ctccctcact ttctggctgg    5640
atgatggggc gattcaggcc tggtatgagt cagcaacacc ttcttcacga ggcagacctc    5700
agcgctagcg gagtgtatac tggcttacta tgttggcact gatgagggtg tcagtgaagt    5760
gcttcatgtg gcaggagaaa aaaggctgca ccggtgcgtc agcagaatat gtgatacagg    5820
atatattccg cttcctcgct cactgactcg ctacgctcgg tcgttcgact gcggcgagcg    5880
gaaatggctt acgaacgggg cggagatttc ctggaagatg ccaggaagat acttaacagg    5940
gaagtgagag ggccgcggca aagccgtttt tccataggct ccgccccct gacaagcatc    6000
acgaaatctg acgctcaaat cagtggtggc gaaacccgac aggactataa agataccagg    6060
cgtttccccc tggcggctcc ctcgtgcgct ctcctgttcc tgccctttcgg tttaccggtg    6120
tcattccgct gttatggccg cgtttgtctc attccacgcc tgacactcag ttccgggtag    6180
gcagttcgct ccaagctgga ctgtatgcac gaaccccccg ttcagtccga ccgctgcgcc    6240
ttatccggta actatcgtct tgagtccaac ccggaaagac atgcaaaagc accactggca    6300
gcagccactg gtaattgatt tagaggagtt agtcttgaag tcatgcgccg gttaaggcta    6360
aactgaaagg acaagttttg gtgactgcgc tcctccaagc cagttacctc ggttcaaaga    6420
gttggtagct cagagaacct tcgaaaaacc gccctgcaag gcggtttttt cgttttcaga    6480
gcaagagatt acgcgcagac caaaacgatc tcaagaagat catcttatta agggtctga    6540
cgctcagtgg aacgaaaact cacgttaagg gattttggtc atgagattat caaaaaggat    6600
cttcacctag atccttttaa attaaaaatg aagttttaaa tcaatctaaa gtatatatga    6660
gtaaacttgg tctgacagtt accaatgctt aatcagtgag gcacctatct cagcgatctg    6720
tctatttcgt tcatccatag ttgcctgact ccccgtcgtg tagataacta cgatacggga    6780
gggcttacca tctggcccca gtgctgcaat gataccgcga cccacgct caccggctcc    6840
agatttatca gcaataaacc agccagccgg aagggccgag cgcagaagtg gtcctgcaac    6900
```

-continued

```
tttatccgcc tccatccagt ctattaattg ttgccgggaa gctagagtaa gtagttcgcc    6960
agttaatagt ttgcgcaacg ttgttgccat tgctgcaggc atcgtggtgt cacgctcgtc    7020
gtttggtatg gcttcattca gctccggttc ccaacgatca aggcgagtta catgatcccc    7080
catgttgtgc aaaaaagcgg ttagctcctt cggtcctccg atcgttgtca gaagtaagtt    7140
ggccgcagtg ttatcactca tggttatggc agcactgcat aattctctta ctgtcatgcc    7200
atccgtaaga tgcttttctg tgactggtga gtactcaacc aagtcattct gagaatagtg    7260
tatgcggcga ccgagttgct cttgcccggc gtcaacacgg ataataccg cgccacatag     7320 cagaacttta aaagtgctca tcattggaaa acgttcttcg gggcgaaaac tctcaaggat    7380
cttaccgctg ttgagatcca gttcgatgta acccactcgt gcacccaact gatcttcagc    7440
atcttttact ttcaccagcg tttctgggtg agcaaaaaca ggaaggcaaa atgccgcaaa    7500
aaagggaata agggcgacac ggaaatgttg aatactcata ctcttccttt ttcaatatta    7560
ttgaagcatt tatcagggtt attgtctcat gagcggatac atatttgaat gtatttagaa    7620
aaataaacaa ataggggttc cgcgcacatt tccccgaaaa gtgccacctg acgtctaaga    7680
aaccattatt atcatgacat taacctataa aaataggcgt atgcacg                  7727
```

```
<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gccggcggtc gacaaaggga tgtcatatgt gatgtgcac                            39

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtttagtact agttttccct atgctgcttc ccttc                                35

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gccggcggtc gacaaaggaa caacctatgg cgtctg                               36

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggtgagtact agttttgcca atgctgctac cagac                                35
```

```
<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcactggcac tcttaccgtt ac                                              22

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cagtctgatc acccgttaaa c                                               21

<210> SEQ ID NO 20
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide fragment of SEQ ID NO: 13
<220> FEATURE:
<221> NAME/KEY: CDS
<222> LOCATION: (1)..(126)
<223> OTHER INFORMATION: 1-63 = signal peptide; 64-81 = mature PhoA;
      88-105 = His-tag

<400> SEQUENCE: 20 gtg aaa caa agc act att gca ctg gca ctc tta ccg tta ctg ttt acc       48
Met Lys Gln Ser Thr Ile Ala Leu Ala Leu Leu Pro Leu Leu Phe Thr
1               5                   10                  15 cct gtg aca aaa gcc cgg aca cca gaa atg ccc gtc gaa cat cac cat       96
Pro Val Thr Lys Ala Arg Thr Pro Glu Met Pro Val Glu His His His
            20                  25                  30 cac cat cac gac gat gac gat aag gtc gac                              126
His His His Asp Asp Asp Asp Lys Val Asp
        35                  40

<210> SEQ ID NO 21
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Lys Gln Ser Thr Ile Ala Leu Ala Leu Leu Pro Leu Leu Phe Thr
1               5                   10                  15

Pro Val Thr Lys Ala Arg Thr Pro Glu Met Pro Val Glu His His His
            20                  25                  30

His His His Asp Asp Asp Asp Lys Val Asp
        35                  40

<210> SEQ ID NO 22
<211> LENGTH: 32
<212> TYPE: DNA
<213> ORGANISM: Artificial Sequence
<220> FEATURE:
```

<223> OTHER INFORMATION: Description of Artificial Sequence: Synthetic
      oligonucleotide fragment of SEQ ID NO: 13
<220> FEATURE:
<221> NAME/KEY: CDS
<222> LOCATION: (3)..(32)
<223> OTHER INFORMATION: 18-32 = PhoA

<400> SEQUENCE: 22

```
gt cga cga gct ccc ggg gtt ctg gaa aac cgg                            32
   Arg Arg Ala Pro Gly Val Leu Glu Asn Arg
    1               5                  10
```

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

```
Arg Arg Ala Pro Gly Val Leu Glu Asn Arg
 1               5                  10
```

<210> SEQ ID NO 24
<211> LENGTH: 450
<212> TYPE: PRT
<213> ORGANISM: Artificial Sequence
<220> FEATURE:
<223> OTHER INFORMATION: Description of Artificial Sequence: Synthetic
      PhoA polypeptide (D153G, D330N - numbering according
      to related structure with access number 1KH7A)

<400> SEQUENCE: 24

```
Arg Thr Pro Glu Met Pro Val Leu Glu Asn Arg Ala Ala Gln Gly Asp
 1               5                  10                  15

Ile Thr Ala Pro Gly Gly Ala Arg Arg Leu Thr Gly Asp Gln Thr Ala
             20                  25                  30

Ala Leu Arg Asp Ser Leu Ser Asp Lys Pro Ala Lys Asn Ile Ile Leu
         35                  40                  45

Leu Ile Gly Asp Gly Met Gly Asp Ser Glu Ile Thr Ala Ala Arg Asn
 50                  55                  60

Tyr Ala Glu Gly Ala Gly Gly Phe Phe Lys Gly Ile Asp Ala Leu Pro
 65                  70                  75                  80

Leu Thr Gly Gln Tyr Thr His Tyr Ala Leu Asn Lys Lys Thr Gly Lys
                 85                  90                  95

Pro Asp Tyr Val Thr Asp Ser Ala Ala Ser Ala Thr Ala Trp Ser Thr
            100                 105                 110

Gly Val Lys Thr Tyr Asn Gly Ala Leu Gly Val Asp Ile His Glu Lys
        115                 120                 125

Asp His Pro Thr Ile Leu Glu Met Ala Lys Ala Ala Gly Leu Ala Thr
    130                 135                 140

Gly Asn Val Ser Thr Ala Glu Leu Gln Gly Ala Thr Pro Ala Ala Leu
145                 150                 155                 160

Val Ala His Val Thr Ser Arg Lys Cys Tyr Gly Pro Ser Ala Thr Ser
                165                 170                 175

Glu Lys Cys Pro Gly Asn Ala Leu Glu Lys Gly Gly Lys Gly Ser Ile
            180                 185                 190

Thr Glu Gln Leu Leu Asn Ala Arg Ala Asp Val Thr Leu Gly Gly Gly
        195                 200                 205

Ala Lys Thr Phe Ala Glu Thr Ala Thr Ala Gly Glu Trp Gln Gly Lys
    210                 215                 220
```

```
Thr Leu Arg Glu Gln Ala Gln Ala Arg Gly Tyr Gln Leu Val Ser Asp
225                 230                 235                 240

Ala Ala Ser Leu Asn Ser Val Thr Glu Ala Asn Gln Gln Lys Pro Leu
            245                 250                 255

Leu Gly Leu Phe Ala Asp Gly Asn Met Pro Val Arg Trp Leu Gly Pro
            260                 265                 270

Lys Ala Thr Tyr His Gly Asn Ile Asp Lys Pro Ala Val Thr Cys Thr
            275                 280                 285

Pro Asn Pro Gln Arg Asn Asp Ser Val Pro Thr Leu Ala Gln Met Thr
            290                 295                 300

Asp Lys Ala Ile Glu Leu Leu Ser Lys Asn Glu Lys Gly Phe Phe Leu
305                 310                 315                 320

Gln Val Glu Gly Ala Ser Ile Asp Lys Gln Asn His Ala Ala Asn Pro
                325                 330                 335

Cys Gly Gln Ile Gly Glu Thr Val Asp Leu Asp Glu Ala Val Gln Arg
                340                 345                 350

Ala Leu Glu Phe Ala Lys Lys Glu Gly Asn Thr Leu Val Ile Val Thr
                355                 360                 365

Ala Asp His Ala His Ala Ser Gln Ile Val Ala Pro Asp Thr Lys Ala
370                 375                 380

Pro Gly Leu Thr Gln Ala Leu Asn Thr Lys Asp Gly Ala Val Met Val
385                 390                 395                 400

Met Ser Tyr Gly Asn Ser Glu Glu Asp Ser Gln Glu His Thr Gly Ser
                405                 410                 415

Gln Leu Arg Ile Ala Ala Tyr Gly Pro His Ala Ala Asn Val Val Gly
                420                 425                 430

Leu Thr Asp Gln Thr Asp Leu Phe Tyr Thr Met Lys Ala Ala Leu Gly
                435                 440                 445

Leu Lys
    450

<210> SEQ ID NO 25
<211> LENGTH: 450
<212> TYPE: PRT
<213> ORGANISM: Artificial Sequence
<220> FEATURE:
<223> OTHER INFORMATION: Description of Artificial Sequence: Synthetic
      PhoA polypeptide (numbering according to related structure
      with access number 1KH7A)

<400> SEQUENCE: 25

Arg Thr Pro Glu Met Pro Val Leu Glu Asn Arg Ala Ala Gln Gly Asp
1               5                   10                  15

Ile Thr Ala Pro Gly Gly Ala Arg Arg Leu Thr Gly Asp Gln Thr Ala
            20                  25                  30

Ala Leu Arg Asp Ser Leu Ser Asp Lys Pro Ala Lys Asn Ile Ile Leu
            35                  40                  45

Leu Ile Gly Asp Gly Met Gly Asp Ser Glu Ile Thr Ala Ala Arg Asn
50                  55                  60

Tyr Ala Glu Gly Ala Gly Gly Phe Phe Lys Gly Ile Asp Ala Leu Pro
65                  70                  75                  80

Leu Thr Gly Gln Tyr Thr His Tyr Ala Leu Asn Lys Lys Thr Gly Lys
                85                  90                  95

Pro Asp Tyr Val Thr Asp Ser Ala Ala Ser Ala Thr Ala Trp Ser Thr
            100                 105                 110

Gly Val Lys Thr Tyr Asn Gly Ala Leu Gly Val Asp Ile His Glu Lys
```

```
            115                 120                 125
Asp His Pro Thr Ile Leu Glu Met Ala Lys Ala Gly Leu Ala Thr
130                 135                 140

Gly Asn Val Ser Thr Ala Glu Leu Gln Asp Ala Thr Pro Ala Leu
145                 150                 155                 160

Val Ala His Val Thr Ser Arg Lys Cys Tyr Gly Pro Ser Ala Thr Ser
                165                 170                 175

Glu Lys Cys Pro Gly Asn Ala Leu Glu Lys Gly Lys Gly Ser Ile
            180                 185                 190

Thr Glu Gln Leu Leu Asn Ala Arg Ala Asp Val Thr Leu Gly Gly Gly
                195                 200                 205

Ala Lys Thr Phe Ala Glu Thr Ala Thr Ala Gly Glu Trp Gln Gly Lys
    210                 215                 220

Thr Leu Arg Glu Gln Ala Gln Ala Arg Gly Tyr Gln Leu Val Ser Asp
225                 230                 235                 240

Ala Ala Ser Leu Asn Ser Val Thr Glu Ala Asn Gln Gln Lys Pro Leu
                245                 250                 255

Leu Gly Leu Phe Ala Asp Gly Asn Met Pro Val Arg Trp Leu Gly Pro
            260                 265                 270

Lys Ala Thr Tyr His Gly Asn Ile Asp Lys Pro Ala Val Thr Cys Thr
    275                 280                 285

Pro Asn Pro Gln Arg Asn Asp Ser Val Pro Thr Leu Ala Gln Met Thr
290                 295                 300

Asp Lys Ala Ile Glu Leu Leu Ser Lys Asn Glu Lys Gly Phe Phe Leu
305                 310                 315                 320

Gln Val Glu Gly Ala Ser Ile Asp Lys Gln Asp His Ala Ala Asn Pro
                325                 330                 335

Cys Gly Gln Ile Gly Glu Thr Val Asp Leu Asp Glu Ala Val Gln Arg
            340                 345                 350

Ala Leu Glu Phe Ala Lys Lys Glu Gly Asn Thr Leu Val Ile Val Thr
    355                 360                 365

Ala Asp His Ala His Ala Ser Gln Ile Val Ala Pro Asp Thr Lys Ala
370                 375                 380

Pro Gly Leu Thr Gln Ala Leu Asn Thr Lys Asp Gly Ala Val Met Val
385                 390                 395                 400

Met Ser Tyr Gly Asn Ser Glu Glu Asp Ser Gln Glu His Thr Gly Ser
                405                 410                 415

Gln Leu Arg Ile Ala Ala Tyr Gly Pro His Ala Ala Asn Val Val Gly
            420                 425                 430

Leu Thr Asp Gln Thr Asp Leu Phe Tyr Thr Met Lys Ala Ala Leu Gly
                435                 440                 445

Leu Lys
    450

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tcaatatgct gaaacgcgcg agaaaccg                                      28

<210> SEQ ID NO 27
```

```
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ttgcaccaac agtcaatgtc ttcaggttc                                          29

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cgtctcagtg atccggggg                                                     19

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgccacaagg ggcatgaaca g                                                  21

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
taacatcatc atgagacaga gc                                                 22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctctgttgtc ttaaacaaga ga                                                 22

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 32

His His His His His His
1               5

<210> SEQ ID NO 33
<211> LENGTH: 152
```

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(120)
<220> FEATURE:
<221> NAME/KEY: CDS
<222> LOCATION: (123)..(152)

<400> SEQUENCE: 33 gtg aaa caa agc act att gca ctg gca ctc tta ccg tta ctg ttt acc      48
Met Lys Gln Ser Thr Ile Ala Leu Ala Leu Leu Pro Leu Leu Phe Thr
 1               5                  10                  15 cct gtg aca aaa gcc cgg aca cca gaa atg ccc gtc gaa cat cac cat      96
Pro Val Thr Lys Ala Arg Thr Pro Glu Met Pro Val Glu His His His
             20                  25                  30 cac cat cac gac gat gac gat aag gt cga cga gct ccc ggg gtt ctg     143
His His His Asp Asp Asp Asp Lys    Arg Arg Ala Pro Gly Val Leu
         35                  40                      45 gaa aac cgg                                                         152
Glu Asn Arg
         50

<210> SEQ ID NO 34
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Lys Gln Ser Thr Ile Ala Leu Ala Leu Leu Pro Leu Leu Phe Thr
 1               5                  10                  15

Pro Val Thr Lys Ala Arg Thr Pro Glu Met Pro Val Glu His His His
             20                  25                  30

His His His Asp Asp Asp Asp Lys
         35                  40
```